United States Patent
Hwang et al.

(10) Patent No.: US 9,793,491 B2
(45) Date of Patent: Oct. 17, 2017

(54) COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Seokhwan Hwang, Yongin (KR); Mieun Jun, Yongin (KR); Hyejin Jung, Yongin (KR); Youngkook Kim, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 343 days.

(21) Appl. No.: 14/702,620

(22) Filed: May 1, 2015

(65) Prior Publication Data

US 2016/0155952 A1 Jun. 2, 2016

(30) Foreign Application Priority Data

Dec. 2, 2014 (KR) ........................ 10-2014-0170821

(51) Int. Cl.
*H01L 51/00* (2006.01)
*C07D 307/77* (2006.01)
(Continued)

(52) U.S. Cl.
CPC ........ *H01L 51/0061* (2013.01); *C07D 307/77* (2013.01); *C07D 307/91* (2013.01);
(Continued)

(58) Field of Classification Search
CPC ............... H01L 51/0061; H01L 51/006; H01L 51/0054; H01L 51/0073; H01L 51/0081;
(Continued)

(56) References Cited

U.S. PATENT DOCUMENTS 5,981,574 A * 11/1999 Gulavita .............. C07D 307/77
514/468
6,534,199 B1 * 3/2003 Hosokawa .......... H01L 51/0052
252/301.16
(Continued)

FOREIGN PATENT DOCUMENTS

JP 2008-291263 A 12/2008
JP 2013-63930 A 4/2013
(Continued)

*Primary Examiner* — Mike M Dollinger
(74) *Attorney, Agent, or Firm* — Lewis Roca Rothgerber Christie LLP

(57) ABSTRACT

The present disclosure relates to a compound represented by Formula 1 and an organic light-emitting device including the same.

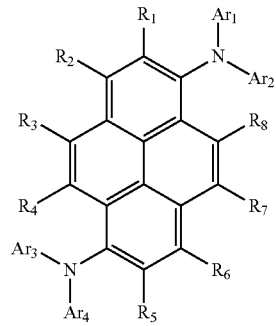

Formula 1

The compound represented by Formula 1 has excellent stability and is suitable as an electron transporting material. An organic light-emitting device using the compound of
(Continued)

Formula 1 may have high efficiency, low voltage, high luminance, and long lifespan.

20 Claims, 1 Drawing Sheet

(51) Int. Cl.
*C09K 11/06* (2006.01)
*C07F 7/08* (2006.01)
*C07D 307/91* (2006.01)
*C07D 409/12* (2006.01)
*H05B 33/14* (2006.01)
*H01L 51/50* (2006.01)

(52) U.S. Cl.
CPC .......... *C07D 409/12* (2013.01); *C07F 7/0809* (2013.01); *C07F 7/0812* (2013.01); *C09K 11/06* (2013.01); *H01L 51/006* (2013.01); *H01L 51/0054* (2013.01); *H01L 51/0073* (2013.01); *H05B 33/14* (2013.01); C09K 2211/1007 (2013.01); C09K 2211/1011 (2013.01); C09K 2211/1088 (2013.01); *H01L 51/0058* (2013.01); *H01L 51/0072* (2013.01); *H01L 51/0081* (2013.01); *H01L 51/5012* (2013.01)

(58) Field of Classification Search
CPC ............ H01L 51/0072; H01L 51/0058; H01L 51/5012; H05B 33/14; C07F 7/0809; C07F 7/0812; C07D 307/91; C07D 307/77; C09K 11/06; C09K 2211/1088; C09K 2211/1007; C09K 2211/1011
USPC ........................................................ 428/690
See application file for complete search history.

(56) References Cited

U.S. PATENT DOCUMENTS

| | | | |
|---|---|---|---|
| 7,732,063 B2 | 6/2010 | Matsuura et al. | |
| 7,854,999 B2* | 12/2010 | Park | C07C 13/62 313/504 |
| 8,334,648 B2 | 12/2012 | Matsuura et al. | |
| 2007/0237984 A1 | 10/2007 | Matsuura et al. | |
| 2010/0045174 A1* | 2/2010 | Okabe | C08G 65/18 313/504 |
| 2010/0052526 A1* | 3/2010 | Je | C07C 211/61 313/504 |
| 2010/0108995 A1* | 5/2010 | Yagi | C07D 209/08 257/40 |
| 2010/0270913 A1 | 10/2010 | Matsuura et al. | |
| 2011/0089410 A1* | 4/2011 | Stoessel | C07F 1/005 257/40 |
| 2012/0056165 A1* | 3/2012 | Kawamura | C09K 11/06 257/40 |
| 2014/0346482 A1 | 11/2014 | Mizuki et al. | |
| 2016/0155952 A1* | 6/2016 | Hwang | H01L 51/0061 257/40 |
| 2017/0040535 A1* | 2/2017 | Ogita | C07D 307/77 |
| 2017/0073528 A1* | 3/2017 | Funahashi | C09D 11/033 |
| 2017/0077411 A1* | 3/2017 | Kim | H01L 51/0061 |
| 2017/0148993 A1* | 5/2017 | Funahashi | H01L 51/0058 |

FOREIGN PATENT DOCUMENTS

| | | |
|---|---|---|
| JP | 2013-63931 A | 4/2013 |
| KR | 10-2010-0024894 A | 3/2010 |
| KR | 10-2011-0015213 A | 2/2011 |
| KR | 10-2011-0094271 A | 8/2011 |

\* cited by examiner

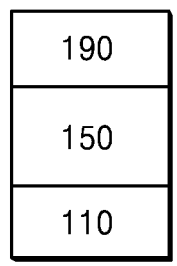

COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2014-0170821, filed on Dec. 2, 2014, in the Korean Intellectual Property Office, the disclosure of which is incorporated herein in its entirety by reference.

BACKGROUND

1. Field

One or more aspects of embodiments of the present invention relate to a compound and an organic light-emitting device including the same.

2. Description of the Related Art

Organic light-emitting devices (OLEDs) are self-emission devices that have wide viewing angles, high contrast ratios, and short response times. In addition, OLEDs exhibit excellent luminance, low driving voltage, and quick response speed characteristics, and produce full-color images.

An organic light-emitting device may have a structure including an anode disposed on a substrate, a hole transport layer, an emission layer, an electron transport layer, and a cathode which are sequentially stacked on the anode in the stated order. Here, the hole transport layer, the emission layer, and the electron transport layer may be organic thin films formed of organic compounds.

The operating principle of an organic light-emitting device having the above-described structure is as follows:

When a voltage is applied between the anode and the cathode, holes provided from the anode may move toward the emission layer through the hole transport layer, and electrodes provided from the cathode may move toward the emission layer through the electron transport layer. The holes and the electrons are then recombined in the emission layer to produce excitons. These excitons change from an excited state to a ground state to thereby generate light.

There is a need to develop a material that has improved electric stability, high charge transporting and/or light-emitting capability, high glass transition temperature, and capability to prevent or reduce crystallization, as compared to an organic material of the related art.

SUMMARY

One or more aspects of embodiments of the present invention include a compound that is suitable as an electron transporting material and has excellent electric characteristics, high charge transporting and light-emitting capability, high glass transition temperature, and/or high capability to prevent or substantially reduce crystallization. An organic light-emitting device including the compound may have high efficiency, low voltage, high luminance, and/or long lifespan.

Additional aspects of the present invention will be set forth in part in the description which follows and, in part, will be apparent from the description, or may be learned by practice of the presented embodiments.

According to one or more exemplary embodiments, a compound is represented by Formula 1:

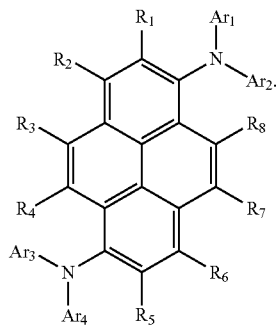

Formula 1

In Formula 1, $R_1$ to $R_8$ and $Ar_1$ to $Ar_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

where at least one selected from $Ar_1$ to $Ar_4$ is represented by Formula 1-a:

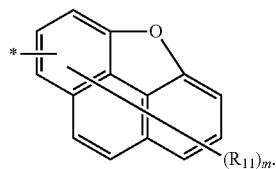

Formula 1-a

In Formula 1-a, $R_{11}$ is the same as defined in connection with $R_1$ to $R_8$;

m is an integer selected from 1 to 7; and

* indicates a binding site.

In Formulae 1 and 1-a, at least one of the substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

where $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to one or more exemplary embodiments, an organic light-emitting device includes: a first electrode; a second electrode facing the first electrode; and an organic layer between the first electrode and the second electrode, wherein the organic layer includes an emission layer and the compound represented by Formula 1.

According to one or more exemplary embodiments, a flat panel display apparatus may include the organic light-emitting device wherein a first electrode is electrically connected to a source electrode or drain electrode of a thin film transistor.

BRIEF DESCRIPTION OF THE DRAWINGS

These and/or other aspects will become apparent and more readily appreciated from the following description of the exemplary embodiments, taken in conjunction with the accompanying drawing which is a schematic view of an organic light-emitting device according to one or more embodiments of the present invention.

DETAILED DESCRIPTION

Reference will now be made in detail to embodiments, examples of which are illustrated in the accompanying drawing, wherein like reference numerals refer to like elements throughout. In this regard, the present exemplary embodiments may have different forms and should not be construed as being limited to the descriptions set forth herein. Accordingly, the exemplary embodiments are merely described below, by referring to the drawing, to explain aspects of the present description. As used herein, the term "and/or" includes any and all combinations of one or more of the associated listed items. Expressions such as "at least one of", when preceding a list of elements, modify the entire list of elements and do not modify the individual elements of the list. Further, the use of "may" when describing embodiments of the present invention refers to "one or more embodiments of the present invention."

In addition, as used herein, the terms "use," "using," and "used" may be considered synonymous with the terms "utilize," "utilizing," and "utilized," respectively. Also, the term "exemplary" is intended to refer to an example or illustration.

As used herein, the term "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. §1 12, first paragraph, and 35 U.S.C. §132(a).

According to one or more exemplary embodiments, a compound is represented by Formula 1:

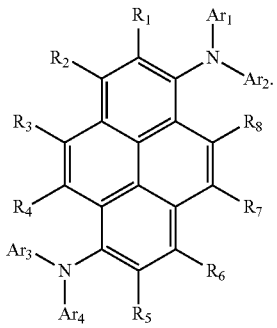

Formula 1

In Formula 1, $R_1$ to $R_8$ and $Ar_1$ to $Ar_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

where at least one selected from $Ar_1$ to $Ar_4$ may be represented by Formula 1-a:

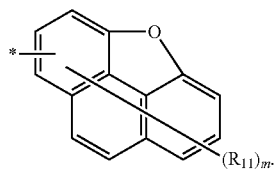

Formula 1-a

In Formula 1-a, $R_{11}$ may be the same as defined in connection with $R_1$ to $R_8$;

m may be an integer selected from 1 to 7; and

* indicates a binding site.

In Formulae 1 and 1-a, at least one of the substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

where $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

Compounds represented by Formula 1 and including a condensed ring structure may have a high glass transition temperature (Tg) or a high melting point, due to the presence of a condensed ring. Therefore, during emission, an organic light-emitting device may have improved heat resistance to Joule heating generated in an organic layer of the organic light-emitting device, between the layers included in the organic layer, and between the organic layer and a metal electrode, and an improved resistance to a high temperature. Thus, an organic light-emitting device manufactured using the compound represented by Formula 1 may retain high durability during storing and driving.

In addition, Formula 1-a has a phenanthrofuran structure in which phenanthrene structure is condensed with a furan structure, so that π-electrons in the overall structure are delocalized and lone pairs of oxygen (O) are capable to partially provide excess electrons.

Accordingly, π→π* transition and n→π* transition may occur easily due to a phenanthrofuran structure connected to an amine group as well as the pyrene structure enriched with π-electrons that is positioned in the center of Formula 1.

Based on this principle, ultimately, molecular extinction coefficient in the structure of Formula 1 may increase. Such an increase of the molecular extinction coefficient may lead to increase of luminous efficiency of the molecule, and thus, the compound represented by Formula 1 may have an improved luminous efficiency compared to other known and/or commonly used pyrene derivatives.

Accordingly, when the compound represented by Formula 1 is used as a dopant in an emission layer in an organic light-emitting device, the organic light-emitting device may have high efficiency.

In some embodiments, when a compound represented by Formula 4 (described below) is used as a host in the emission layer together with the compound of Formula 1 (used as a dopant), the organic light-emitting device may have an excellent efficiency.

Substituents of Formula 1 will be described in more detail below.

In some embodiments, among $Ar_1$ to $Ar_4$ in Formula 1, substituents other than Formula 1-a may be each independently selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formula 1, $R_1$ to $R_8$ may be each independently selected from a hydrogen, a deuterium, a substituted or unsubstituted $C_1$-$C_{60}$ alkyl group, a substituted or unsubstituted $C_6$-$C_{60}$ aryl group, and —Si($Q_3$)($Q_4$)($Q_5$), where $Q_3$ to $Q_5$ are as defined above.

In some embodiments, among $Ar_1$ to $Ar_4$ in Formula 1, substituents other than Formula 1-a may be each independently represented by any one of Formulae 2a to 2d:

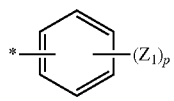

2a

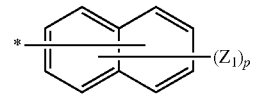

2b

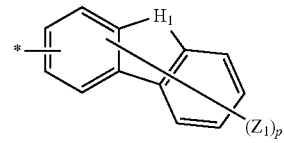

2c

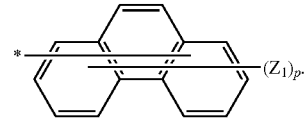

2d

In Formulae 2a to 2d, $Z_1$ may be selected from a hydrogen atom, a deuterium, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ condensed polycyclic group, a halogen group, a cyano group, a nitro group, a hydroxyl group, and a carboxyl group;

$H_1$ may be selected from —O—, —S—, and —$CR_{51}R_{52}$—; p may be an integer selected from 1 to 9;

$R_{51}$ and $R_{52}$ may be the same as defined in connection with $R_1$ to $R_8$; and

* indicates a binding site.

In some embodiments, in Formula 1, $R_2$ and $R_6$ may be each independently selected from a hydrogen, a deuterium, a $C_1$-$C_{20}$ alkyl group, a $C_6$-$C_{20}$ aryl group, and —Si($Q_{41}$)($Q_{42}$)($Q_{43}$), where $Q_{41}$ to $Q_{43}$ may be each independently selected from a $C_1$-$C_{60}$ alkyl group and a $C_6$-$C_{60}$ aryl group. In some embodiments, in Formula 1, $R_2$ and $R_6$ may be each independently selected from a hydrogen, a deuterium, a methyl group, a t-butyl group, a phenyl group, and a tri-methyl silyl group.

In some embodiments, in Formula 1, $R_1$, $R_3$ to $R_5$, $R_7$, and $R_8$ may be each independently selected from a hydrogen and a deuterium.

In some embodiments, in Formula 1-a, $R_{11}$ may be selected from a hydrogen and a deuterium.

In some embodiments, the compound represented by Formula 1 may be represented by any one of Formula 2 and 3:

Formula 2

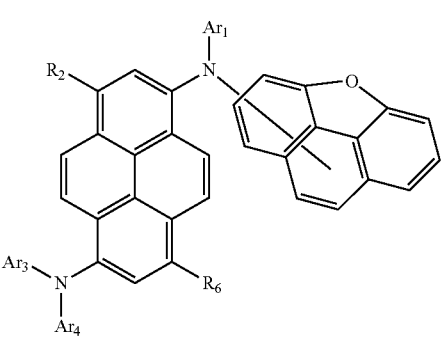

Formula 3
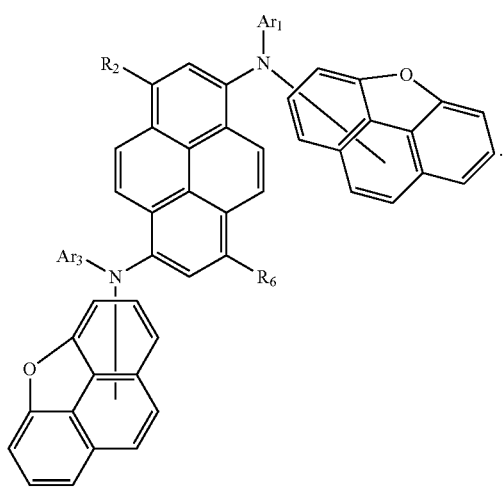
Examples of the compound represented by Formula 1 include compounds shown below, but embodiments of the present invention are not limited thereto.
1
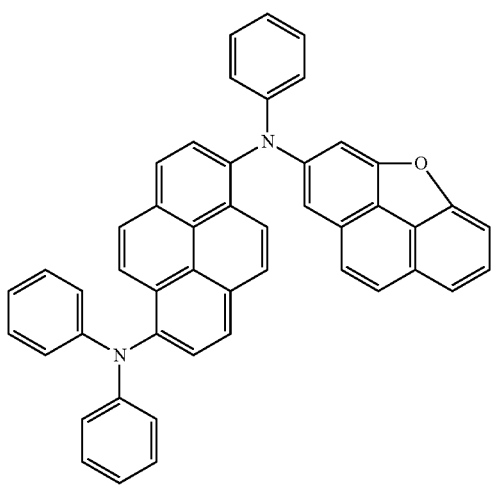
2
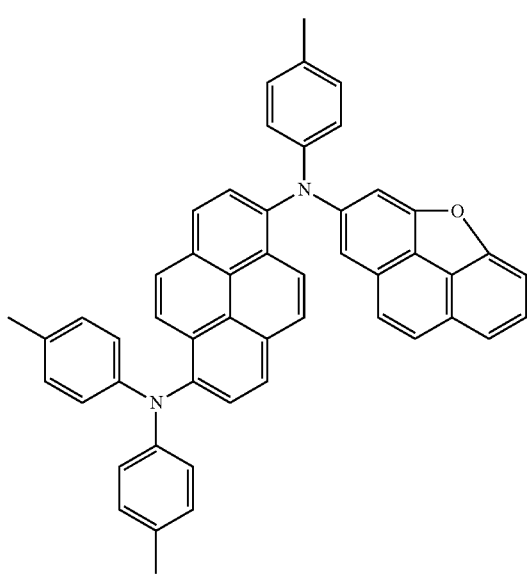
3
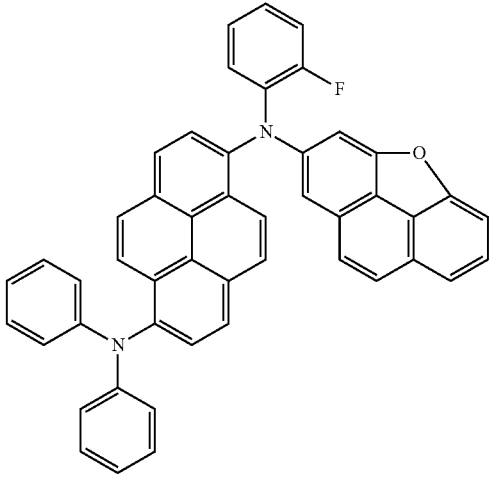
4
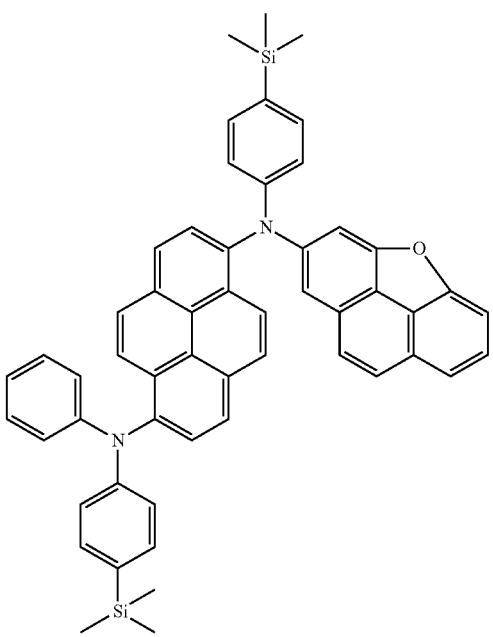
5
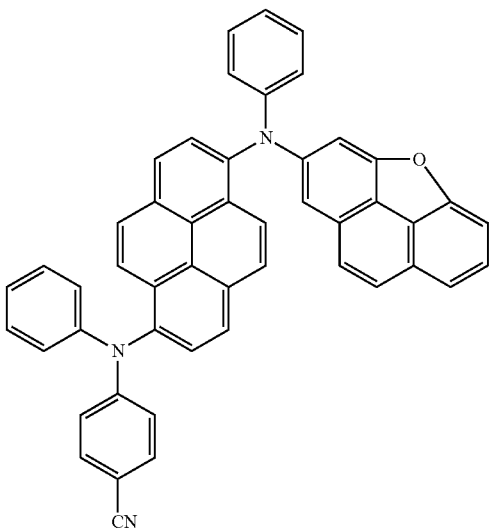

6
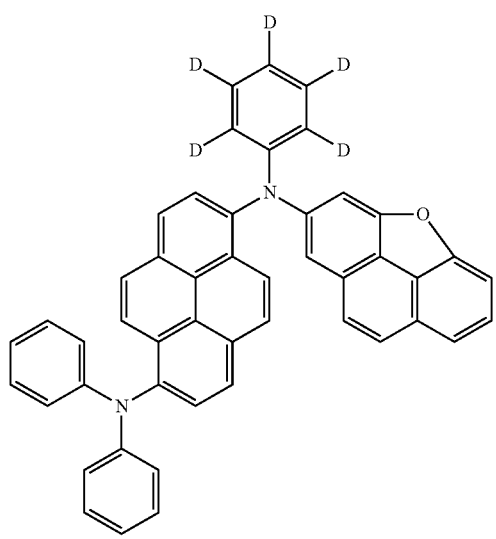
7
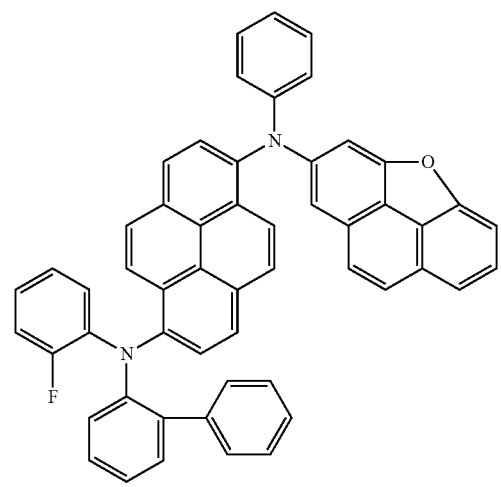
8
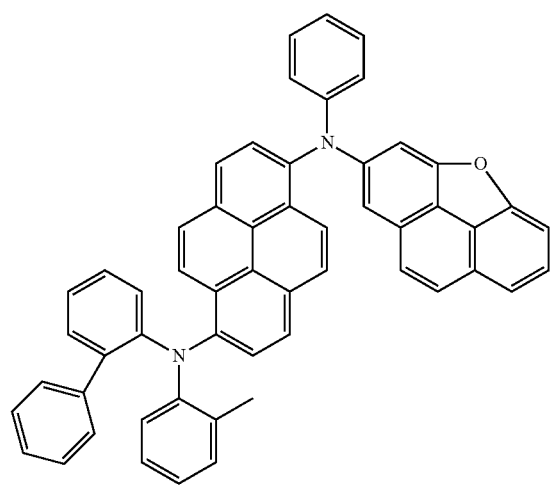
9
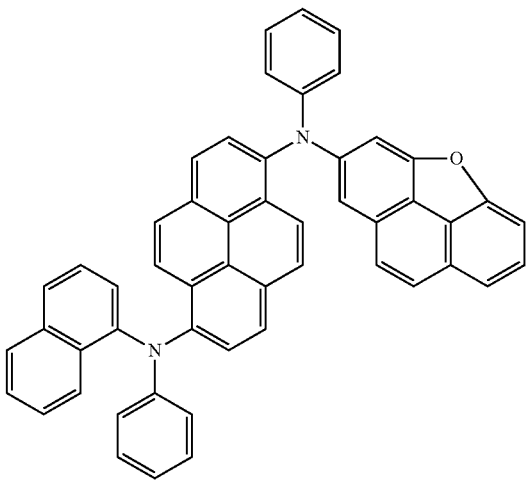
10
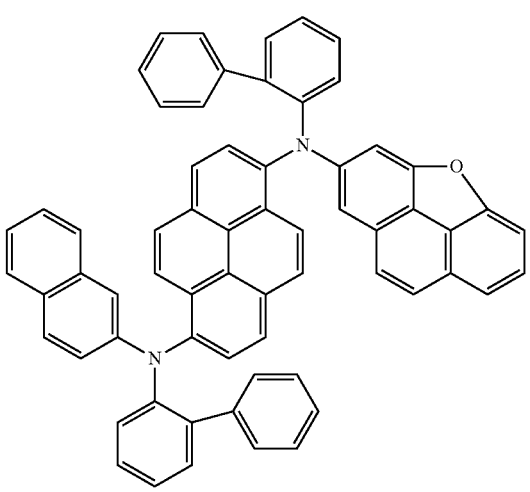
11
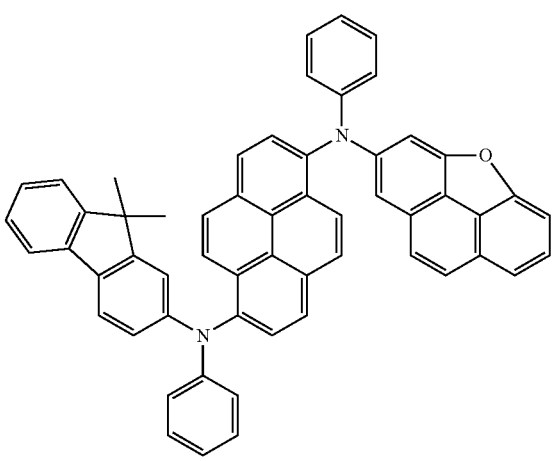

12
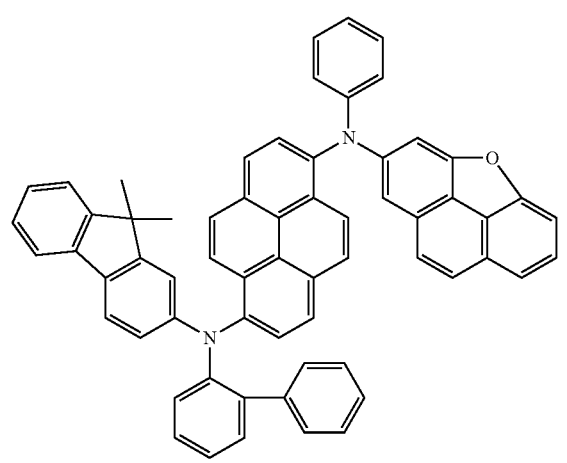
13
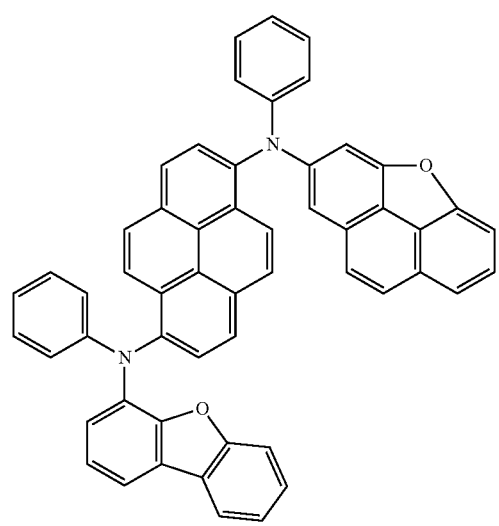
14
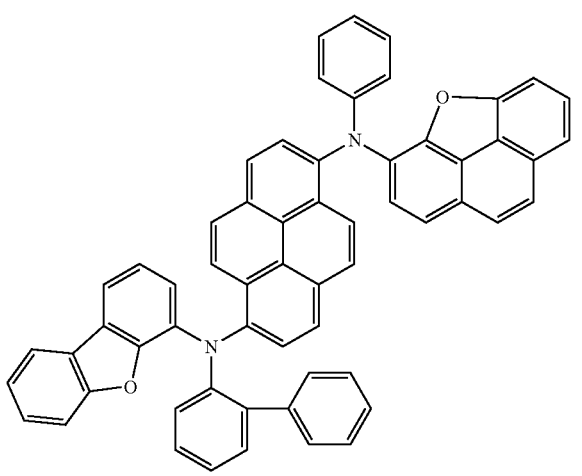
15
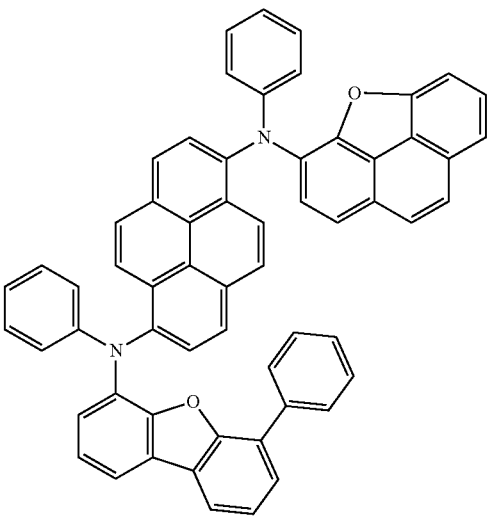
16
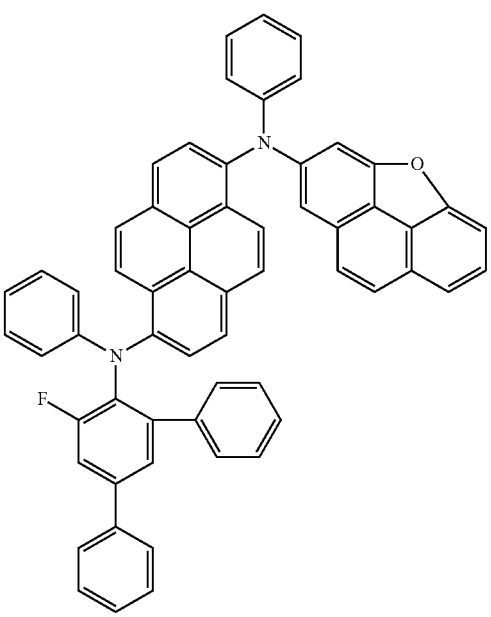
17
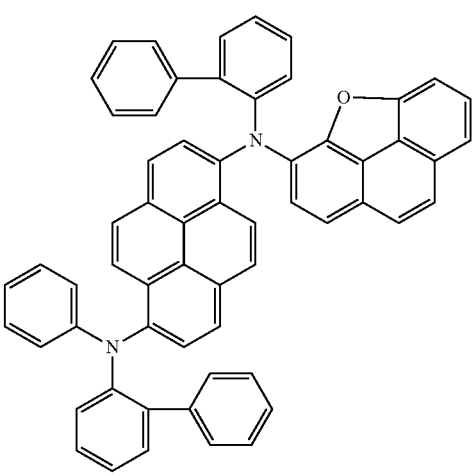

18
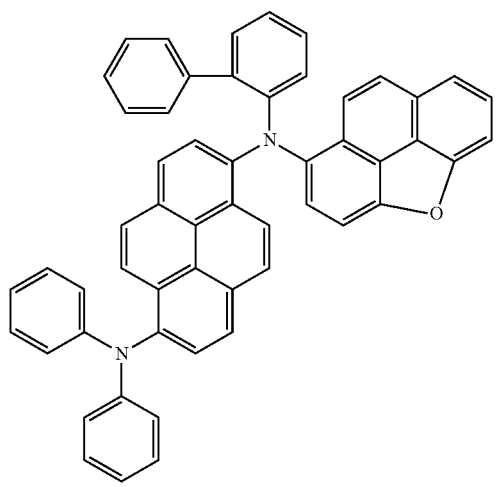
19
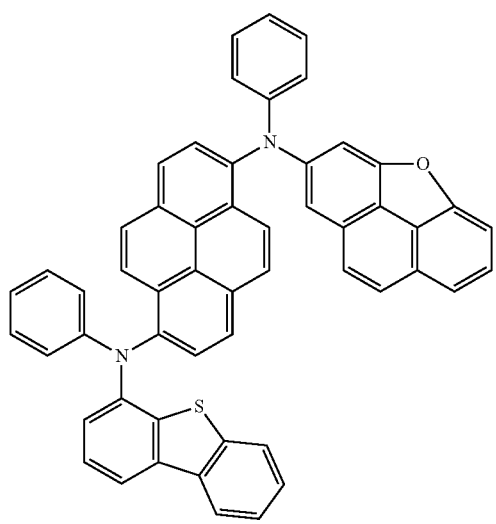
20
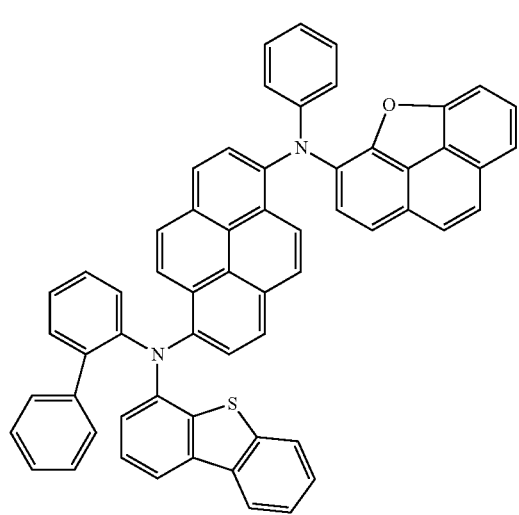
21
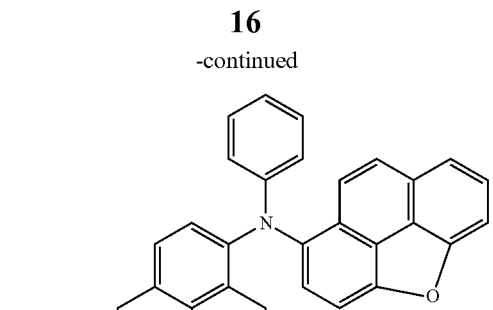
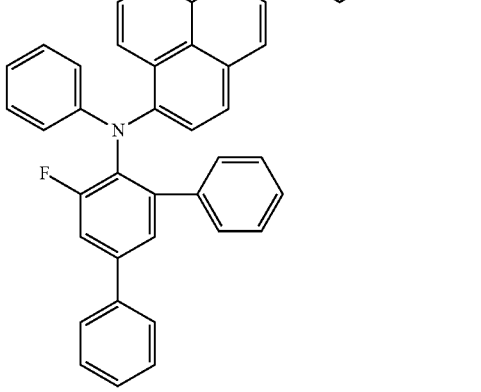
22
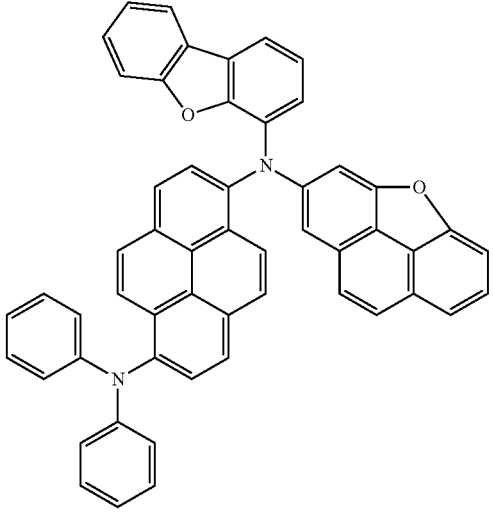
23
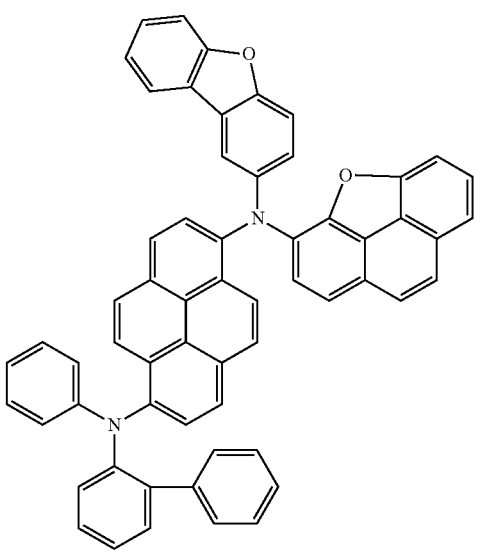

24
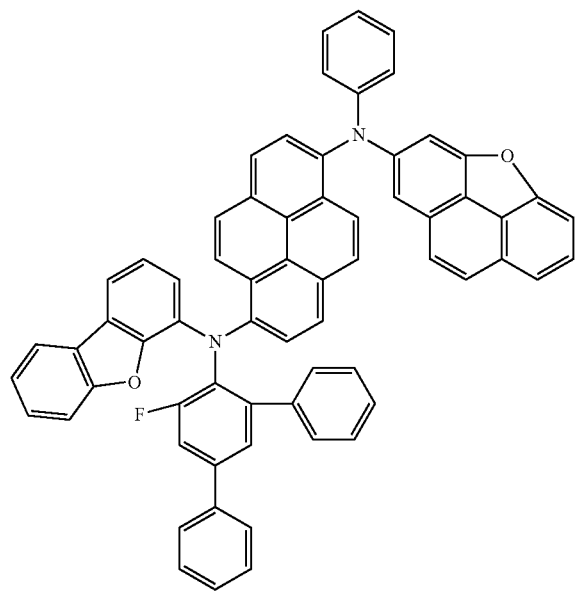
27
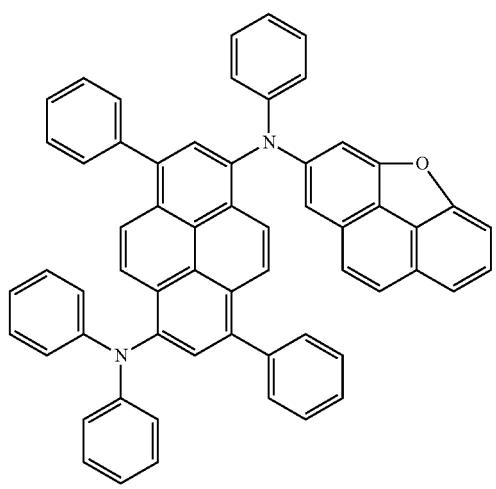
25
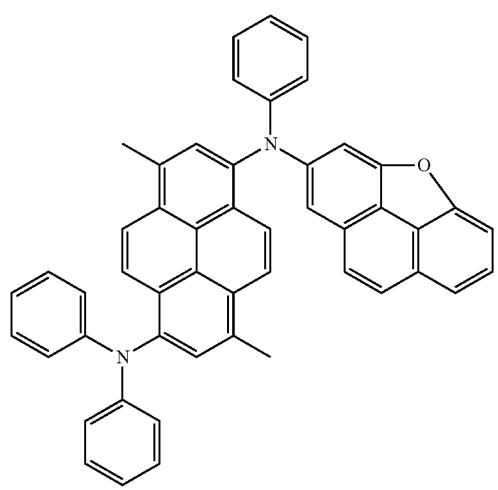
28
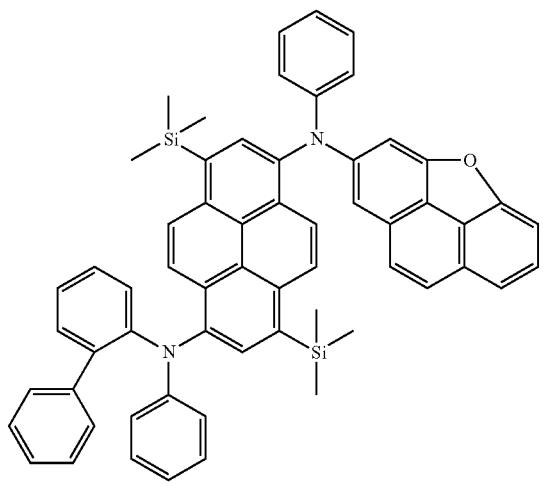
26
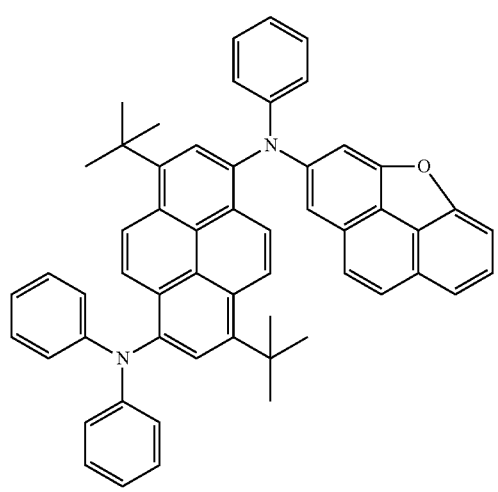
29
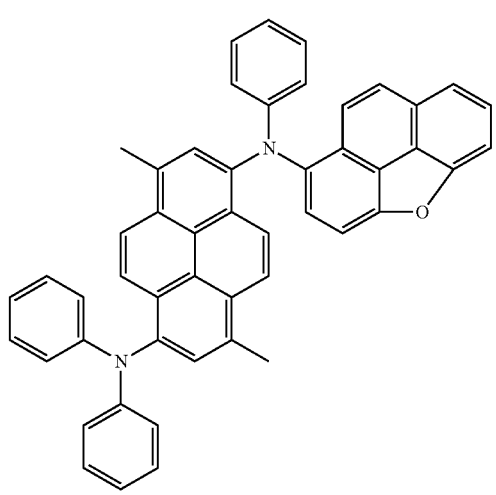

30
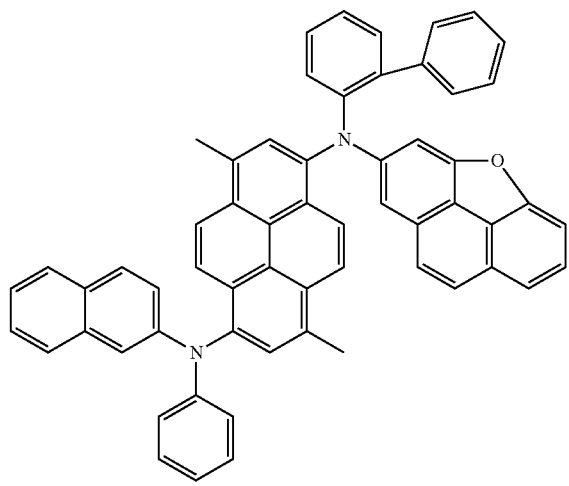
31
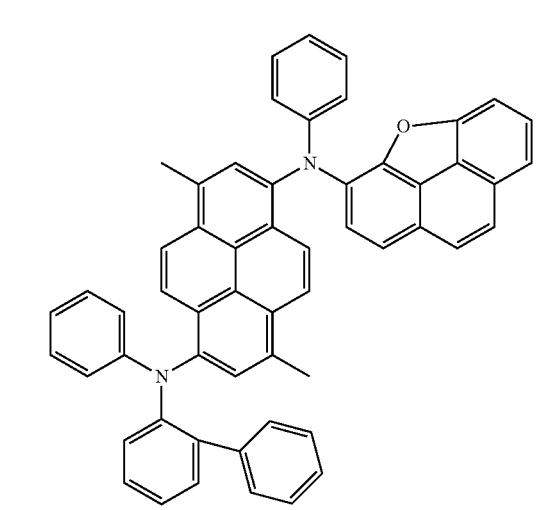
32
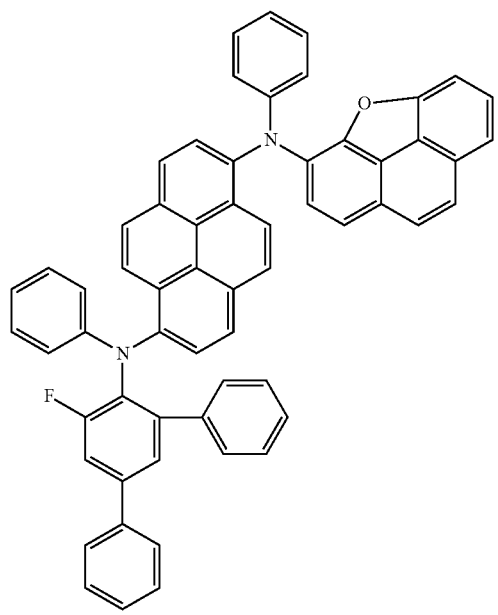
33
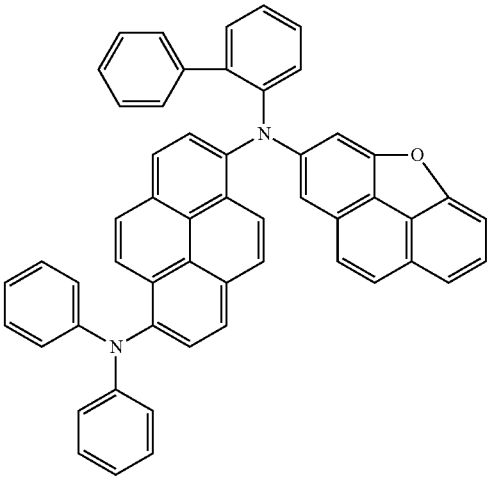
34
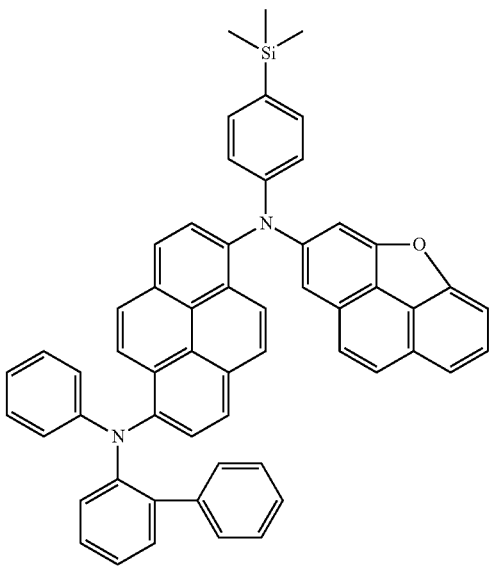
35
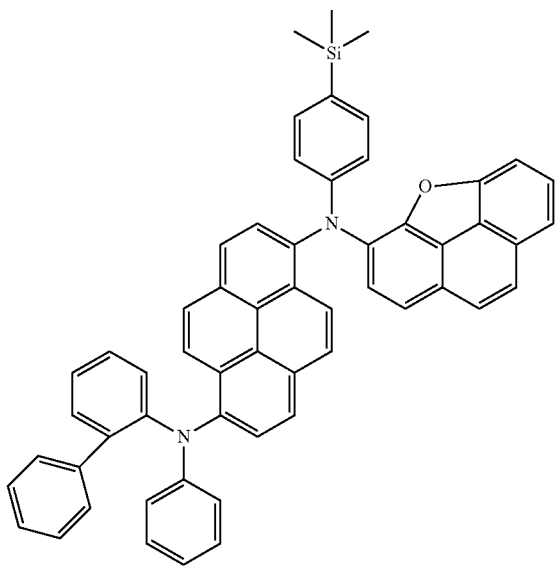

36
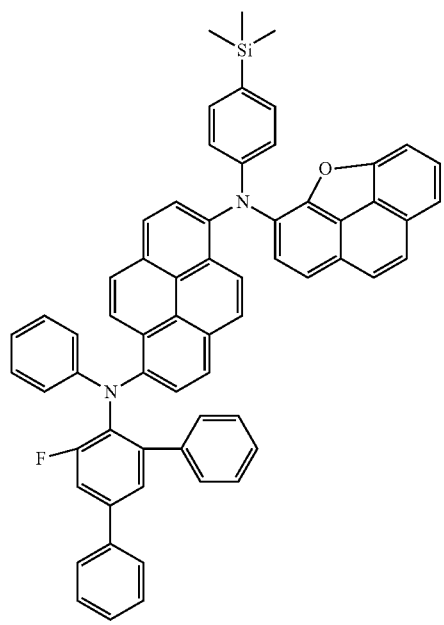
38
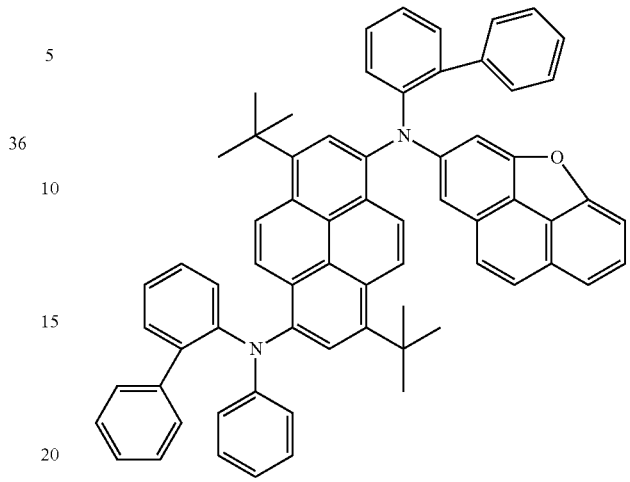
39
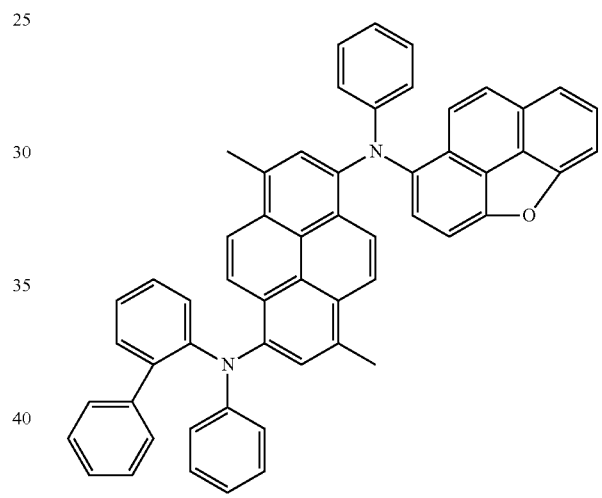
37
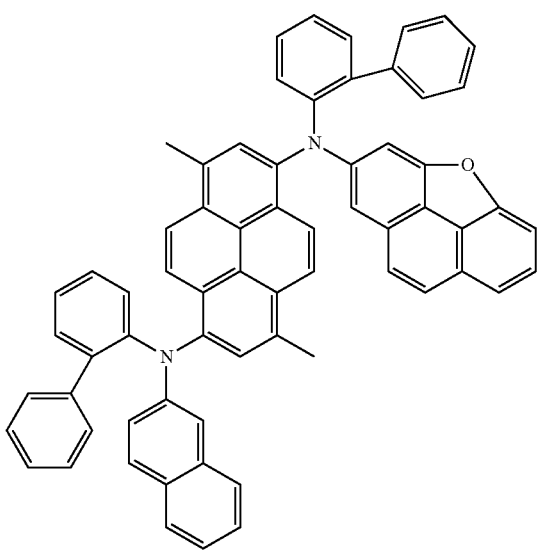
40
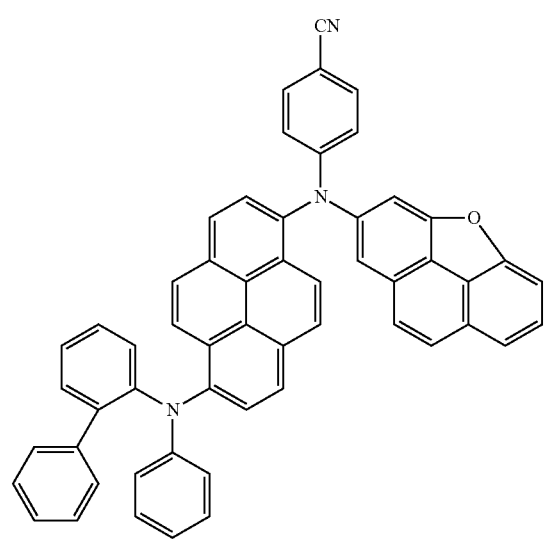

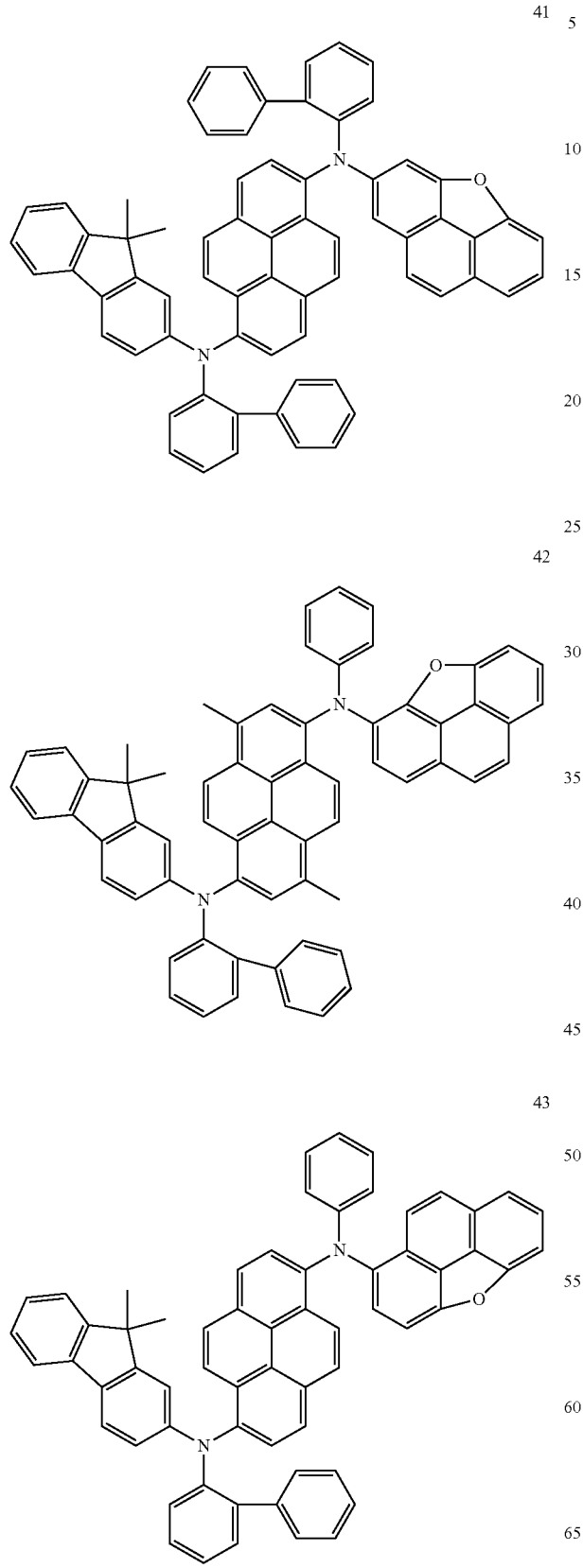
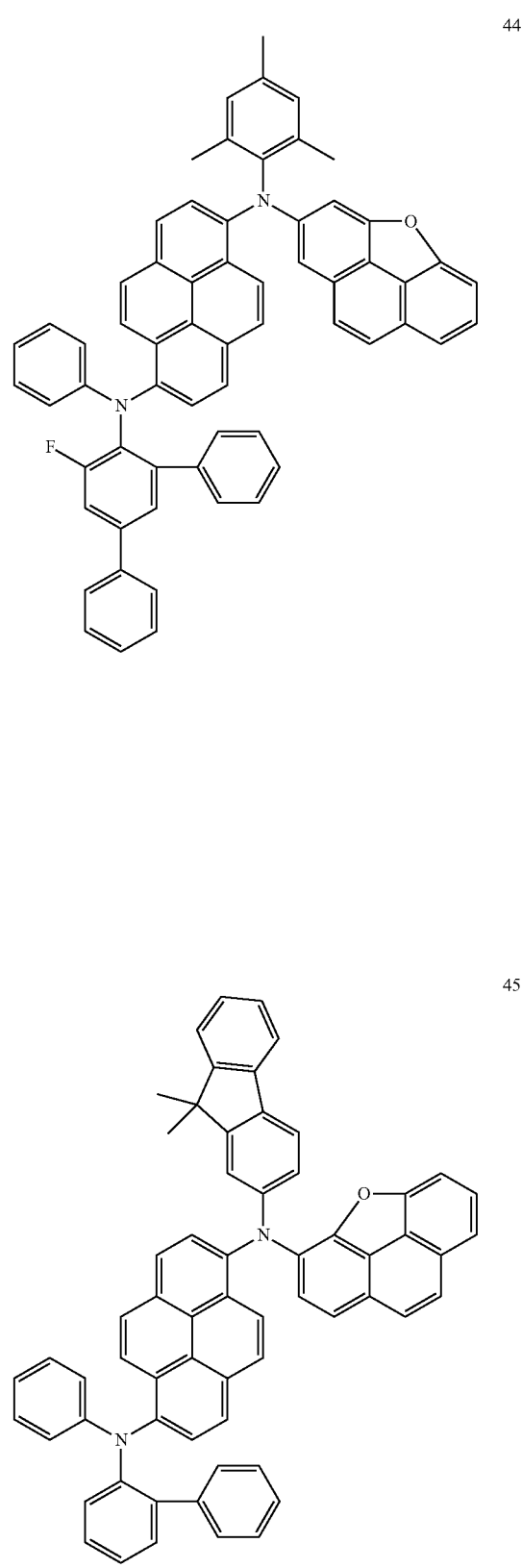

46
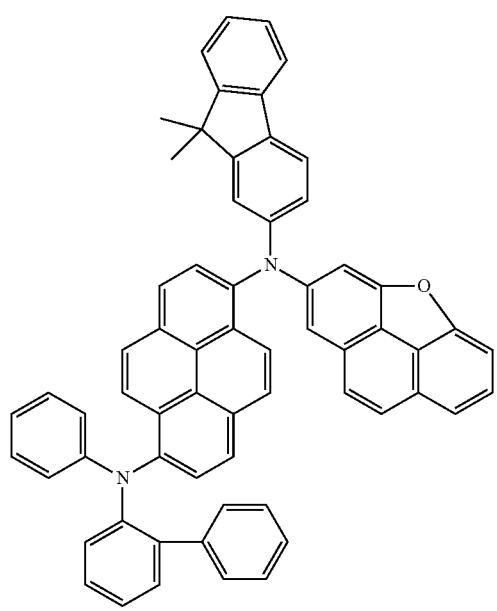
47
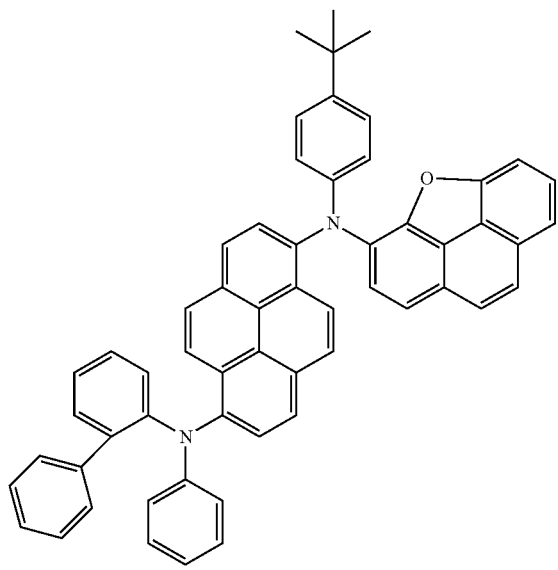
48
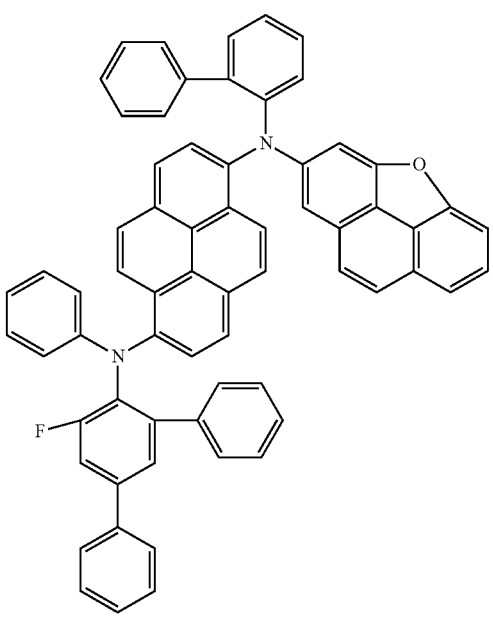
49
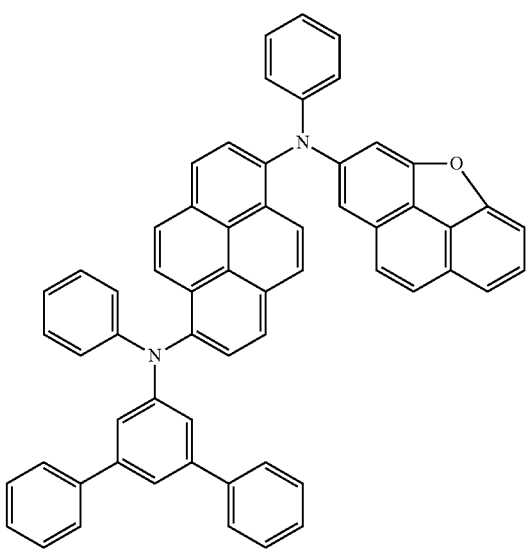

50
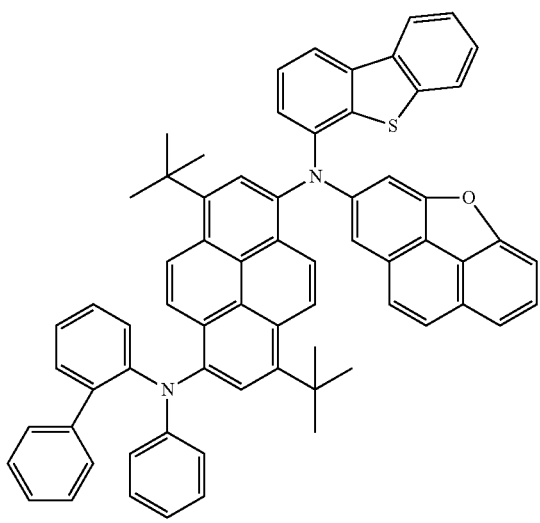
51
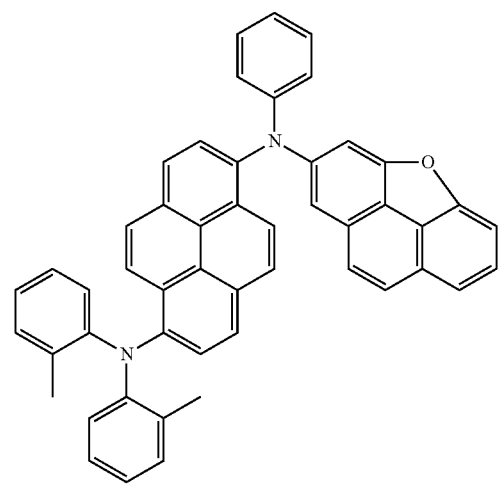
52
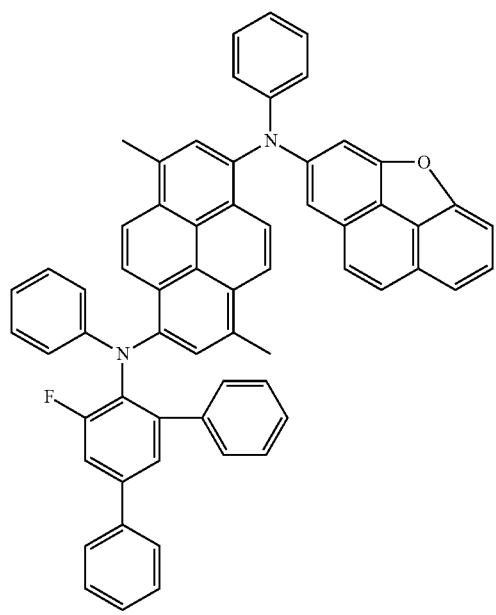
53
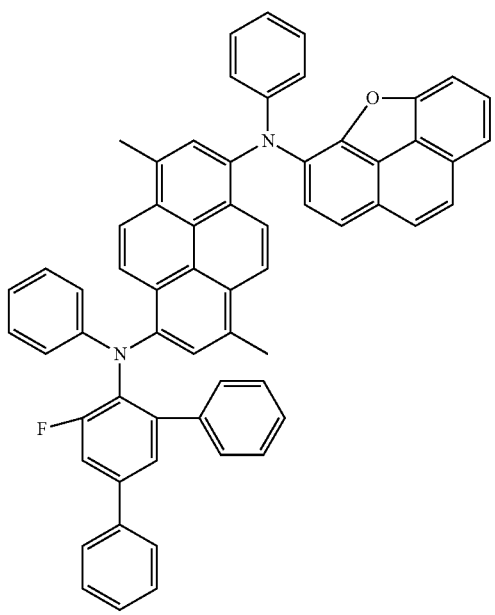
54
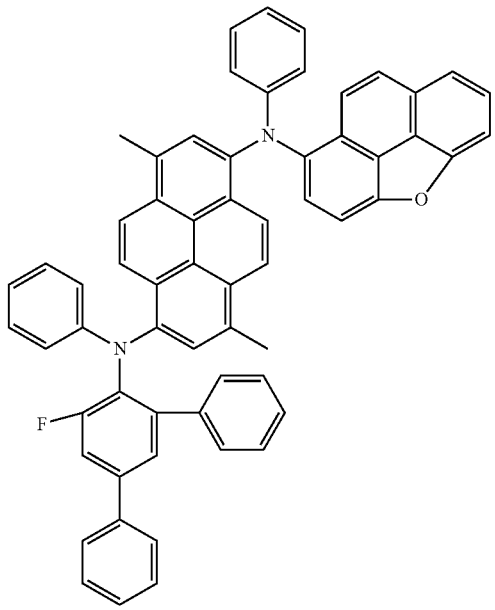

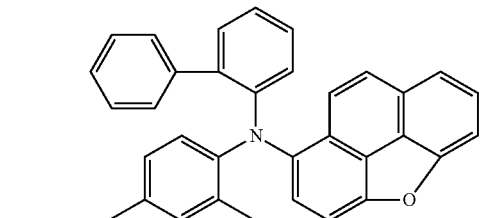
57
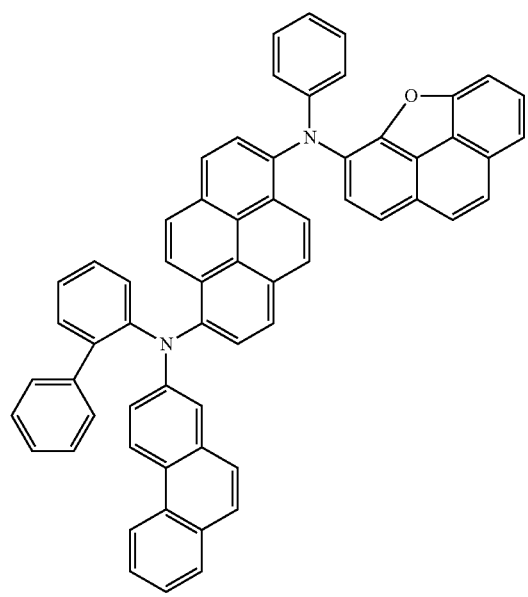
55
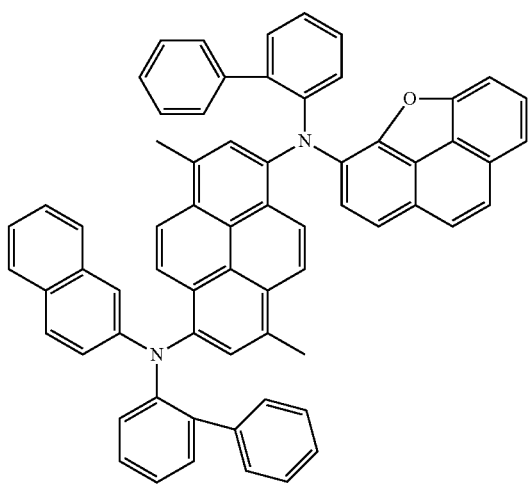
58
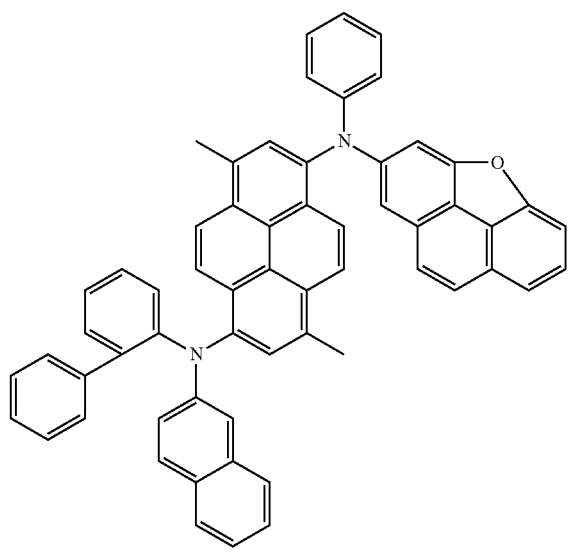
56
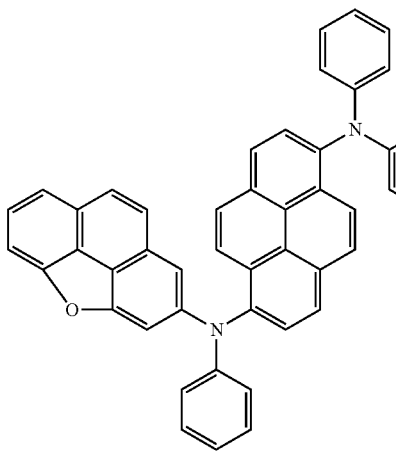
59

31
-continued
60
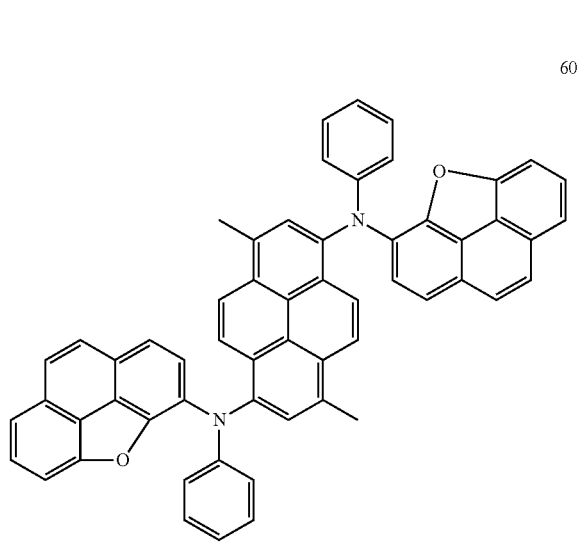
61
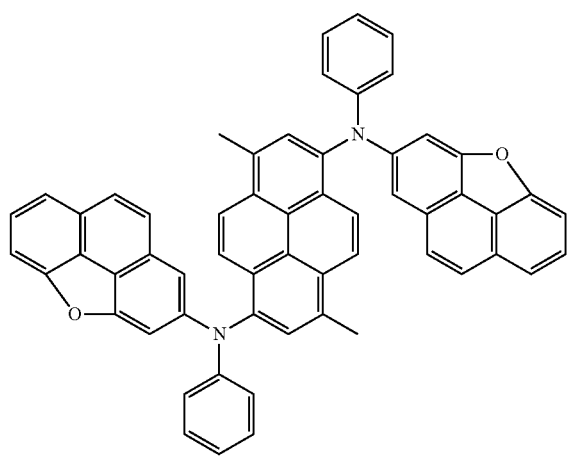
62
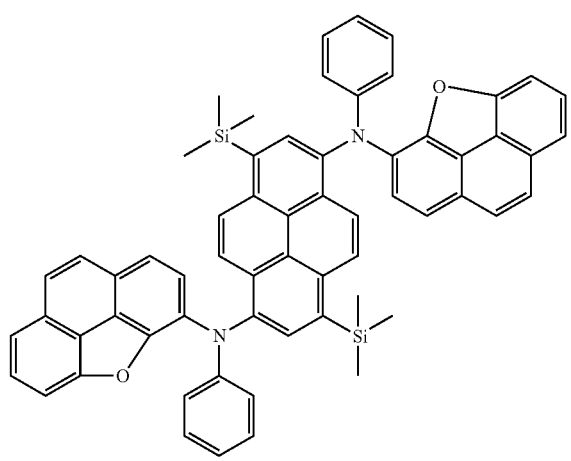
32
-continued
63
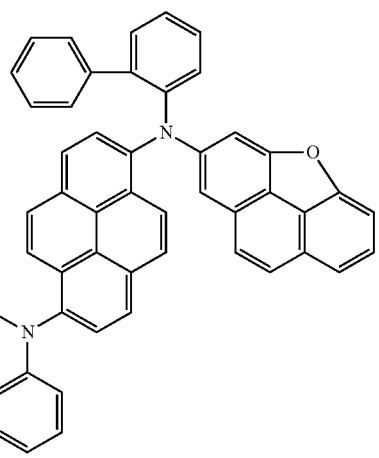
64
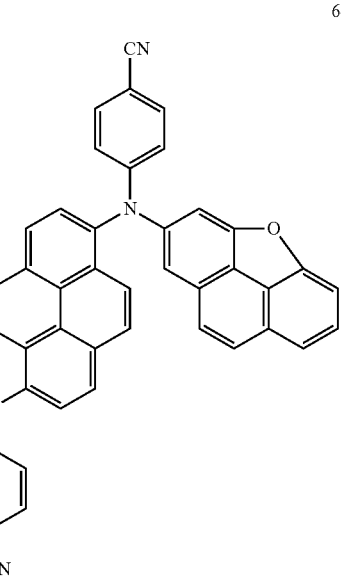
65
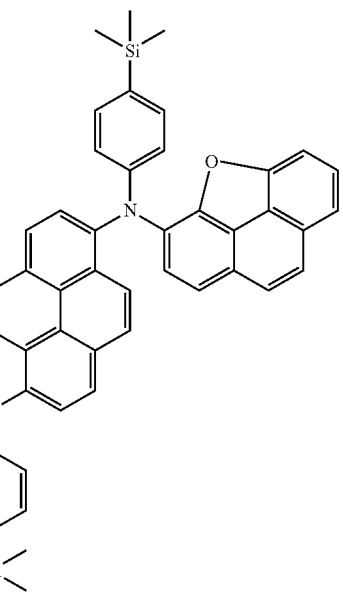

66
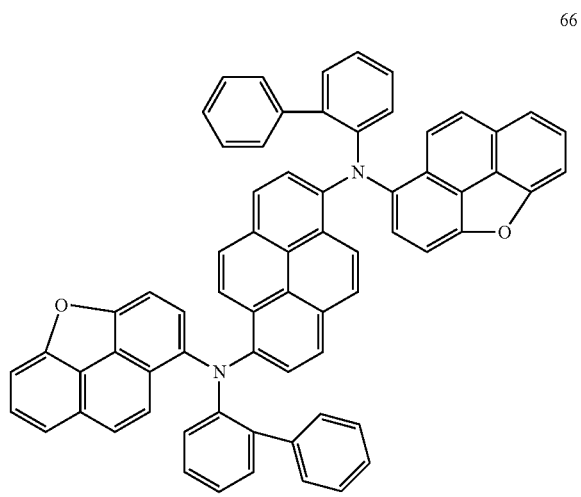
69
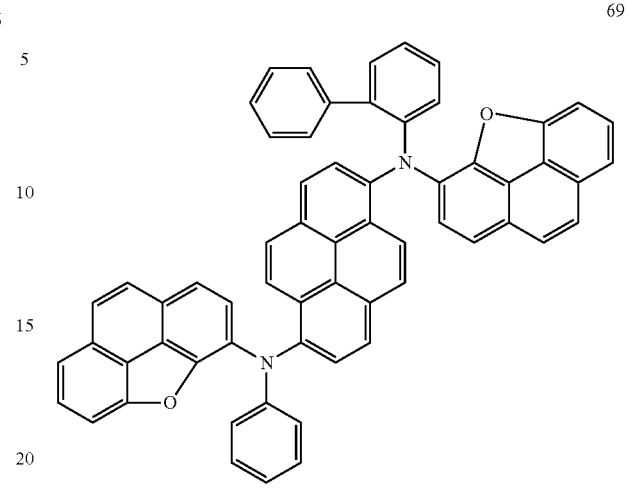
67
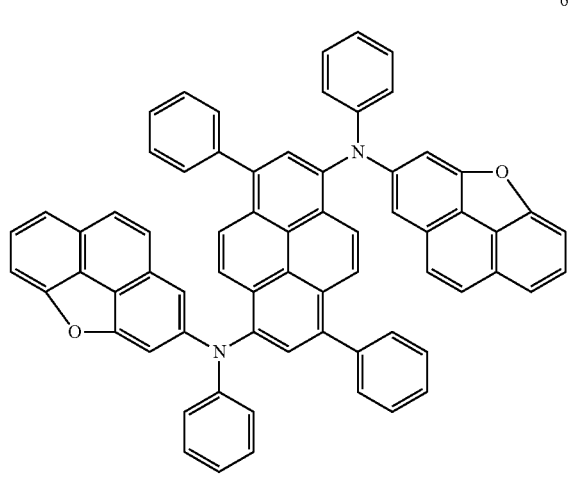
70
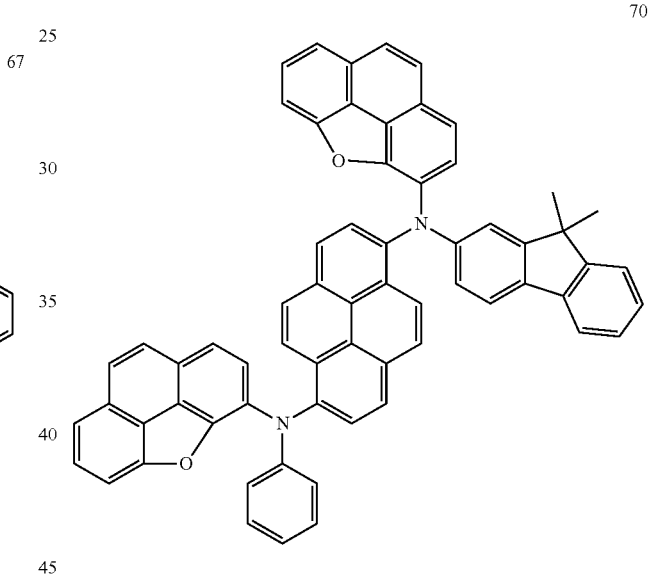
68
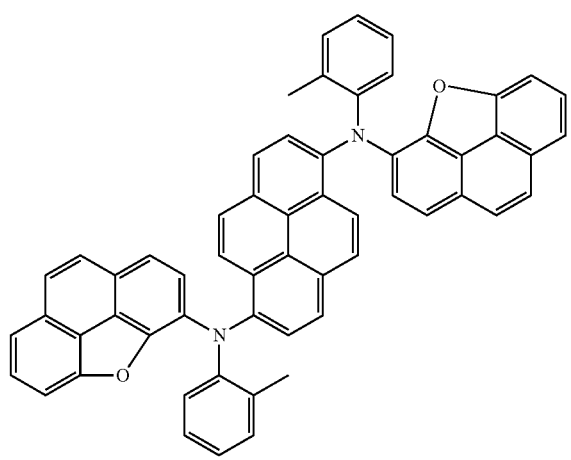
71
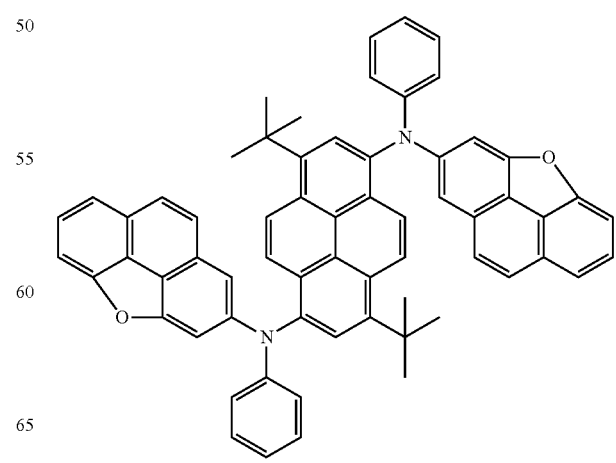

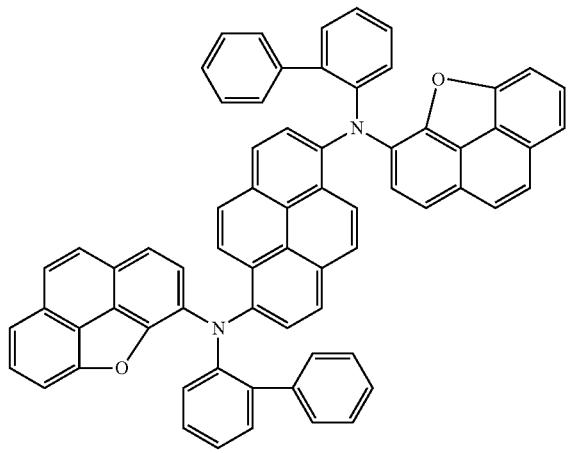

72

According to some exemplary embodiments, an organic light-emitting device may include, a first electrode; a second electrode; and an organic layer between the first electrode and the second electrode, wherein the organic layer includes an emission layer and the compound represented by Formula 1.

In some embodiments, the first electrode is an anode, the second electrode is a cathode, and the organic layer may include i) a hole-transport region between the first electrode and the emission layer, the hole-transport region including at least one selected from a hole injection layer, a hole-transport layer, and an electron blocking layer and ii) an electron transport region between the emission layer and the second electrode, the electron transport region including at least one selected from a hole blocking layer, an electron transport layer, and an electron injection layer.

According to some embodiments, the emission layer may include the compound according to one or more embodiments of the present invention. When the emission layer includes the compound, the compound may serve as a dopant.

As used herein, the term "organic layer" refers to a single layer and/or a plurality of layers disposed between the first electrode and the second electrode in an organic light-emitting device.

The drawing is a schematic view of an organic light-emitting device 10 according to one or more embodiments of the present invention. The organic light-emitting device 10 includes a first electrode 110, an organic layer 150, and a second electrode 190.

Hereinafter, a structure and a method of manufacturing the organic light-emitting device according to some embodiments will be described with reference to the drawing.

Referring to the drawing, a substrate may be additionally positioned under the first electrode 110 or on the second electrode 190. The substrate may be a glass substrate or transparent plastic substrate, each with excellent mechanical strength, thermal stability, transparency, surface smoothness, ease of handling, and water resistance.

The first electrode 110 may be formed by depositing or sputtering a material for forming the first electrode on the substrate. When the first electrode 110 is an anode, the material for the first electrode may be selected from materials with a high work function such that the holes may be easily injected. The first electrode 110 may be a reflective electrode, a semi-transmissive electrode, or a transmissive electrode. The material for the first electrode may be a transparent and highly conductive material, and non-limiting examples of such material include indium tin oxide (ITO), indium zinc oxide (IZO), tin oxide ($SnO_2$), and zinc oxide (ZnO). When the first electrode 110 is a semi-transmissive electrode or a reflective electrode, as a material for forming the first electrode, at least one selected from magnesium (Mg), aluminum (Al), aluminum-lithium (Al—Li), calcium (Ca), magnesium-indium (Mg—In), and magnesium-silver (Mg—Ag) may be used (utilized).

The first electrode 110 may have a single-layer structure, or a multi-layer structure including a plurality of layers. For example, the first electrode 110 may have a triple-layer structure of ITO/Ag/ITO, but embodiments of the present invention are not limited thereto.

The organic layer 150 is disposed on the first electrode 110. The organic layer 150 may include an emission layer.

The organic layer 150 may further include a hole transport region between the first electrode and the emission layer, and an electron transport region between the emission layer and the second electrode.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL), but embodiments of the present invention are not limited thereto.

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, where the layers of each structure are sequentially stacked from the first electrode 110 in the stated order, but embodiments of the present invention are not limited thereto.

When the hole transport region includes a hole injection layer, the hole injection layer may be formed on the first electrode 110 by using (utilizing) one or more suitable methods, such as vacuum-deposition, spin coating, casting, Langmuir-Blodgett (LB) method, ink-jet printing, laser-printing, and/or laser-induced thermal imaging (LITI).

When the hole injection layer is formed by vacuum-deposition, for example, the vacuum-deposition may be performed at a deposition temperature of about 100° C. to about 500° C., at a vacuum degree of about $10^{-8}$ Torr to about $10^{-3}$ Torr, and at a vacuum-deposition rate in a range of about 0.01 Å/sec to about 100 Å/sec, depending on the compound for forming the hole injection layer, and the structure of the hole injection layer to be formed.

When a hole injection layer is formed by spin coating, the spin coating may be performed at a coating rate of about 2000 rpm to about 5000 rpm, and at a temperature of about 80° C. to 200° C., depending on the compound for forming the hole injection layer, and the structure of the hole injection layer to be formed.

When the hole transport region includes a hole transport layer, the hole transport layer may be formed on the first electrode 110 or the hole injection layer by using one or more suitable methods, such as vacuum-deposition, spin coating, casting, LB method, ink-jet printing, laser-printing, and/or LITI. When the hole transport layer is formed by vacuum-deposition and/or spin coating, conditions for vacuum-deposition and coating may be similar to to the above-described vacuum-deposition and coating conditions for forming the hole injection layer.

The hole transport region may include at least one selected from m-MTDATA, TDATA, 2-TNATA, NPB, β-NPB, TPD, a spiro-TPD, a spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), (polyaniline)/poly(4-styrenesulfonate) (PANI/PSS), a compound represented by Formula 201 below, and a compound represented by Formula 202 below:

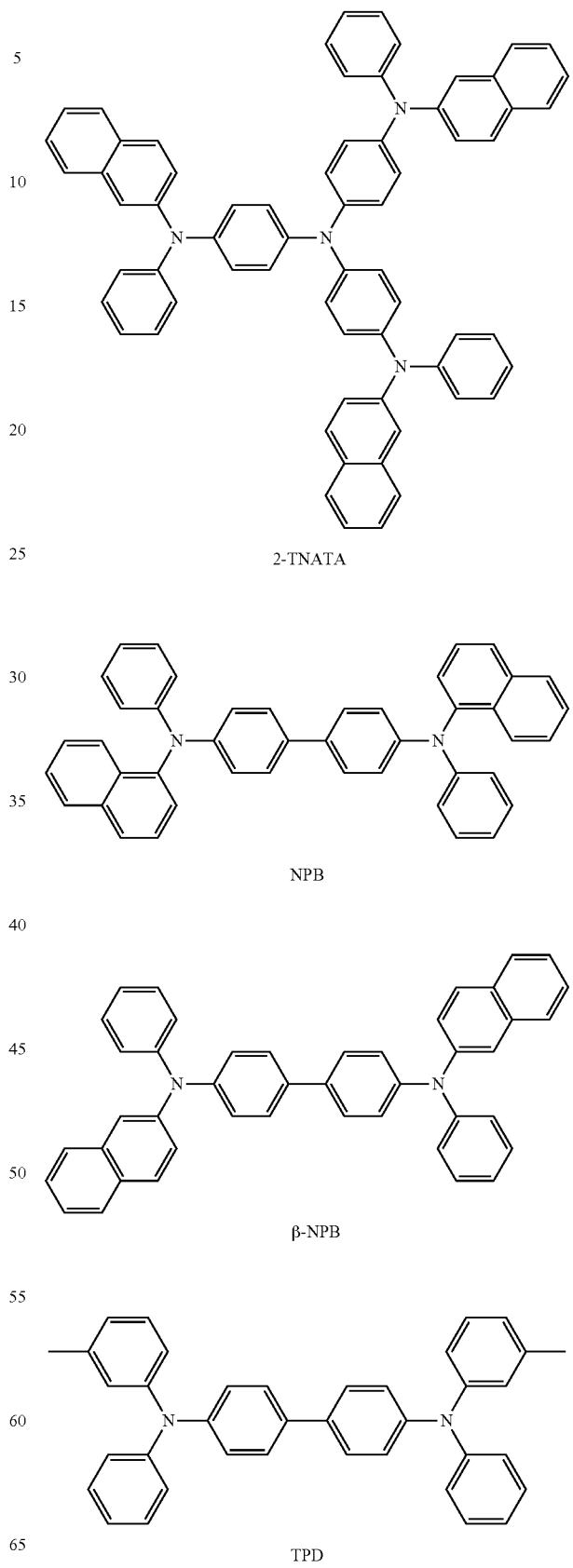

m-MTDATA

TDATA

2-TNATA

NPB

β-NPB

TPD

-continued

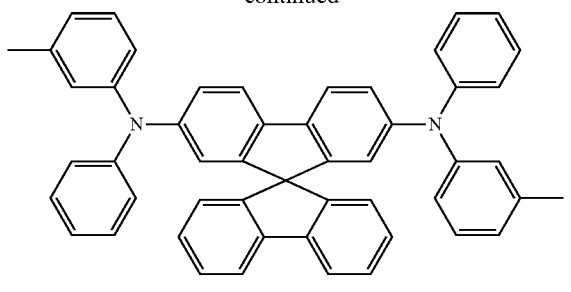
Spiro-TPD

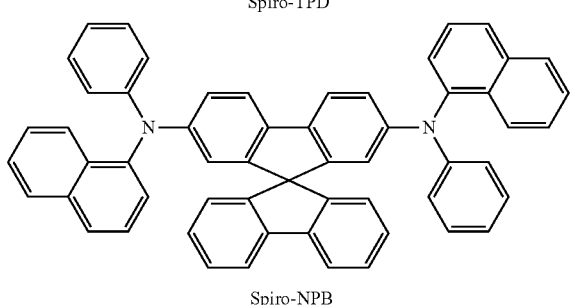
Spiro-NPB

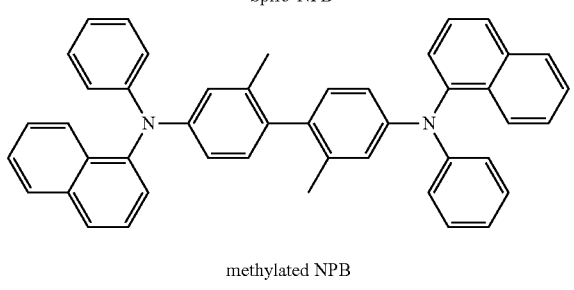
methylated NPB

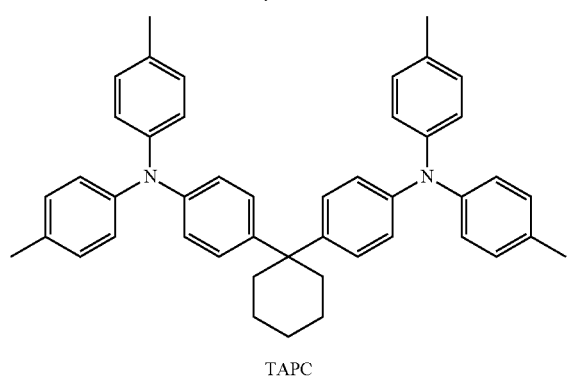
TAPC

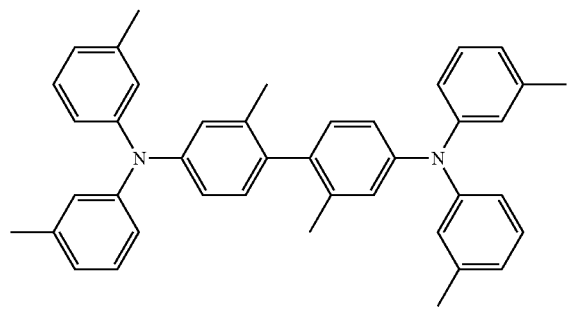
HMTPD

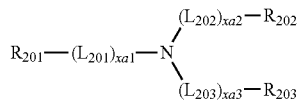
Formula 201

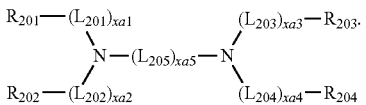
Formula 202

In Formulae 201 and 202, $L_{201}$ and $L_{205}$ may be each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xa1 to xa4 may be each independently selected from 0, 1, 2, and 3; and xa5 may be selected from 1, 2, 3, 4, and 5;

$R_{201}$ to $R_{204}$ may be each independently selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formulae 201 and 202, $L_{201}$ to $L_{205}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently selected from 0, 1, and 2;

xa5 may be selected from 1, 2, and 3;

$R_{201}$ to $R_{204}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; but embodiments of the present invention are not limited thereto.

The compound represented by Formula 201 may be represented by Formula 201A:

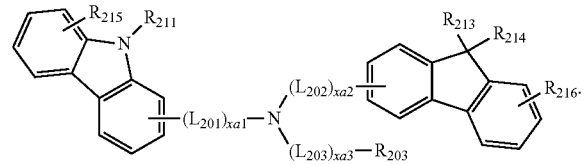

Formula 201A

In some embodiments, the compound represented by Formula 201 may be represented by Formula 201A-1, but embodiments of the present invention are not limited thereto:

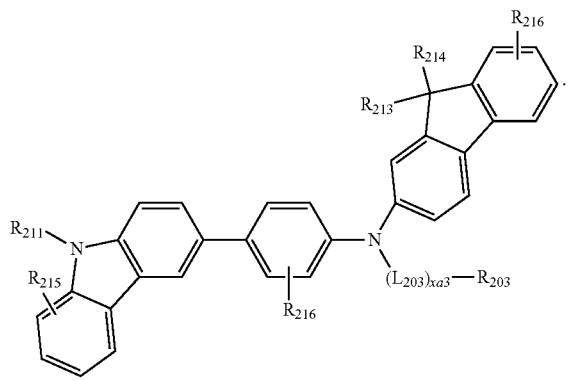

Formula 201A-1

In some embodiments, the compound represented by Formula 202 may be represented by Formula 202A, but embodiments of the present invention are not limited thereto:

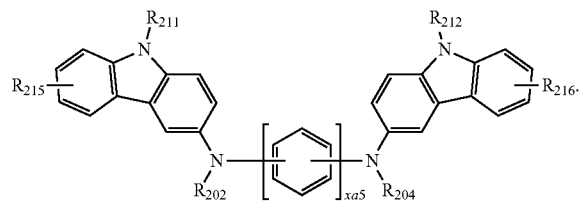

Formula 202A

In Formulae 201A, 201A-1, and 202A, $L_{201}$ to $L_{203}$, xa1 to xa3, xa5, and $R_{202}$ to $R_{204}$ may be understood by referring to the descriptions provided herein, and $R_{211}$ may be the same as defined in connection with $R_{203}$; and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In some embodiments, in Formulae 201A-1 and 202A, $L_{201}$ to $L_{203}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently selected from 0 and 1;

$R_{203}$, $R_{211}$ and $R_{212}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may be each independently selected from:
a $C_1$-$C_{20}$ alkyl group and a $C_1$-$C_{20}$ alkoxy group;
a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may be each independently selected from:
a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

and xa5 may be selected from 1 and 2.

In Formulae 201A and 201A-1, $R_{213}$ and $R_{214}$ may link to each other so as to form a saturated ring or an unsaturated ring.

The compound represented by Formula 201 and the compound represented by Formula 202 may each independently include Compounds HT1 to HT20, but embodiments of the present invention are not limited thereto.

HT1
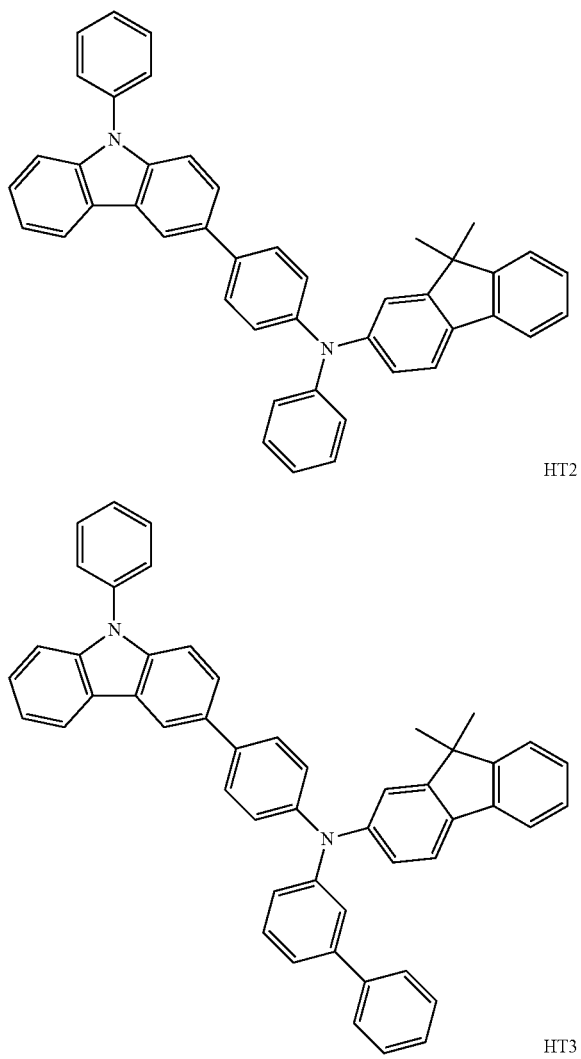
HT2
HT4
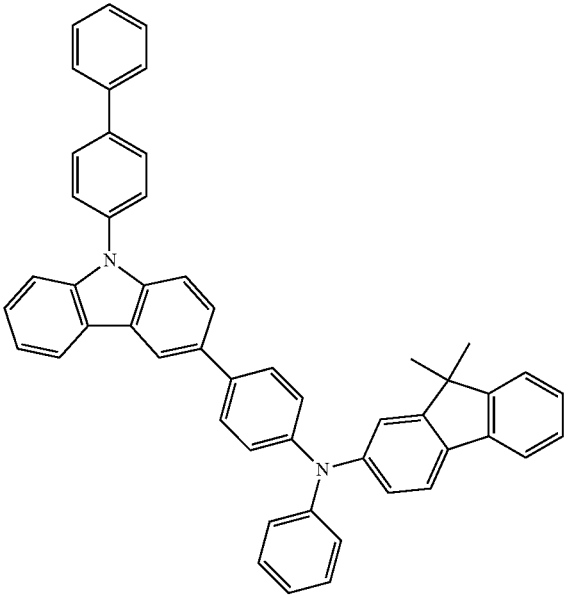
HT3
HT5
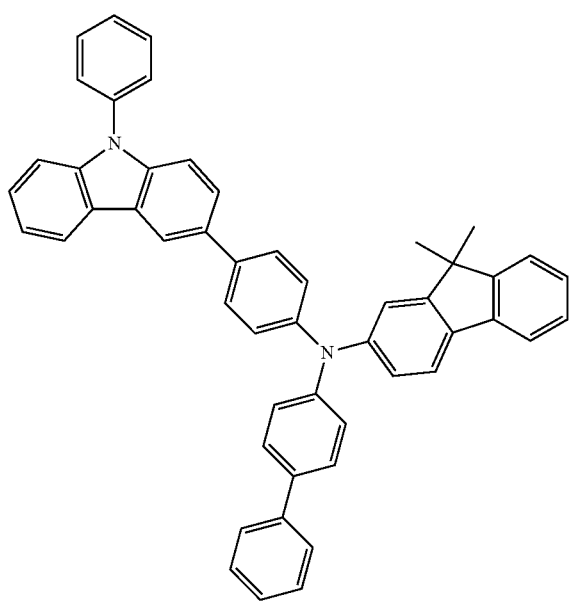
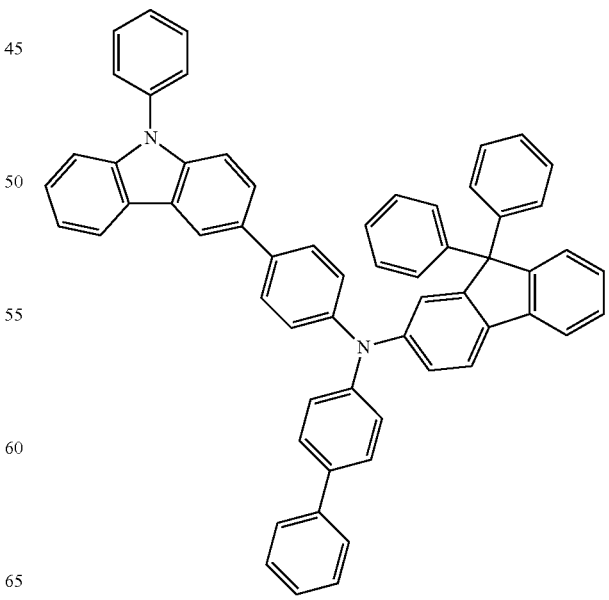

HT6
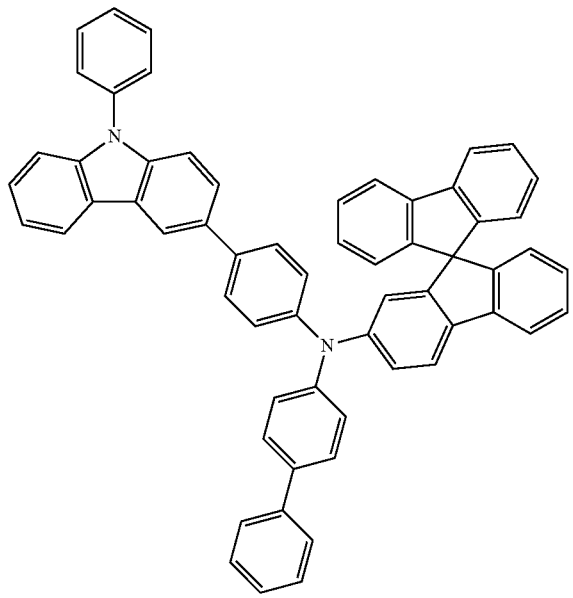
HT7
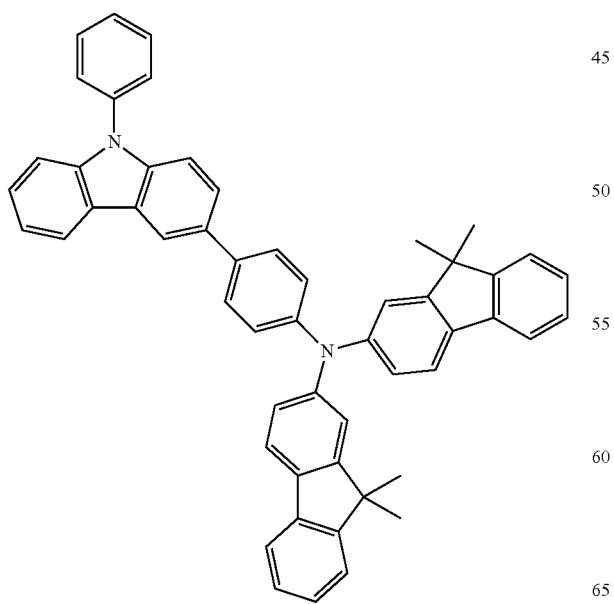
HT8
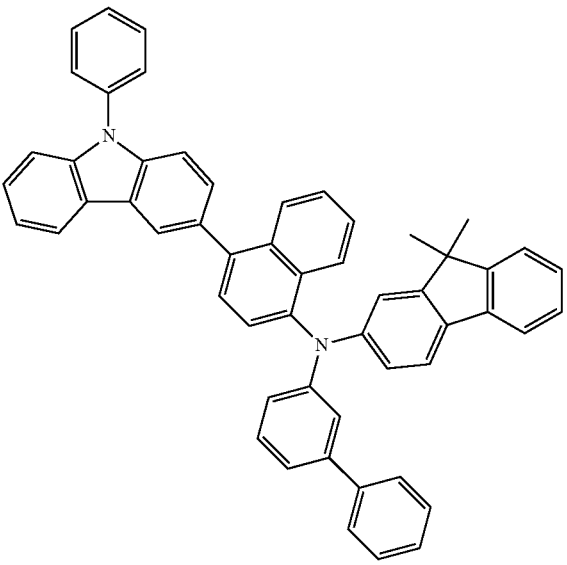
HT9
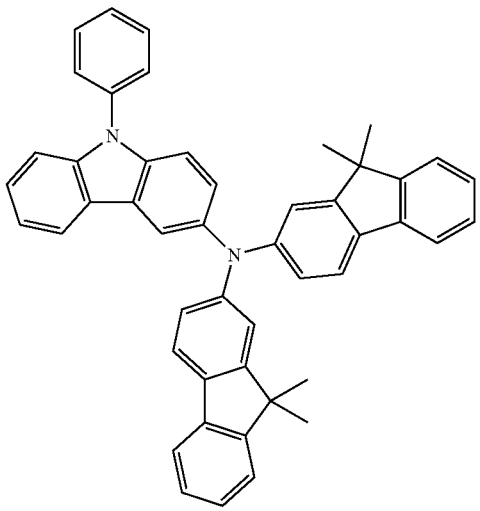

HT10
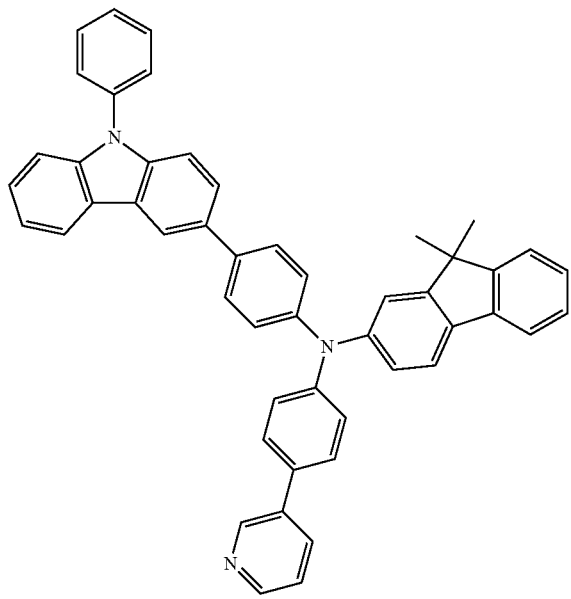
HT11
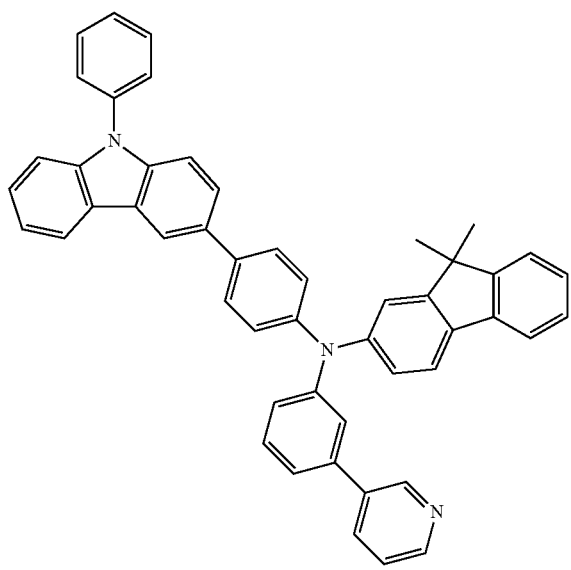
HT12
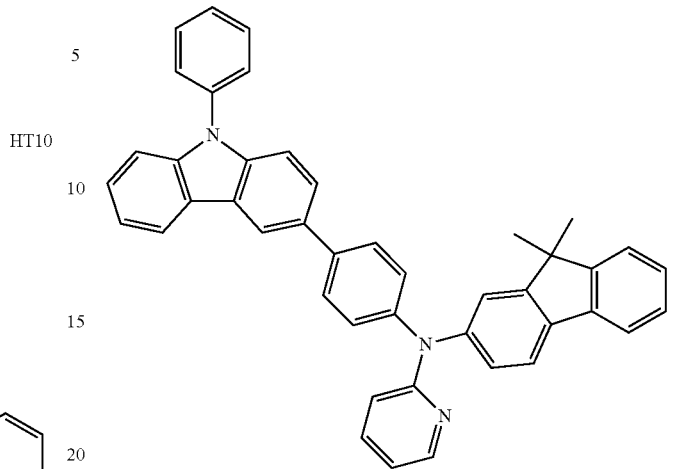
HT13
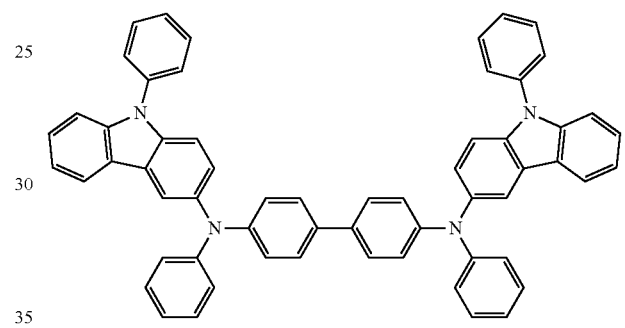
HT14
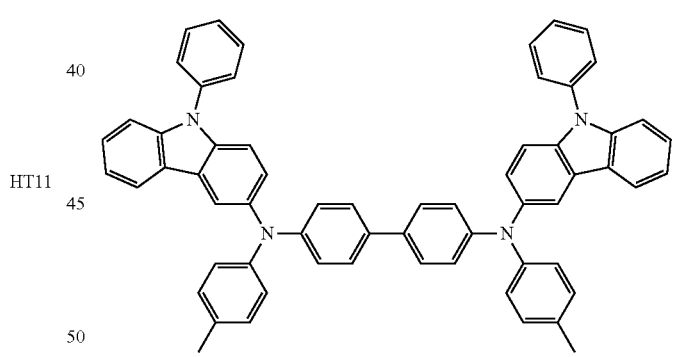
HT15
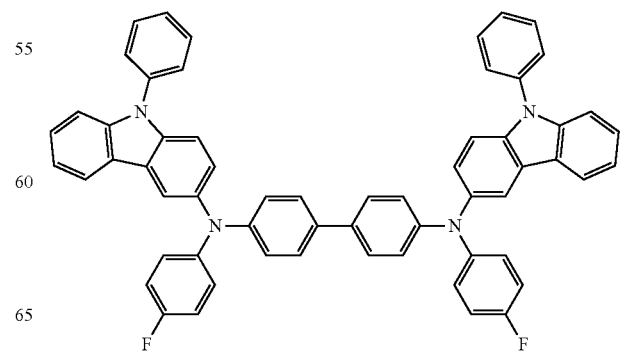

HT16 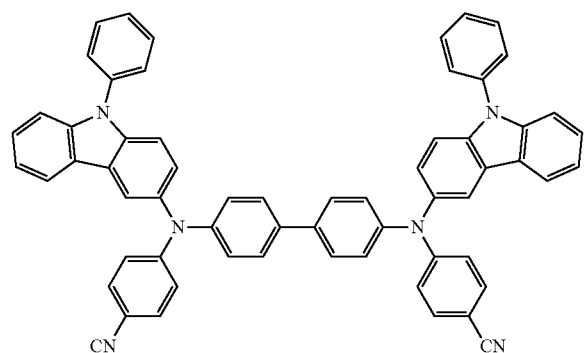

HT17 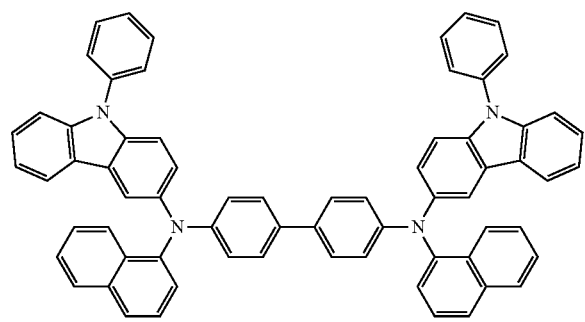

HT18 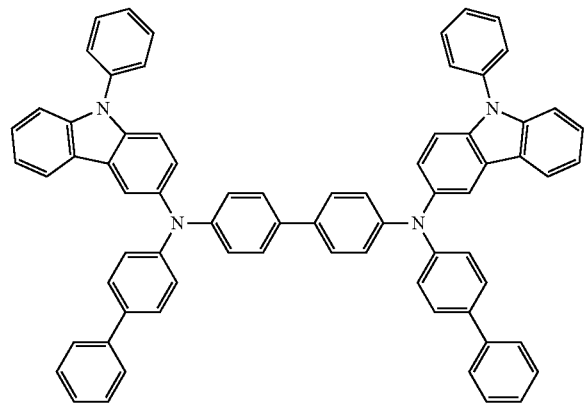

HT19 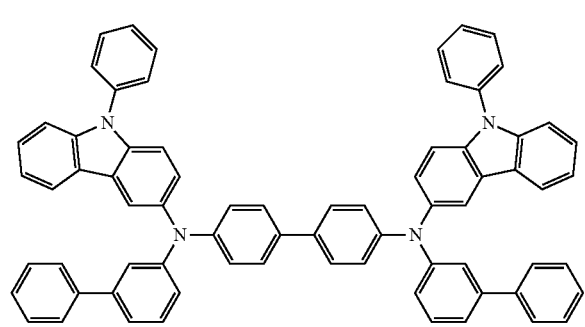

HT20 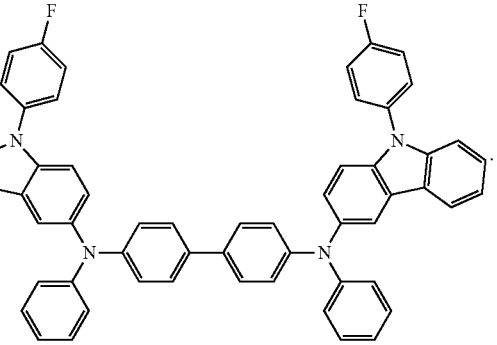

A thickness of the hole transport region may be in a range of about 100 Å to about 10,000 Å, for example, about 100 Å to about 1000 Å. When the hole transport region includes a hole injection layer and a hole transport layer, the thickness of the hole injection layer may be in a range of about 100 Å to about 10,000 Å, for example, about 100 Å to about 9,950 Å, or about 100 Å to about 1000 Å, and the thickness of the hole transport layer may be in a range of about 50 Å to about 2000 Å, and for example, about 100 Å to about 1500 Å. When the thicknesses of the hole transport region, the hole injection layer, and the hole transport layer are within any of these ranges, excellent hole transport characteristics may be obtained without a substantial increase in driving voltage.

The hole transport region may further include, in addition to the materials mentioned above, a charge-generating material to improve conductive properties. The charge-generating material may be homogeneously or non-homogeneously dispersed throughout the hole transport region.

The charge-generating material may be, for example, a p-dopant. The p-dopant may be one selected from a quinone derivative, a metal oxide, and a cyano group-containing compound, but is not limited thereto. Non-limiting examples of the p-dopant include quinone derivatives such as tetra-cyanoquinonedimethane (TCNQ) and/or 2,3,5,6-tetrafluoro-tetracyano-1,4-benzoquinonedimethane (F4-TCNQ); metal oxides such as a tungsten oxide and/or a molybdenum oxide; and Compound HT-D1 illustrated below.

Compound HT-D1

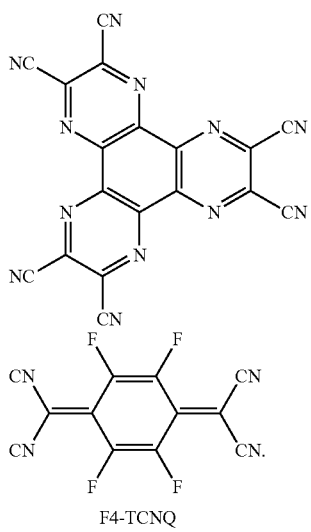

F4-TCNQ

The hole transport region may further include, in addition to the hole injection layer and the hole transport layer, at least one selected from a buffer layer and an electron blocking layer. Since the buffer layer may compensate for an optical resonance distance according to a wavelength of light emitted from the emission layer, light-emission efficiency of the resulting organic light-emitting device may be improved. As a material included in the buffer layer, materials that are included in the hole transport region may be used (utilized). In some embodiments, the electron blocking layer prevents or substantially reduces the injection of electrons from the electron transport region.

An emission layer may be formed on the first electrode 110 or the hole transport region by using one or more suitable methods, such as vacuum-deposition, spin coating, casting, LB method, ink-jet printing, laser-printing, and/or LITI. When the emission layer is formed by vacuum-deposition and/or spin coating, deposition and coating conditions for the emission layer may be similar to the deposition and coating conditions for the hole injection layer.

When the organic light-emitting device 10 is a full color organic light-emitting device, the emission layer may be patterned into a red emission layer, a green emission layer, or a blue emission layer, according to a sub pixel. Alternatively, the emission layer may have a stacked structure of a red emission layer, a green emission layer, and a blue emission layer, or may include a red-light emission material, a green-light emission material, and a blue-light emission material, which are mixed with each other in a single layer, to emit white light.

According to some embodiments, the emission layer may further include a compound represented by Formula 4.

Formula 4

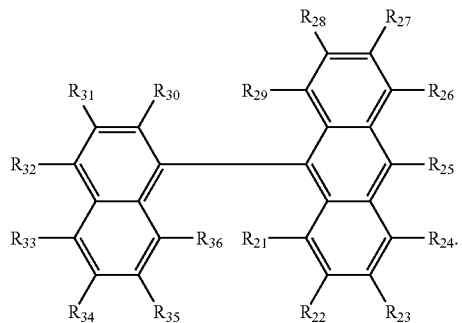

In Formula 4, $R_{21}$ to $R_{36}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

at least one of the substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

where $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In some embodiments, the compound represented by Formula 4 may serve as a host.

In some embodiments, in Formula 4, $R_{25}$, $R_{27}$, $R_{31}$, $R_{32}$, and $R_{33}$ may be each independently selected from a hydrogen, a deuterium, a cyano group, a substituted or unsubstituted $C_1$-$C_{60}$ alkyl group, —Si($Q_3$)($Q_4$)($Q_5$) (where $Q_3$ to $Q_5$ are as defined above), and Formulae 3a to 3c:

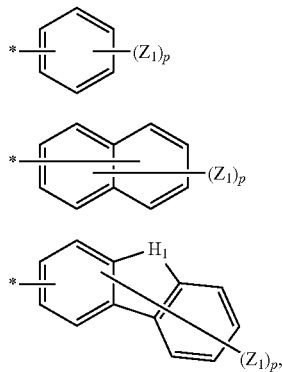

In Formulae 3a to 3c, $Z_1$ may be selected from a hydrogen atom, a deuterium, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ condensed polycyclic group, a halogen group, a cyano group, a nitro group, a hydroxyl group, and a carboxyl group;

$H_1$ may be selected from —O—, —S—, —$CR_{51}R_{52}$—, and —$NR_{53}$—; p may be an integer selected from 1 to 7; and * indicates a binding site;

$R_{51}$ and $R_{53}$ may be the same as defined in connection with $R_{21}$ to $R_{36}$ described above; and optionally, $R_{51}$ and $R_{52}$ may be linked to each other to form a ring.

In some embodiments, in Formula 4, $R_{21}$ to $R_{24}$, $R_{26}$, $R_{28}$ to $R_{30}$, and $R_{34}$ to $R_{36}$ may be each independently selected from a hydrogen and a deuterium.

In some embodiments, the emission layer may include the compound represented by Formula 1 as a fluorescent or phosphorescent dopant and the compound represented by Formula 4 as a fluorescent or phosphorescent host.

The compound represented by Formula 4 may be, for example, represented by any one of compounds below, but is not limited thereto:

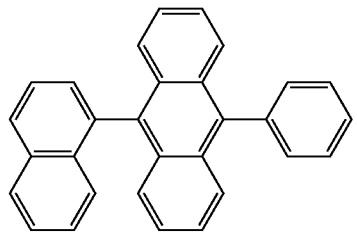
H1

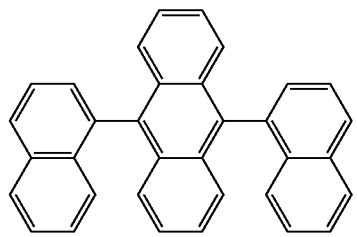
H2

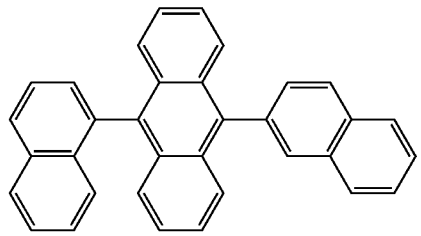
H3

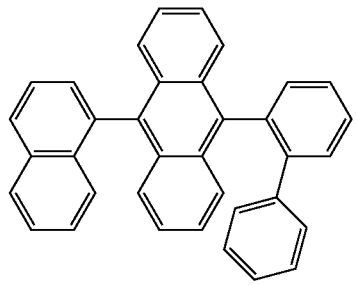
H4

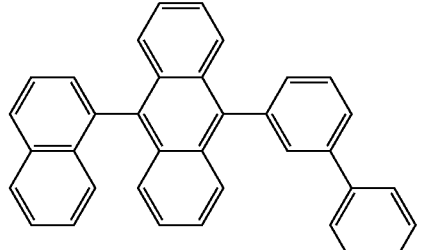
H5

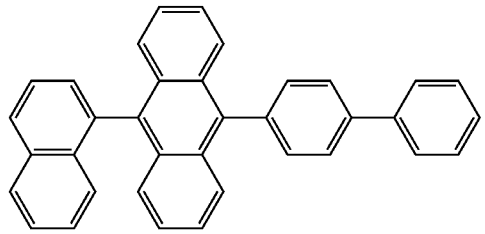
H6

H7
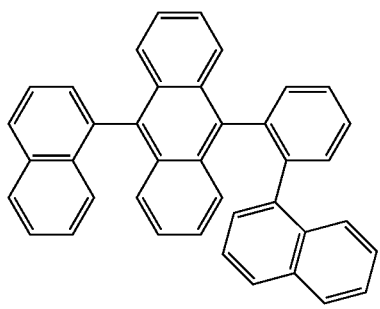
H8
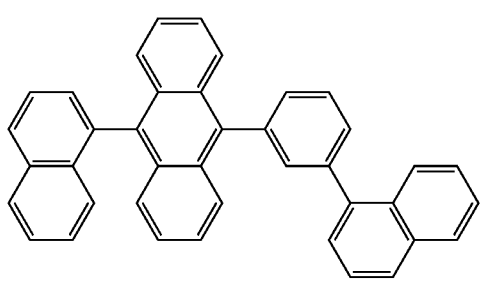
H9
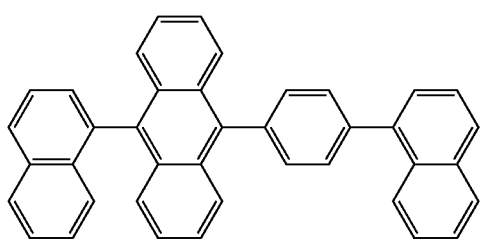
H10
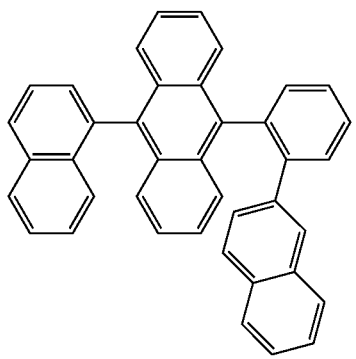
H11
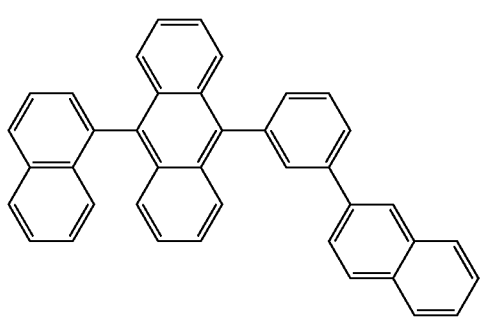
H12
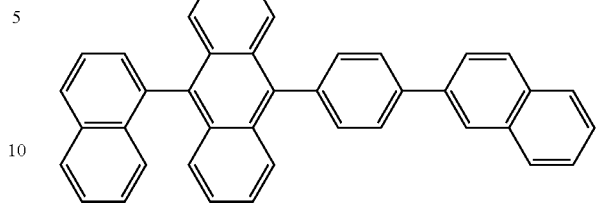
H13
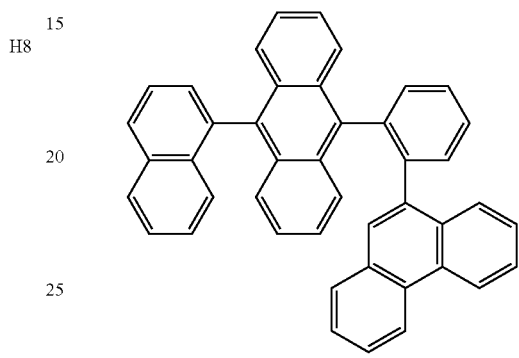
H14
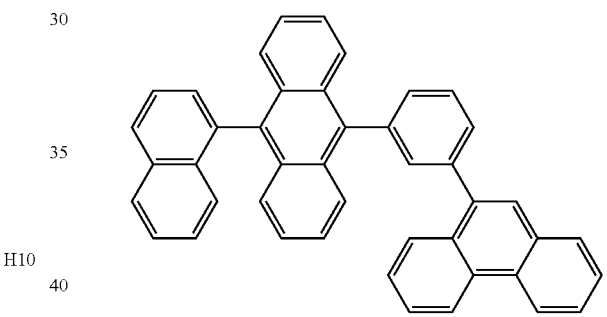
H15
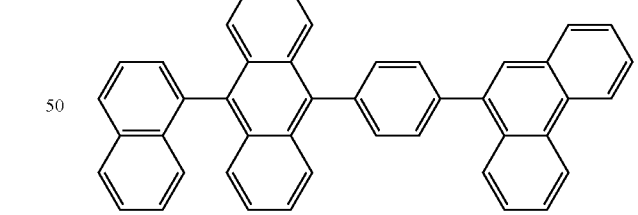
H16
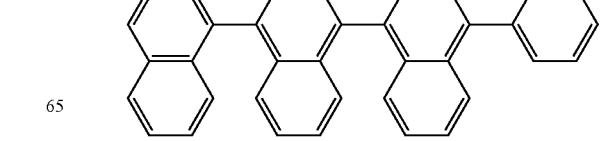

-continued
H17
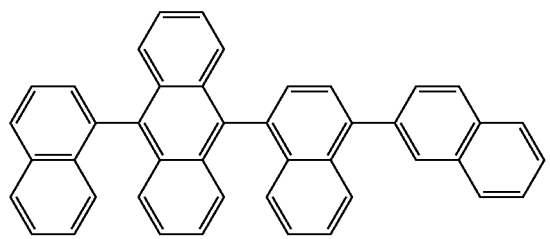
H18
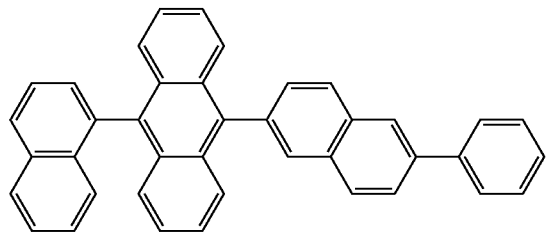
H19
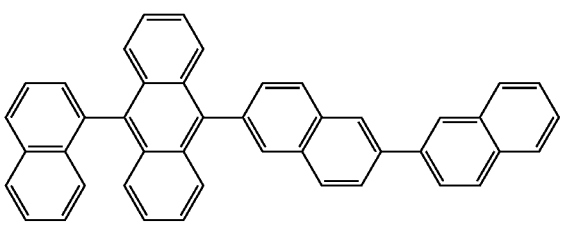
H20
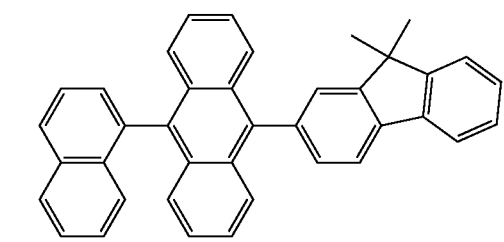
H21
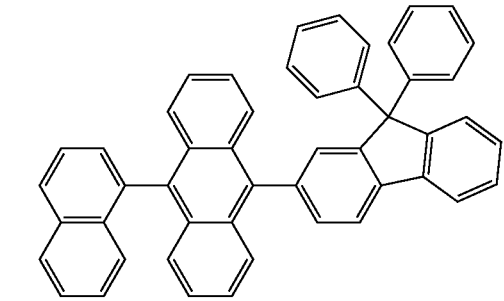
H22
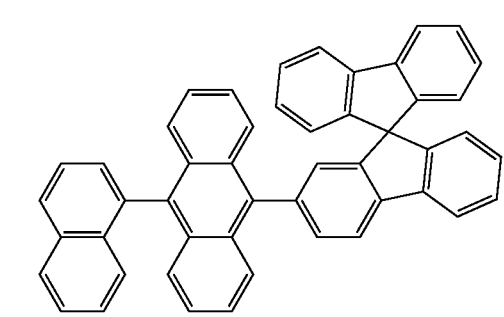
-continued
H23
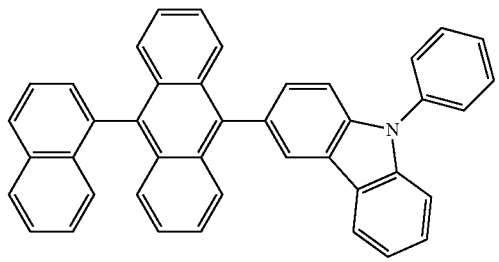
H24
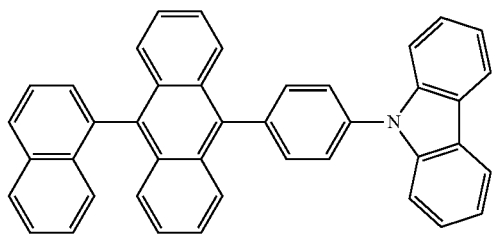
H25
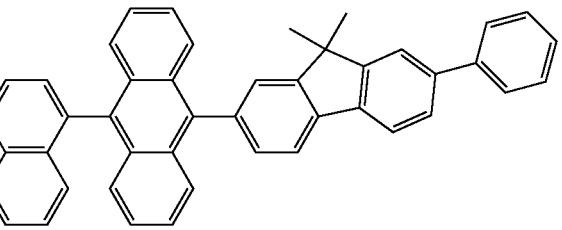
H26
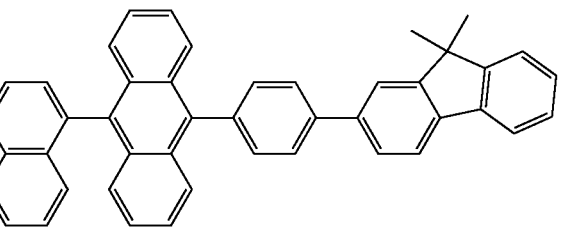
H27
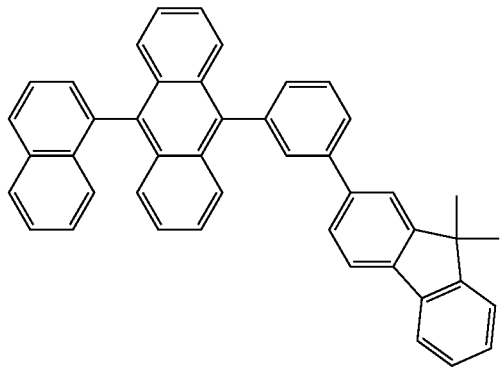

H28
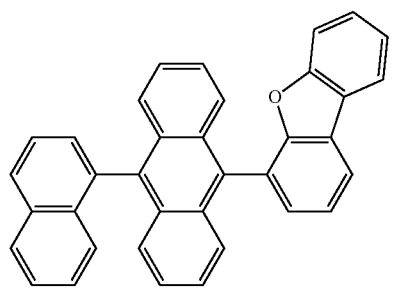
H29
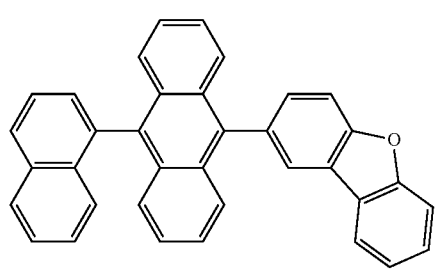
H30
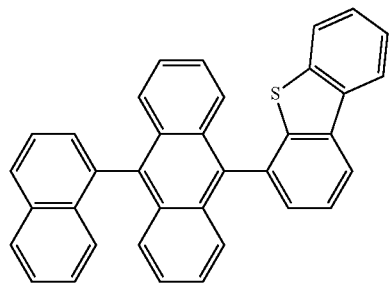
H31
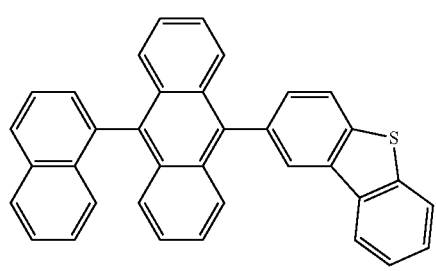
H32
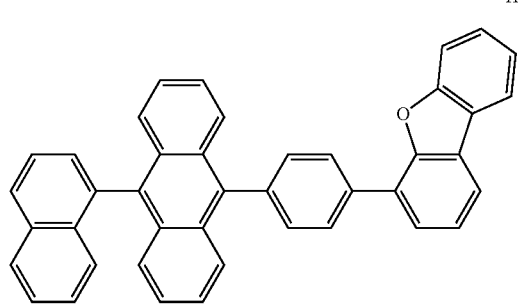
H33
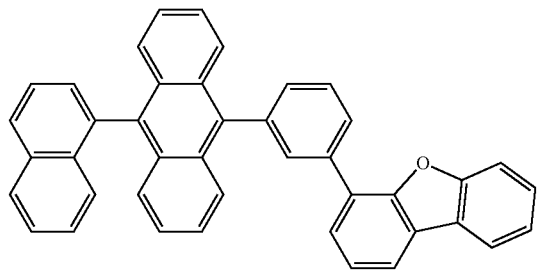
H34
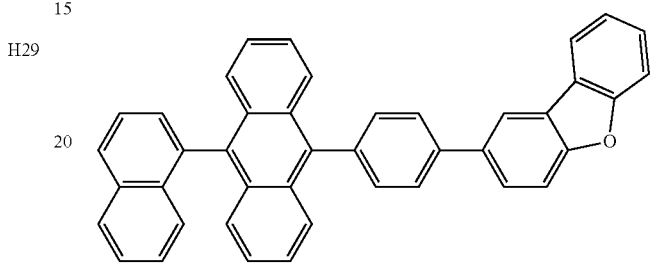
H35
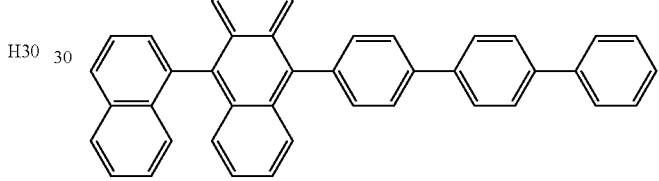
H36
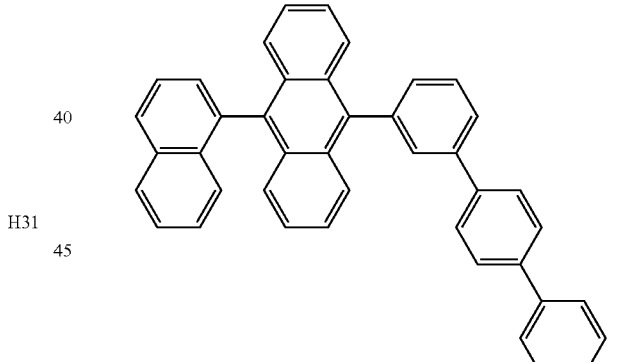
H37
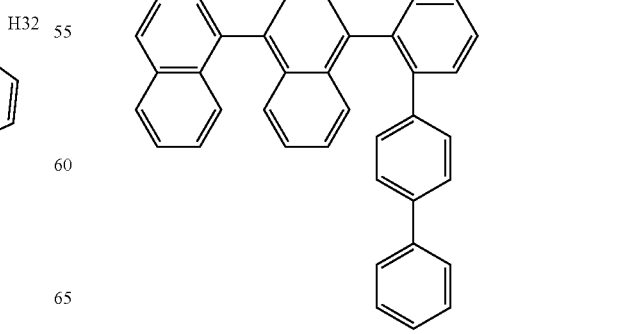

H38
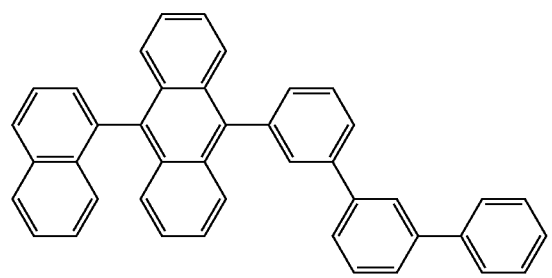
H39
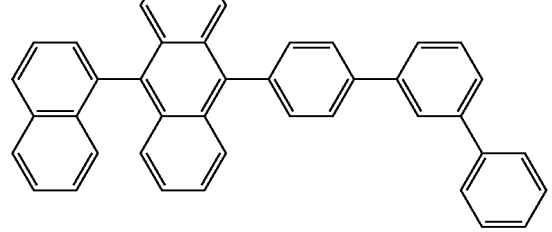
H40
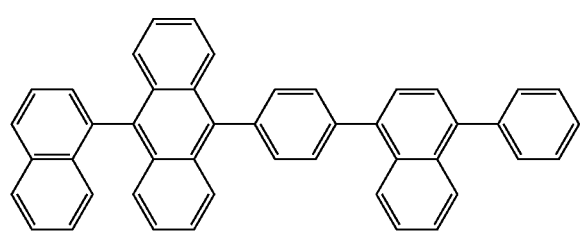
H41
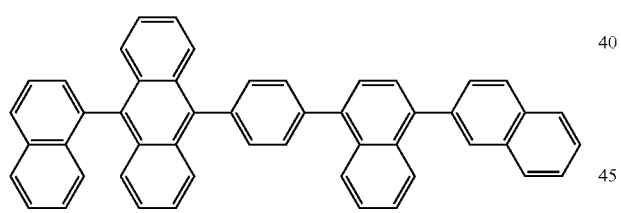
H42
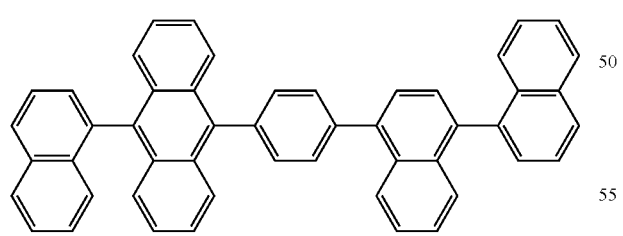
H43
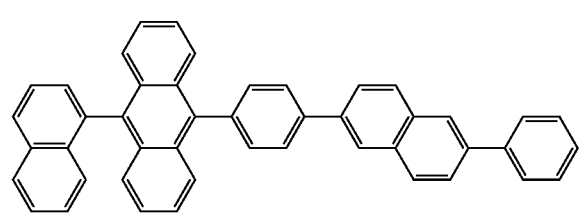
H44
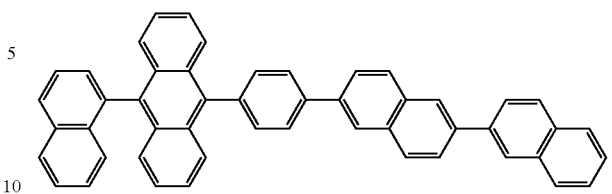
H45
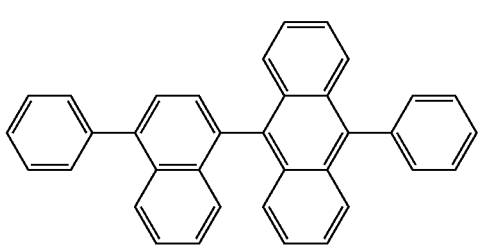
H46
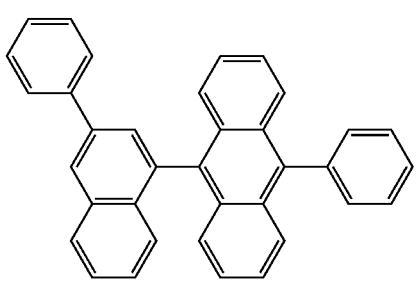
H47
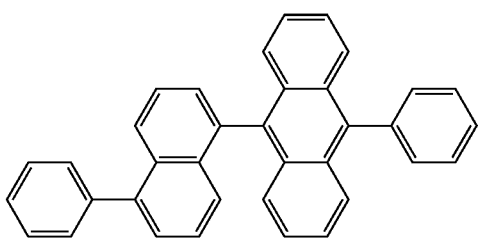
H48
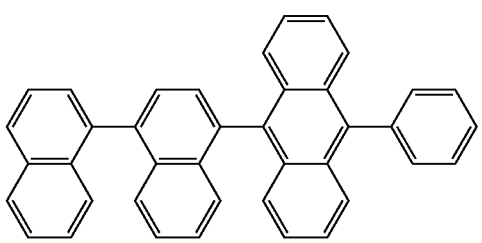
H49
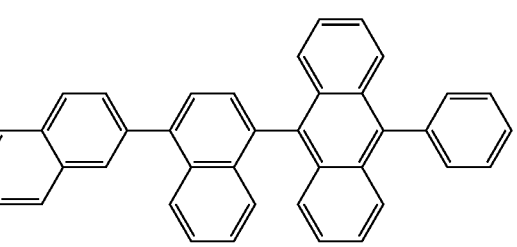

H50 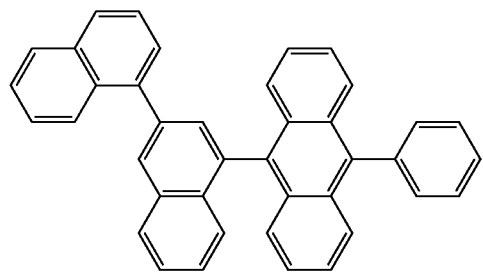
H51 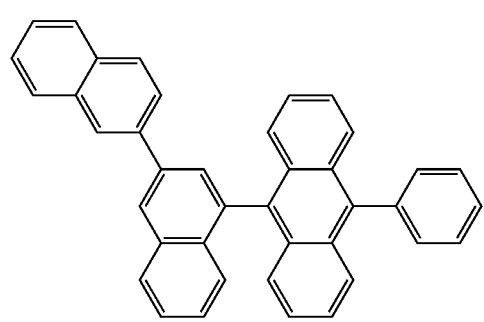
H52 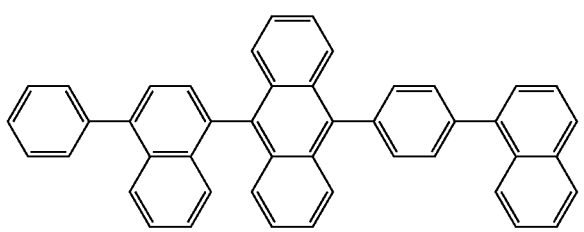
H53 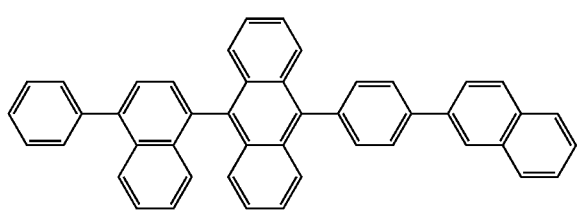
H54 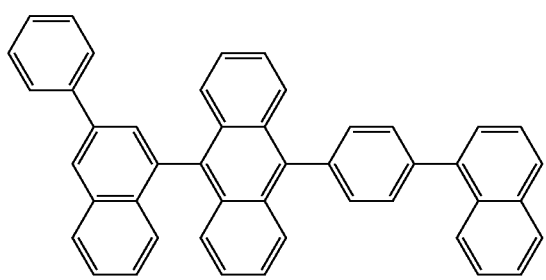
H55 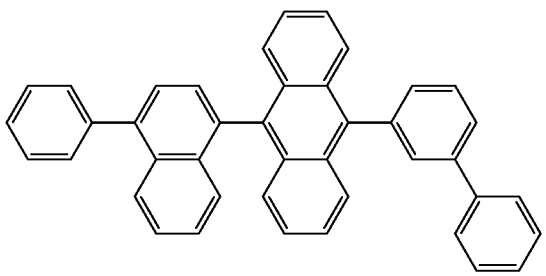
H56 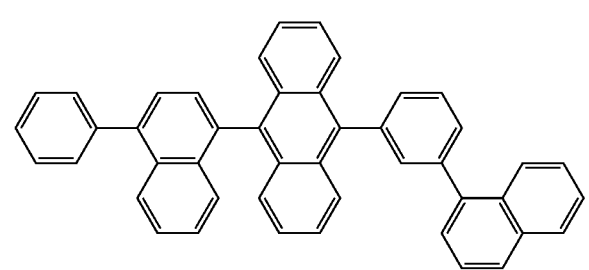
H57 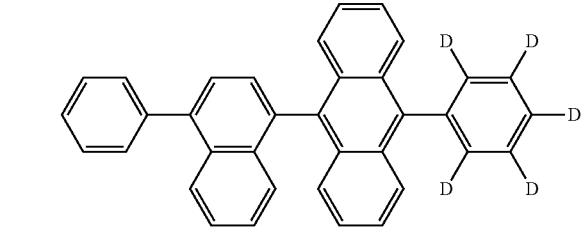
H58 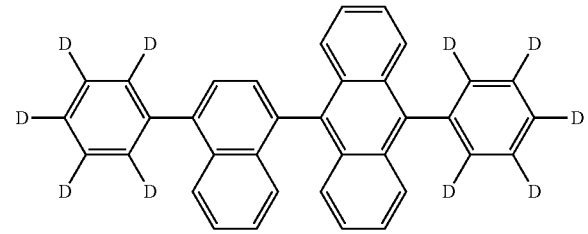
H59 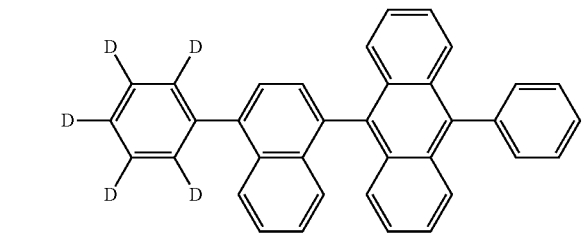
H60 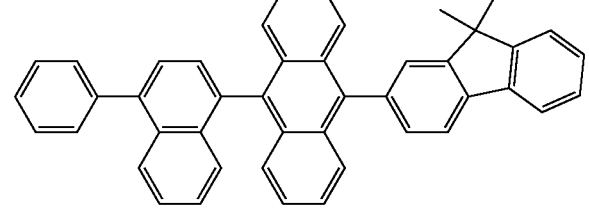

H61
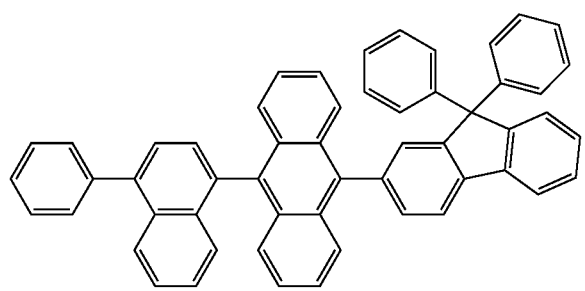
H62
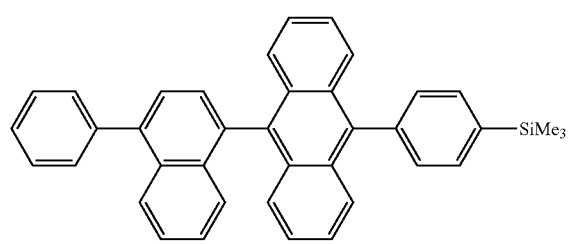
H63
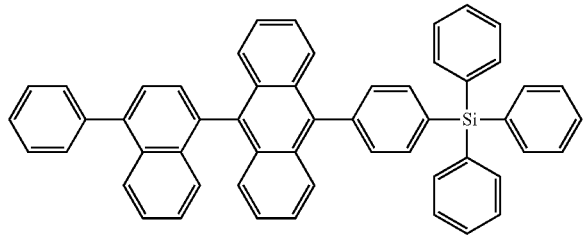
H64
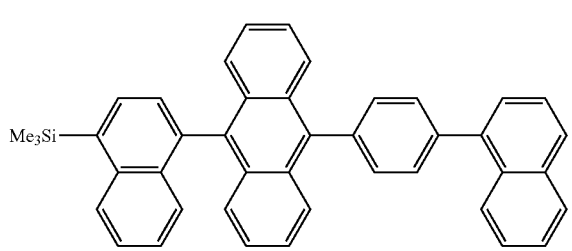
H65
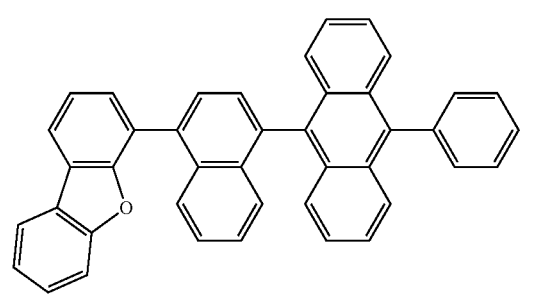
H66
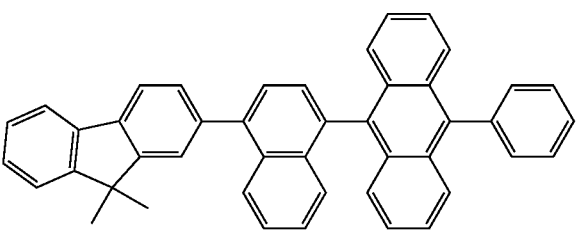
H67
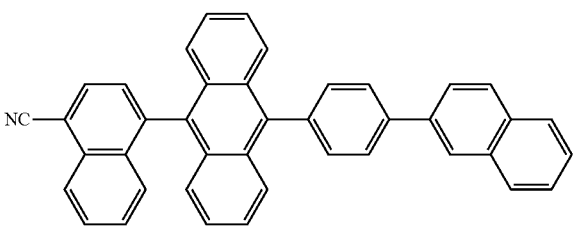
H68
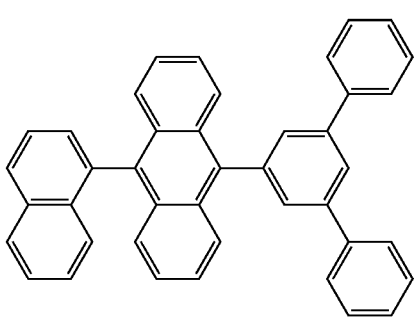
H69
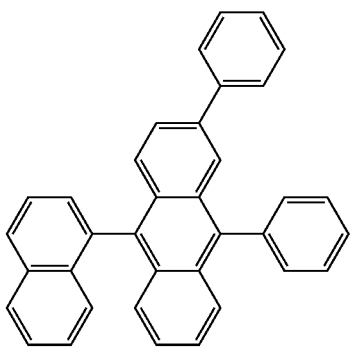
H70
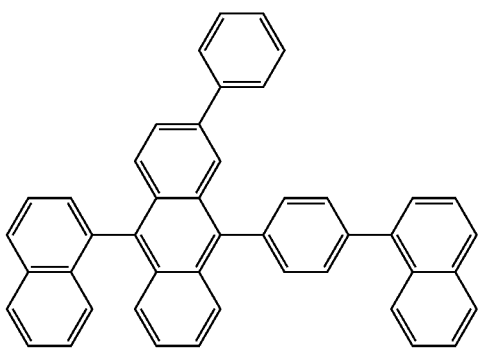

H71
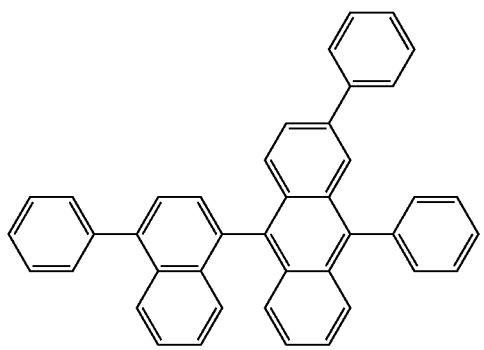
H72
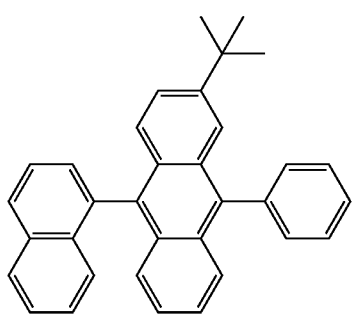
H73
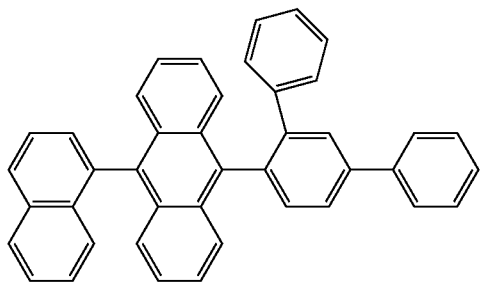
H74
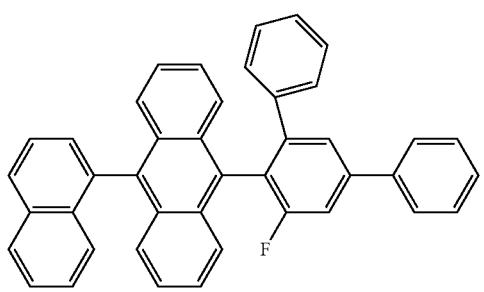
H75
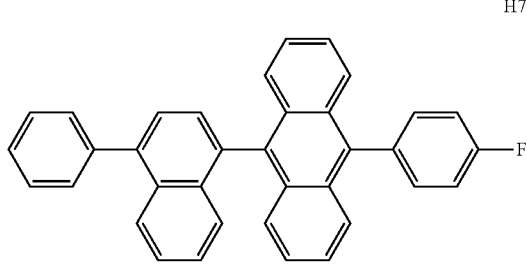
H76
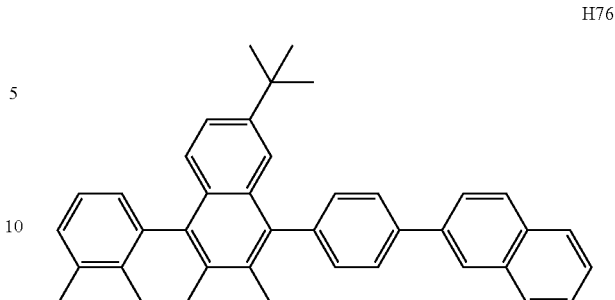
H77
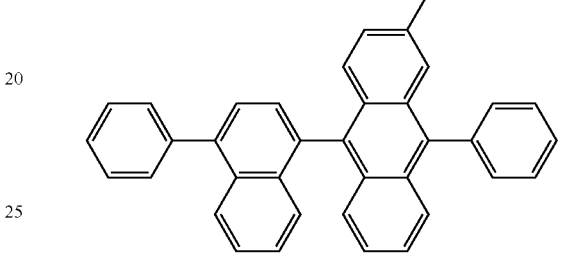
H78
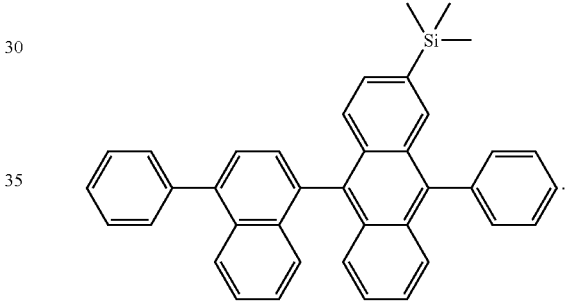
The emission layer may include any suitable host and dopant commonly known to those of skill in the art, as well as the compound represented by Formula 1 and compound represented by Formula 4.
The host may include at least one selected from TPBi, TBADN, ADN (herein, also known as "DNA"), CBP, CDBP, and TCP:
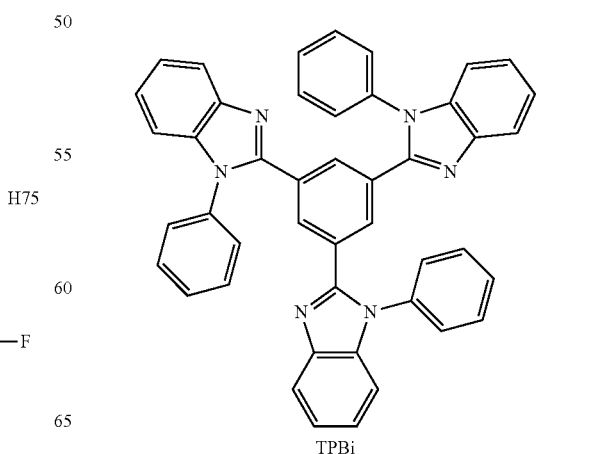
TPBi

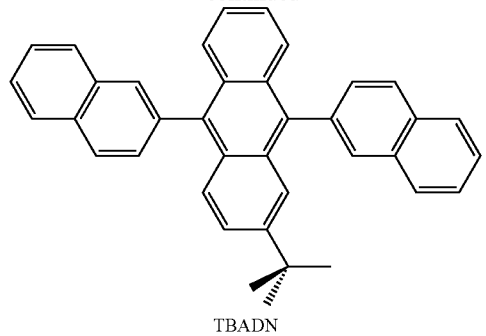
TBADN
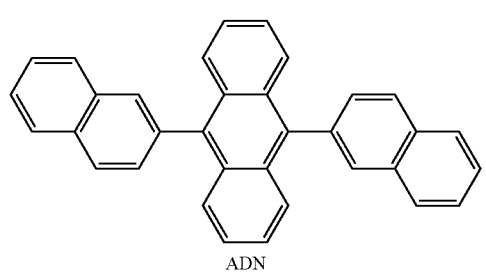
ADN
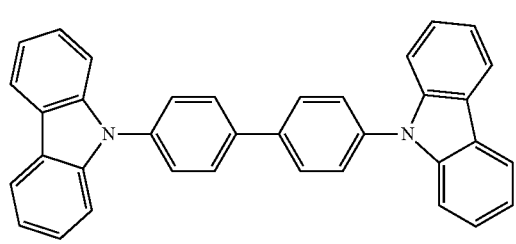
CBP
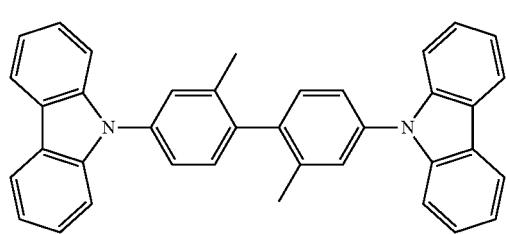
CDBP
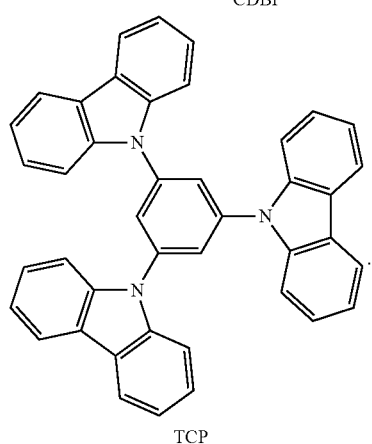
TCP
In some embodiments, the host may include at least one selected from Compounds H43 to H49 below, but is not limited thereto:
H43
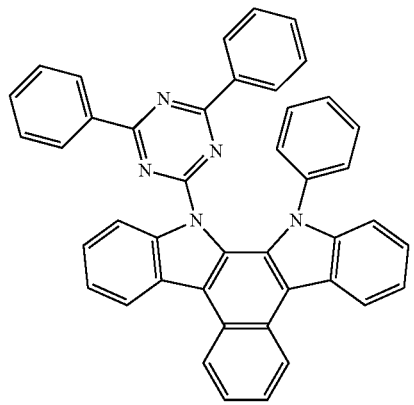
H44
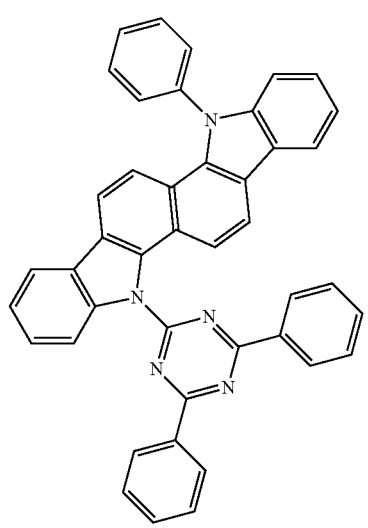
H45
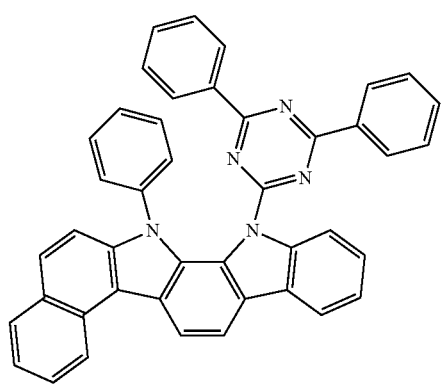

-continued

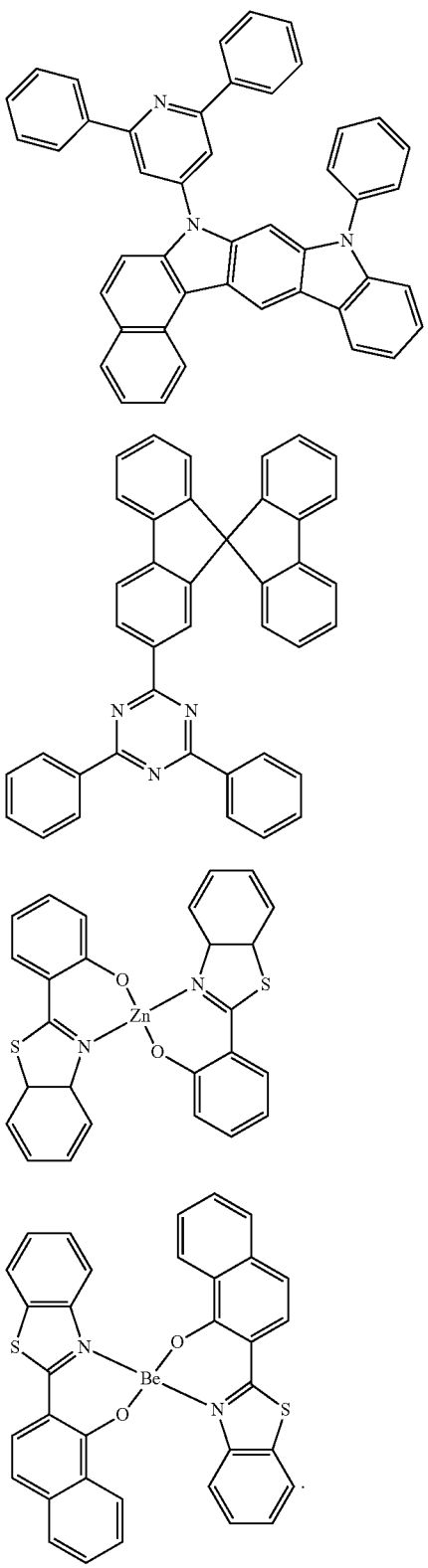

H46

H47

H48

H49

The dopant may further include at least one selected from a suitable fluorescent dopant and a phosphorescent dopant.

The phosphorescent dopant may include an organometallic complex represented by Formula 401 below:

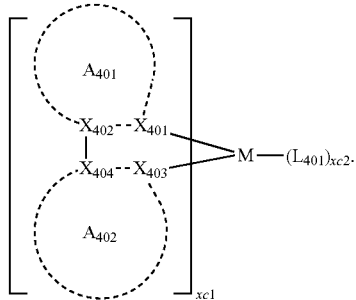

Formula 401

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may be each independently nitrogen or carbon;

$A_{401}$ and $A_{402}$ rings may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene;

at least one of substituents of the substituted benzene, substituted naphthalene, substituted fluorene, substituted spiro-fluorene, substituted indene, substituted pyrrole, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazole, substituted benzoimidazole, substituted benzofuran, substituted benzothiophene, substituted isobenzothiophene, substituted benzoxazole, substituted isobenzoxazole, substituted triazole, substituted oxadiazole, substituted triazine, substituted dibenzofuran, and substituted dibenzothiophene may be selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a C$_1$-C$_{60}$ alkyl group, a C$_2$-C$_{60}$ alkenyl group, a C$_2$-C$_{60}$ alkynyl group, and a C$_1$-C$_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_2$-C$_{60}$ heteroaryl group, a monovalent non-aromatic condensed polycyclic group, a monovalent non-aromatic condensed heteropolycyclic group, —N(Q$_{401}$)(Q$_{402}$), —Si(Q$_{403}$)(Q$_{404}$)(Q$_{405}$), and —B(Q$_{406}$)(Q$_{407}$), a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group;

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_2$-C$_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{60}$ alkyl group, a C$_2$-C$_{60}$ alkenyl group, a C$_1$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —N(Q$_{411}$)(Q$_{412}$), —Si(Q$_{413}$)(Q$_{414}$)(Q$_{415}$), and —B(Q$_{416}$)(Q$_{417}$), and —N(Q$_{421}$)(Q$_{422}$), —Si(Q$_{423}$)(Q$_{424}$)(Q$_{425}$), and —B(Q$_{426}$)(Q$_{427}$);

where Q$_{401}$ to Q$_{407}$, Q$_{411}$ to Q$_{417}$, and Q$_{421}$ to Q$_{427}$, are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_1$-C$_{60}$ heteroaryl group, a monovalent non-aromatic condensed polycyclic group, and a monovalent non-aromatic condensed heteropolycyclic group.

L$_{401}$ may be an organic ligand;

xc1 may be selected from 1, 2, and 3; and xc2 may be selected from 0, 1, 2, and 3.

L$_{401}$ may be any suitable monovalent, divalent, or trivalent organic ligand. For example, L$_{401}$ may be selected from a halogen ligand (for example, Cl$^-$ or F$^-$), a diketone ligand (for example, acetylacetonate, 1,3-diphenyl-1,3-propanedionate, 2,2,6,6-tetramethyl-3,5-heptanedionate, and/or hexafluoroacetonate), a carboxylic acid ligand (for example, picolinate, dimethyl-3-pyrazolecarboxylate, and/or benzoate), a carbon monooxide ligand, an isonitrile ligand, a cyano ligand, and a phosphorous ligand (for example, phosphine, or phosphate), but embodiments of the present invention are not limited thereto.

When A$_{401}$ in Formula 401 has a plurality of substituents, two or more of the plurality of substituents of A$_{401}$ may bind to each other to form a saturated or unsaturated ring.

When A$_{402}$ in Formula 401 has a plurality of substituents, two or more of the plurality of substituents of A$_{402}$ may bind to each other to form a saturated or unsaturated ring.

When xc1 in Formula 401 is two or more, a plurality of ligands

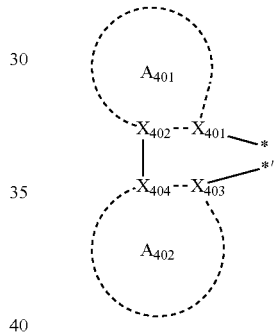

in Formula 401 may be identical to or different from each other. In Formula 401, when xc1 is 2 or more, A$_{401}$ and/or A$_{402}$ of one ligand may be respectively linked to A$_{401}$ and/or A$_{402}$ of an adjacent ligand, directly (e.g., via a single bond) or connected via a linking group (for example, a C$_1$-C$_5$ alkylene group, —N(R')— (wherein R' is a C$_1$-C$_{10}$ alkyl group or a C$_6$-C$_{20}$ aryl group), and/or —C(=O)—).

The fluorescent dopant may include at least one selected from DPVBi, BDAVBi, TBPe, DCM, DCJTB, Coumarin 6, and C545T as well as the compound represented by Formula 1.

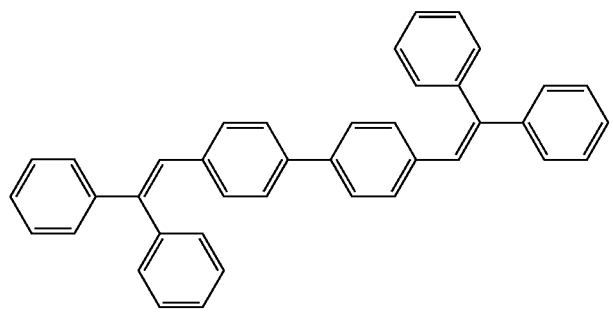

DPVBi

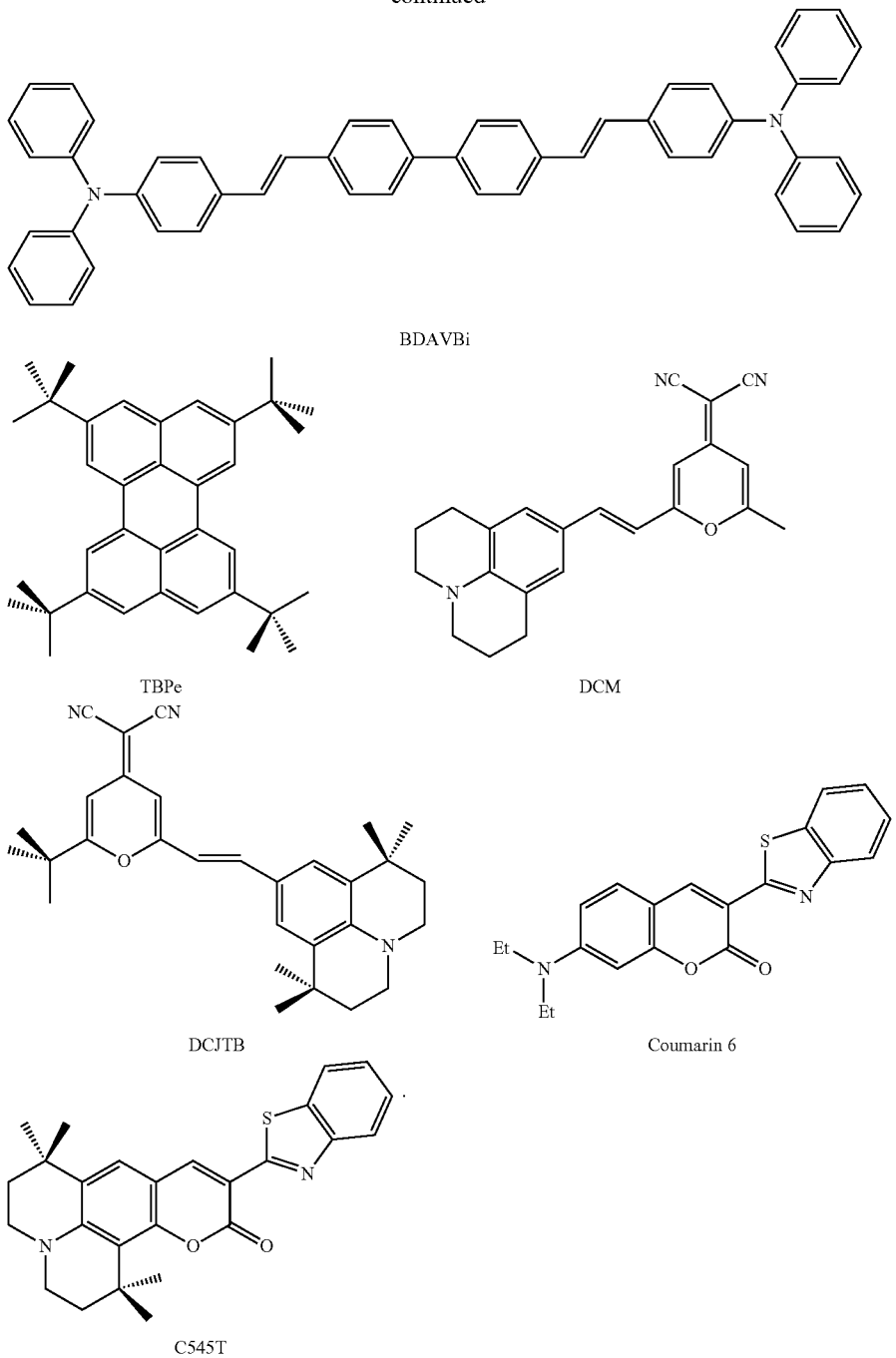

BDAVBi

TBPe

DCM

DCJTB

Coumarin 6

C545T

An amount of the dopant in the emission layer may be, in general, in a range of about 0.01 parts by weight to about 15 parts by weight based on 100 parts by weight of the host, but the amount of the dopant is not limited thereto.

A thickness of the emission layer may be in a range of about 100 Å to about 1000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer (ETL), and an electron injection layer, but embodiments of the present invention are not limited thereto.

For example, the electron transport region may have a structure of electron transport layer/electron injection layer or a structure of hole blocking layer/electron transport layer/electron injection layer, where the layers of each structure are sequentially stacked from the emission layer in the stated order, but the structure of the electron transport region is not limited thereto.

The electron transport region may include a hole blocking layer. When the emission layer includes a phosphorescent dopant, the hole blocking layer may be formed to prevent or substantially reduce the diffusion of excitons or holes into an electron transport layer.

When the electron transport region includes a hole blocking layer, the hole blocking layer may be formed on the emission layer by using one or more suitable methods, such as vacuum-deposition, spin coating, casting, LB method, ink-jet printing, laser-printing, and/or LITI. When the hole blocking layer is formed by vacuum-deposition and/or spin coating, the deposition and coating conditions for the hole blocking layer may be similar to the deposition and coating conditions for the hole injection layer.

The hole blocking layer may include, for example, at least one selected from BCP and Bphen, but is not limited thereto.

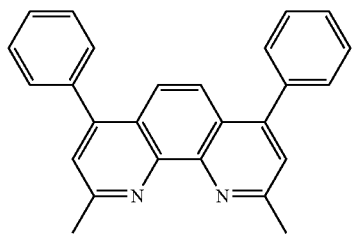

BCP

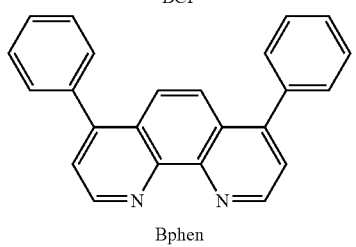

Bphen

A thickness of the hole blocking layer may be in a range of about 20 Å to about 1000 Å, for example, about 30 Å to about 300 Å. When the thickness of the hole blocking layer is within this range, excellent hole blocking characteristics may be obtained without a substantial increase in driving voltage.

The electron transport region may include an electron transport layer. The electron transport layer may be formed on the emission layer or the hole blocking layer by using one or more suitable methods, such as vacuum deposition, spin coating, casting, LB method, ink-jet printing, laser-printing, and/or LITI. When the electron transport layer is formed by using vacuum deposition and/or spin coating, vacuum deposition and coating conditions for the electron transport layer may be similar to the vacuum deposition and coating conditions for the hole injection layer.

In some embodiments, the organic layer 150 of the organic light-emitting device includes an electron transport region between the emission layer and the second electrode 190. The electron transport region may include at least one selected from an electron transport layer and an electron injection layer, but is not limited thereto.

The electron transport layer may include at least one selected from BCP, Bphen, Alq$_3$, BAlq, TAZ, and NTAZ.

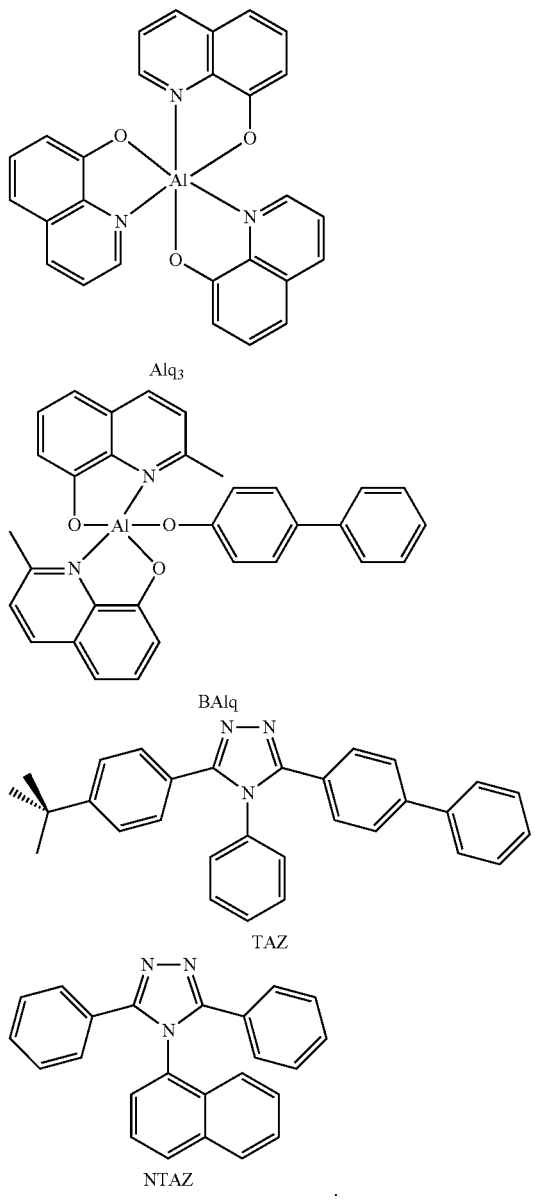

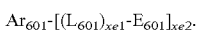

In some embodiments, the electron transport layer may include at least one compound selected from a compound represented by Formula 601 and a compound represented by Formula 602 illustrated below: Formula 601

$Ar_{601}$-[($L_{601}$)$_{xe1}$-$E_{601}$]$_{xe2}$.

In Formula 601, $Ar_{601}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$), where $Q_{301}$ to $Q_{303}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group;

$L_{601}$ may be the same as defined in connection with $L_{201}$;

$E_{601}$ may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spirofluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

xe1 may be selected from 0, 1, 2, and 3; and
xe2 may be selected from 1, 2, 3, and 4.

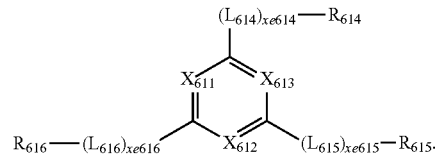

Formula 602

In Formula 602, $X_{611}$ may be N or C-($L_{611}$)$_{xe611}$-$R_{611}$, $X_{612}$ may be N or C-($L_{612}$)$_{xe612}$-$R_{612}$, $X_{613}$ may be N or C-($L_{613}$)$_{xe613}$-$R_{613}$, and at least one selected from $X_{611}$ to $X_{613}$ may be N;

$L_{611}$ to $L_{616}$ may be each independently the same as defined in connection with $L_{201}$ provided herein;

$R_{611}$ to $R_{616}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xe611 to xe616 may be each independently selected from 0, 1, 2, and 3.

The compound represented by Formula 601 and the compound represented by Formula 602 may each independently be selected from Compounds ET1 to ET15 illustrated below:

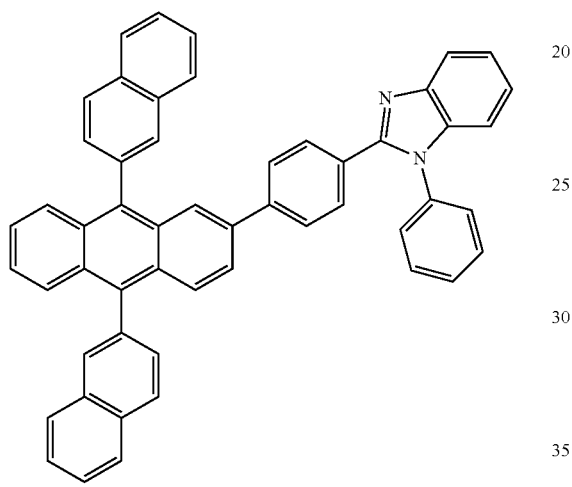

ET1

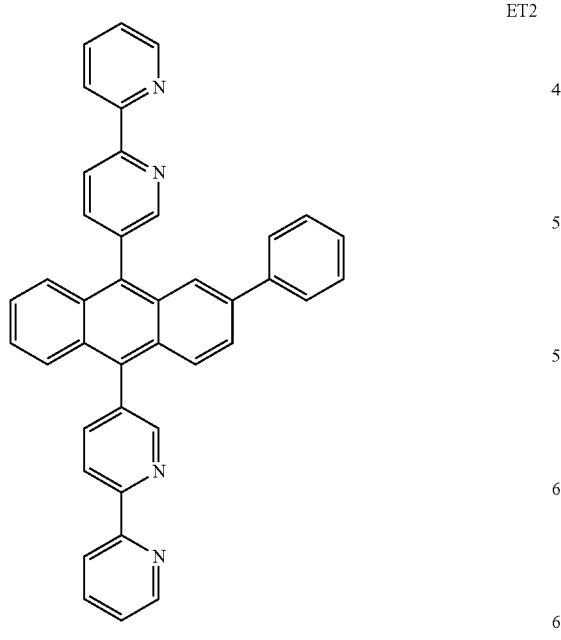

ET2

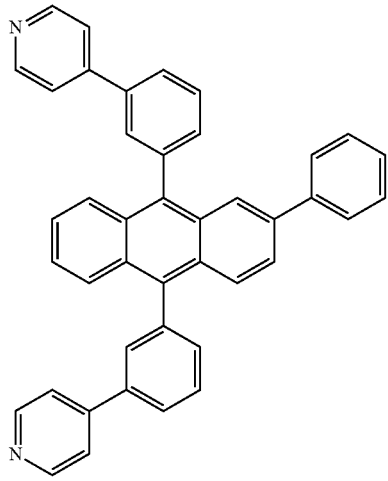

ET3

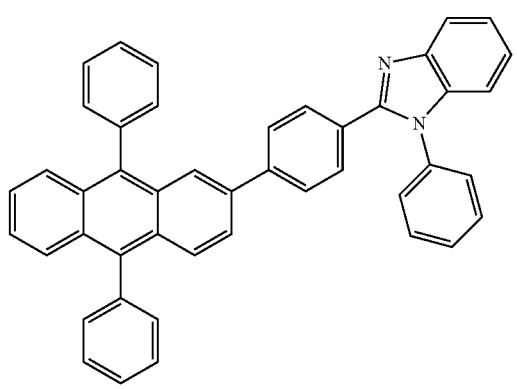

ET4

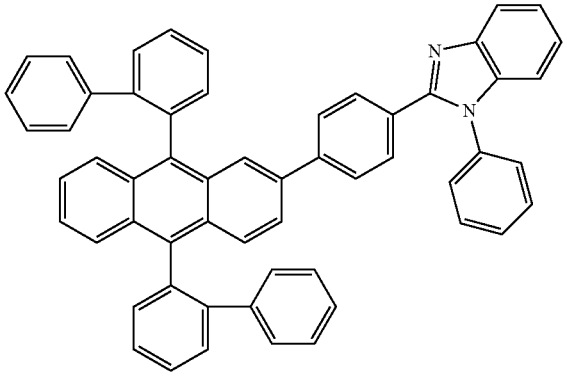

ET5

ET6
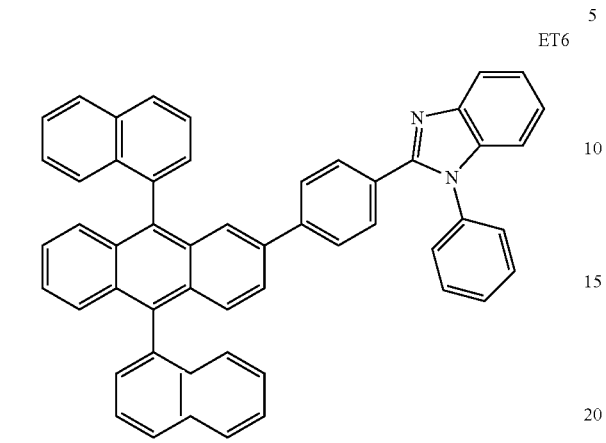
ET9
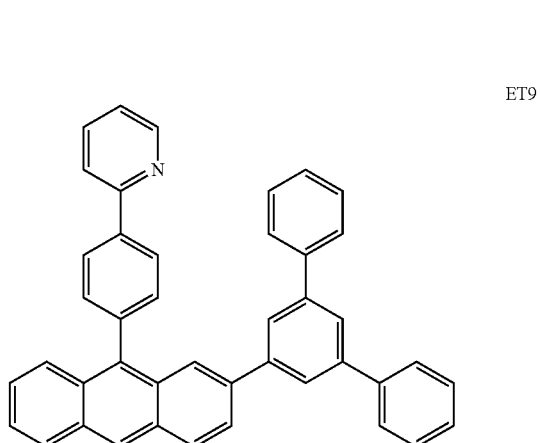
ET7
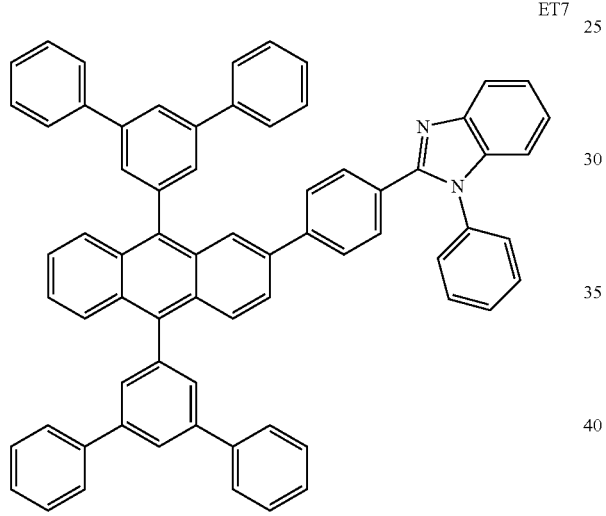
ET8
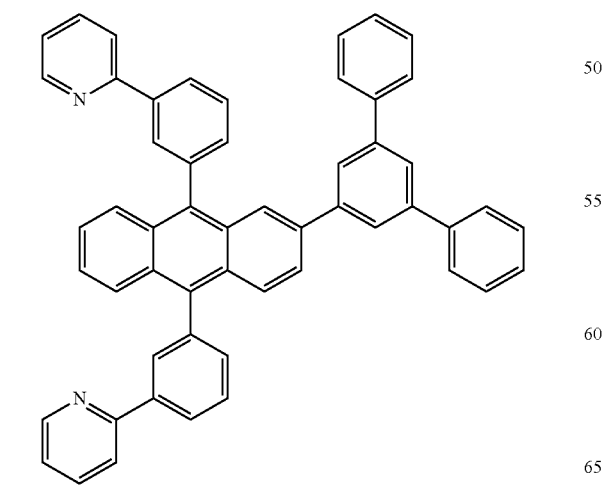
ET10
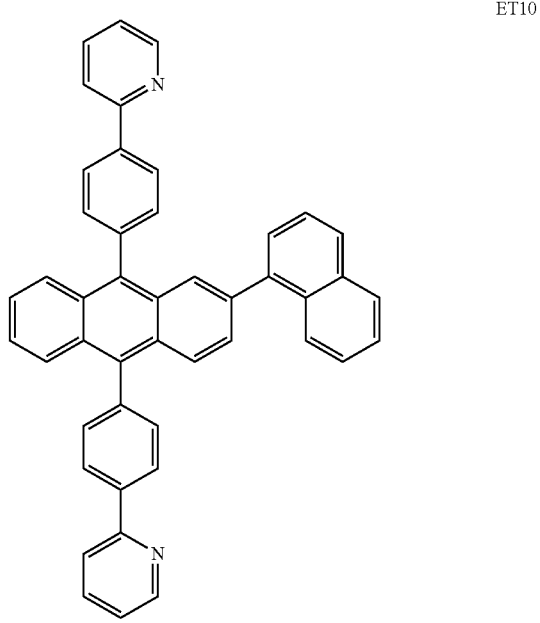

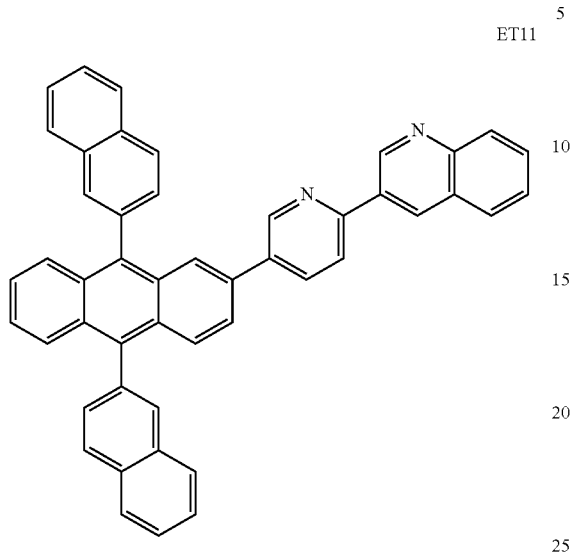

ET11

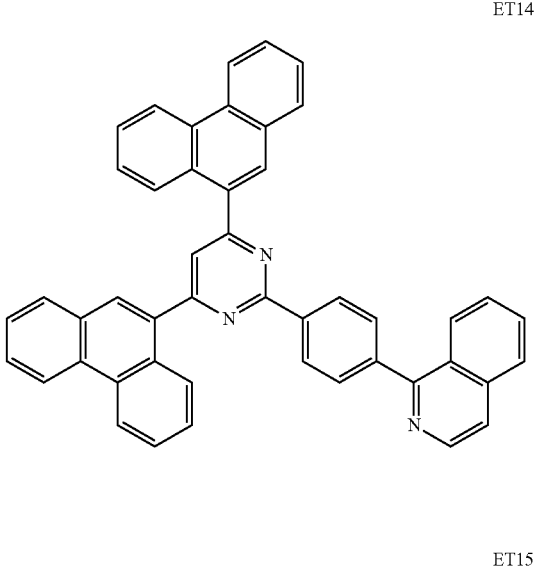

ET14

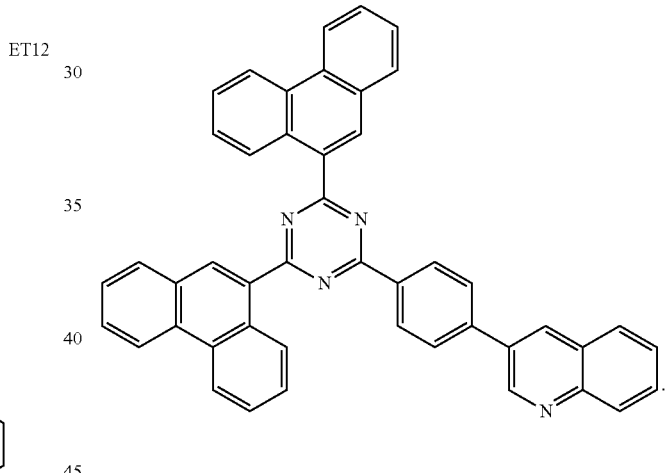

ET15

ET12

ET13

A thickness of the electron transport layer may be in a range of about 100 Å to about 1000 Å, for example, about 150 Å to about 500 Å. When the thickness of the electron transport layer is within this range, excellent electron transport characteristics may be obtained without a substantial increase in driving voltage.

The electron transport layer may further include a metal-containing material in addition to the materials described above.

The metal-containing material may include a Li complex. The Li complex may include, for example, Compound ET-D1 (lithium quinolate, LiQ) or ET-D2:

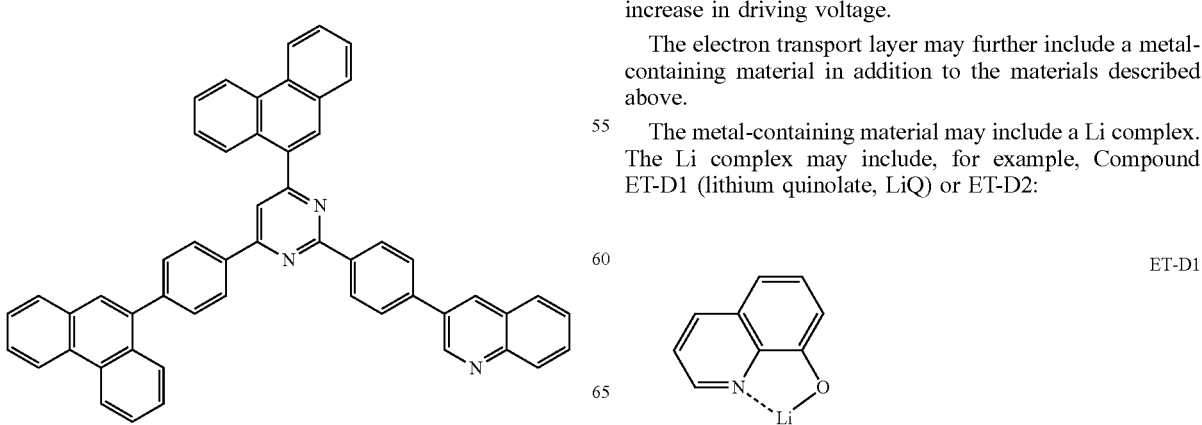

ET-D1

ET-D2

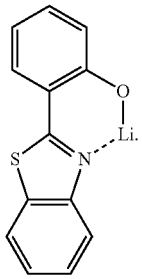

The electron transport region may include an electron injection layer that facilitates electron injection from the second electrode 190.

The electron injection layer may be formed on the electron transport layer by using one or more suitable methods, such as vacuum-deposition, spin coating, casting, LB method, ink-jet printing, laser-printing, and/or LITI. When the electron injection layer is formed by vacuum deposition and/or spin coating, vacuum deposition and coating conditions for the electron injection layer may be similar to the vacuum-deposition and coating conditions for the hole injection layer.

The electron injection layer may include at least one selected from LiF, NaCl, CsF, $Li_2O$, BaO, and LiQ.

A thickness of the electron injection layer may be in a range of about 1 Å to about 100 Å, for example, about 3 Å to about 90 Å. When the thickness of the electron injection layer is within this range, excellent electron injection characteristics may be obtained without a substantial increase in driving voltage.

The second electrode 190 is positioned on the organic layer 150. The second electrode 190 may be a cathode that is an electron injection electrode, and in this regard, a material for forming the second electrode 190 may be a material having a low work function, for example, a metal, an alloy, an electrically conductive compound, or a mixture thereof. Non-limiting examples of the material for forming the second electrode 190 include lithium (Li), magnesium (Mg), aluminum (Al), aluminum-lithium (Al—Li), calcium (Ca), magnesium-indium (Mg—In), and magnesium-silver (Mg—Ag). In some embodiments, the material for forming the second electrode 190 may be ITO or IZO. The second electrode 190 may be a reflective electrode, a semi-transmissive electrode, or a transmissive electrode.

Hereinbefore, the organic light-emitting device has been described with reference to the drawing, but embodiments of the present invention are not limited thereto.

Hereinafter, definitions of substituents used herein will be presented (the number of carbon numbers used to restrict a substituent is not limited, and does not limit properties of the substituent, and unless stated otherwise, the definition of the substituent is consistent with a general definition thereof).

A $C_1$-$C_{60}$ alkyl group used herein refers to a linear or branched aliphatic hydrocarbon monovalent group having 1 to 60 carbon atoms in the main carbon chain, and non-limiting examples thereof include a methyl group, an ethyl group, a propyl group, an iso-butyl group, a sec-butyl group, a tert-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (where $A_{101}$ is the $C_1$-$C_{60}$ alkyl group), and non-limiting examples thereof include a methoxy group, an ethoxy group and an isopropyloxy group.

A $C_2$-$C_{60}$ alkenyl group used herein refers to a hydrocarbon group having at least one carbon-carbon double bond at one or more positions along a carbon chain of the $C_2$-$C_{60}$ alkyl group (e.g., in the middle or at either terminal end of the $C_2$-$C_{60}$ alkyl group), and non-limiting examples thereof include an ethenyl group, a propenyl group, and a butenyl group. A $C_2$-$C_{60}$ alkenylene group used herein refers to a divalent group having the same structure as the $C_2$-$C_{60}$ alkenyl group.

A $C_2$-$C_{60}$ alkynyl group used herein refers to a hydrocarbon group having at least one carbon-carbon triple bond at one or more positions along a carbon chain of the $C_2$-$C_{60}$ alkyl group (e.g., in the middle or at either terminal end of the $C_2$-$C_{60}$ alkyl group), and non-limiting examples thereof include an ethynyl group and a propynyl group. A $C_2$-$C_{60}$ alkynylene group used herein refers to a divalent group having the same structure as the $C_2$-$C_{60}$ alkynyl group.

A $C_3$-$C_{10}$ cycloalkyl group used herein refers to a monovalent monocyclic saturated hydrocarbon group including 3 to 10 carbon atoms as ring-forming atoms, and non-limiting examples thereof include a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_1$-$C_{10}$ heterocycloalkyl group used herein refers to a monovalent monocyclic group including at least one hetero atom selected from N, O, P, and S as a ring-forming atom and 1 to 10 carbon atoms as the remaining ring-forming atoms. Non-limiting examples thereof include a tetrahydrofuranyl group and a tetrahydrothiophenyl group. A $C_1$-$C_{10}$ heterocycloalkylene group used herein refers to a divalent group having the same structure as the $C_1$-$C_{10}$ heterocycloalkyl group.

A $C_3$-$C_{10}$ cycloalkenyl group used herein refers to a monovalent monocyclic group that has 3 to 10 carbon atoms as ring-forming atoms and at least one double bond in its ring, and is not aromatic. Non-limiting examples thereof include a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_1$-$C_{10}$ heterocycloalkenyl group used herein refers to a monovalent monocyclic group including at least one hetero atom selected from N, O, P, and S as a ring-forming atom, 1 to 10 carbon atoms as the remaining ring-forming atoms, and at least one double bond in its ring. Non-limiting examples of the $C_1$-$C_{10}$ heterocycloalkenyl group include a 2,3-hydrofuranyl group and a 2,3-hydrothiophenyl group. A $C_1$-$C_{10}$ heterocycloalkenylene group used herein refers to a divalent group having the same structure as the $C_1$-$C_{10}$ heterocycloalkenyl group.

A $C_6$-$C_{60}$ aryl group used herein refers to a monovalent group including a carbocyclic aromatic system having 6 to 60 carbon atoms, and a $C_6$-$C_{60}$ arylene group used herein refers to a divalent group including a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and/or the $C_6$-$C_{60}$ arylene group each include a plurality of rings, the rings may be fused to each other.

A $C_1$-$C_{60}$ heteroaryl group used herein refers to a monovalent group having a carbocyclic aromatic system including at least one hetero atom selected from N, O, P, and S as a ring-forming atom and 1 to 60 carbon atoms as the remaining ring-forming atoms. A $C_1$-$C_{60}$ heteroarylene group used herein refers to a divalent group having a carbocyclic aromatic system including at least one hetero atom selected from N, O, P, and S as a ring-forming atom and 1 to 60 carbon atoms as the remaining ring-forming atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and/or the $C_1$-$C_{60}$ heteroarylene group each include a plurality of rings, the rings may be fused to each other.

A $C_6$-$C_{60}$ aryloxy group used herein refers to a group represented by —$OA_{102}$ (where $A_{102}$ is the $C_6$-$C_{60}$ aryl group), and a $C_6$-$C_{60}$ arylthio group used herein refers to a group represented by —$SA_{103}$ (where $A_{103}$ is the $C_6$-$C_{60}$ aryl group).

A monovalent non-aromatic condensed polycyclic group used herein refers to a monovalent group that has two or more rings condensed to each other, only carbon atoms as ring forming atoms (for example, the number of carbon atoms may be in a range of 6 to 60 as in, for example, a $C_6$-$C_{20}$ condensed polycyclic group), wherein the molecular structure as a whole is non-aromatic. A non-limiting example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group that has two or more rings condensed to each other, has a hetero atom selected from N, O P, and S as a ring-forming atom, and carbon atoms as the remaining ring-forming atoms (for example, the number of carbon atoms may be in a range of 2 to 60), wherein the molecular structure as a whole is non-aromatic. A non-limiting example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

At least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$;

where $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In some embodiments, at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{11}$)($Q_{12}$), —Si($Q_{13}$)($Q_{14}$)($Q_{15}$), and —B($Q_{16}$)($Q_{17}$);

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), where $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

The organic light-emitting device according to one or more embodiments of the present invention may be included in various types (kinds) of flat panel display apparatuses, for example, in a passive matrix organic light-emitting display apparatus and/or an active matrix organic light-emitting display apparatus. When the organic light-emitting device is included in an active matrix organic light-emitting display apparatus, a first electrode disposed on a substrate is a pixel electrode, and the first electrode may be electrically connected to a source electrode or drain electrode of a thin film transistor. In addition, the organic light-emitting device may be included in a flat panel display apparatus that may display images on both sides.

Further, the organic layer of the organic light-emitting device according to the present embodiments may be formed by vacuum-depositing the compound desribed above in connection with one or more embodiments of the present invention and/or using (utilizing) a wet method in which the compound according to one or more embodiments of the present invention is prepared in the form of a solution, and then the solution of the compound is used for coating.

"Ph" used herein refers to a phenyl group, "Me" refers to a methyl group, "Et" refers to an ethyl group, and "ter-Bu" or "Bu$^t$" refers to a tert-butyl group.

Hereinafter, an organic light-emitting device according to one or more embodiments will be described in detail with reference to Synthesis Examples and Examples. However, these examples are for illustrative purposes only and are not intended to limit the scope of the present invention.

EXAMPLE

Synthesis Example 1

Synthesis of Compound 8

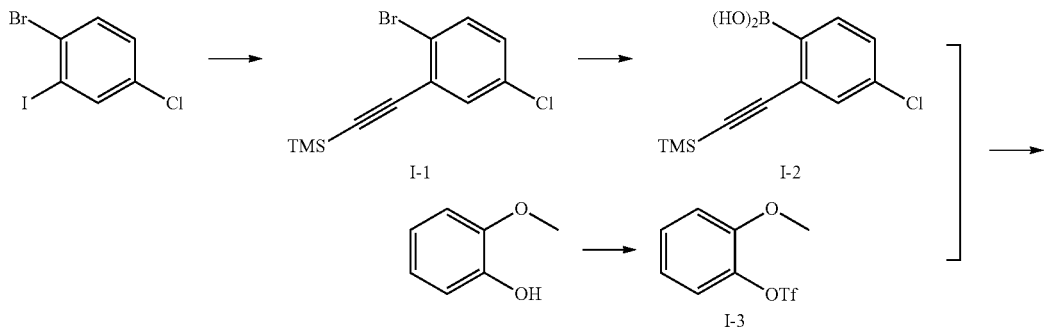

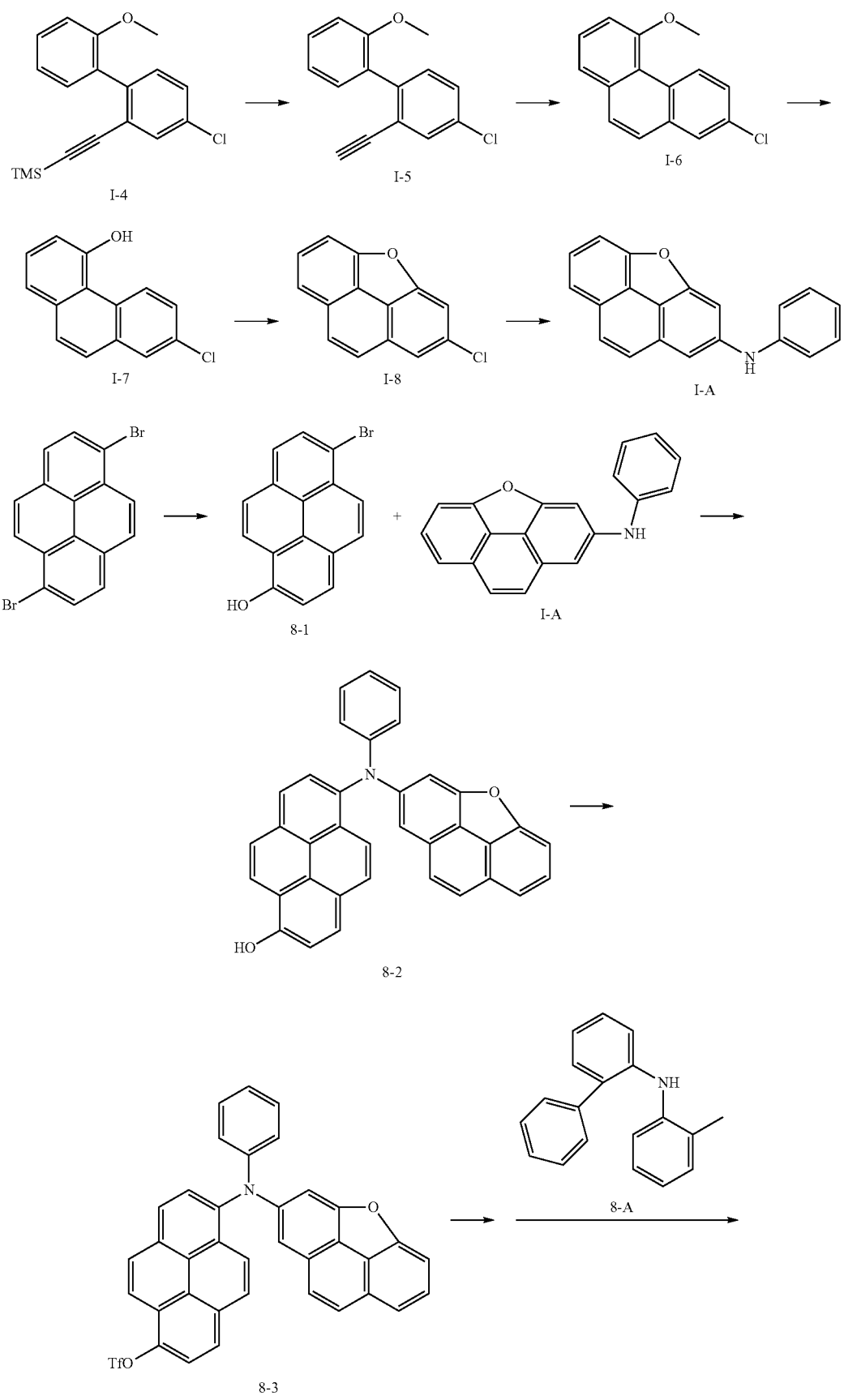

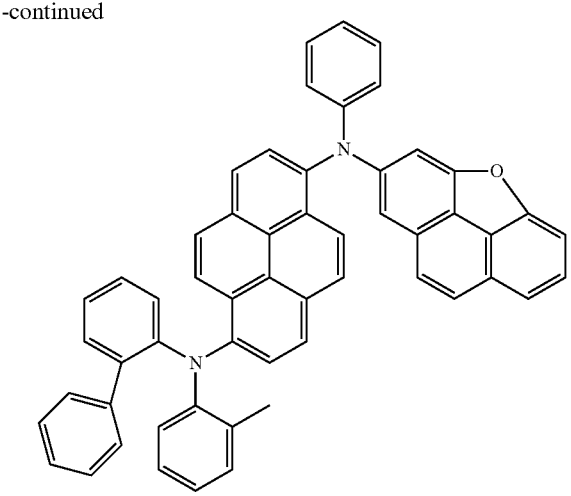

8

Synthesis of Intermediate I-1

17.2 g (54.4 mmol) of 1-bromo-4-chloro-2-iodobenzene, 600 mg (2.7 mmol) of Pd(OAc)$_2$, 1.5 g (5.72 mmol) of PPh$_3$, and 1.1 g (5.77 mmol) of CuI were dissolved in 375 ml (272 mmol) of triethylamine, and the resulting solution was stirred at 60° C. for 12 hours under N$_2$ atmosphere. Once the reaction was complete, the result was allowed to cool down to room temperature. Then, an organic layer was extracted five times therefrom by using each of water and diethyl ether. The obtained organic layer was dried by using magnesium sulfate (MgSO$_4$). Then, a solvent was removed therefrom by evaporation. The obtained residue was separated and purified through a silica gel chromatography to thereby obtain 25.2 g (47.6 mmol) of Intermediate I-1 (yield: 87.5%). The obtained compound was identified by mass spectroscopy/fast atom bombardment (MS/FAB).

C11H12BrBrSi cal. 287.65, found 287.68.

Synthesis of Intermediate I-2

25.2 g (47.6 mmol) of Intermediate I-1 was dissolved in 500 ml of tetrahydrofuran (THF), and was stirred at –78° C. for 10 minutes under N$_2$ atmosphere. Then, 19 ml of 2.5 M n-BuLi was slowly added dropwise by using a dropping funnel, and the resulting solution was stirred for additional 30 minutes. Then, 4.95 g (52.4 mmol) of trimethyl borate was slowly added dropwise by using a dropping funnel, and the solution was additionally stirred for three hours at room temperature. Then, 300 ml of 1M hydro-chloride solution was added thereto. An organic layer was extracted once therefrom, and was extracted three times additionally therefrom by using each of water and diethyl ether. The obtained organic layer was dried by using MgSO$_4$. A solvent was removed therefrom by evaporation. The obtained residue was separated and purified through a silica gel chromatography to obtain 8.64 g (34.2 mmol) of Intermediate I-2 (yield: 72%). The obtained compound was identified by MS/FAB.

C11H14BClO2Si cal. 252.58, found 252.60.

Synthesis of Intermediate I-3

24.8 g (20.0 mmol) of 2-methoxyphenol and 3 g (60.0 mmol) of a pyridine were dissolved in 60 mL of dichloromethane. Then, 6.0 g (22 mmol) of triflic anhydride were slowly added thereto at 0° C., and the resulting product was allowed to cool down to room temperature and was then stirred for 2 hours. An organic layer was extracted three times therefrom by adding each of 30 mL of water and 50 mL of dichloromethane. The obtained organic layer was dried by using MgSO$_4$. Then, a solvent was removed therefrom by evaporation. The obtained residue was separated and purified through a silica gel chromatography to thereby obtain 47.1 g (18.4 mmol) of Intermediate I-3 (yield: 92%). The obtained compound was identified by MS/FAB.

C8H7F3O4S cal. 256.19, found 256.22.

Synthesis of Intermediate I-4

2.52 g (10 mmol) of Intermediate I-2, 2.82 g (11 mmol) of Intermediate I-3, 1.16 g (7.5 mmol) of Pd(PPh$_3$)$_4$, and 4.15 g (30 mmol) of K$_2$CO$_3$ were added to a 200 ml of mixture of THF/H$_2$O (at a volume ratio of 9:1), and the resulting solution was stirred at 80° C. for 12 hours. The mixture was allowed to cool down to room temperature. Then, an organic layer was extracted three times therefrom by using each of 50 mL of water and 50 mL of diethyl ether. The obtained organic layer was dried by using MgSO$_4$. Then, a solvent was removed therefrom by evaporation. The obtained residue was separated and purified through a silica gel chromatography to obtain 2.36 g (7.5 mmol) of Intermediate I-4 (yield: 75%). The obtained compound was identified by MS/FAB.

C18H19ClOSi cal. 314.88, found 314.90.

Synthesis of Intermediate I-5

2.36 g (7.5 mmol) of Intermediate I-4 and 3.11 g (22.5 mmol) of K$_2$CO$_3$ were dissolved in 200 ml of MeOH/CH$_2$Cl$_2$ (at a volume ratio of 2:1), and the resulting solution was stirred at room temperature for 1 hour. Once the reaction was complete, the obtained compound was filtered by using a filter. An organic solvent was removed from the filtrate by evaporation. Then, an organic layer was extracted therefrom two times by using water and dichloromethane. Then, the resulting organic layer was dried by using MgSO$_4$. The residue obtained by evaporating the solvent was separated and purified through a silica get chromatography to thereby obtain 1.61 g (6.63 mmol) of Intermediate I-5 (yield: 88.5%). The obtained compound was identified by MS/FAB.

C15H11ClO cal. 242.70, found 242.75.

Synthesis of Intermediate I-6

1.61 g (6.63 mmol) of Intermediate I-5 was dissolved in 100 mL of methylene chloride, and was stirred for 30 minutes while maintaining 0° C. in an ice bath. Then, 4.33 g (7.02 mmol) of iodine chloride was added thereto and the resulting solution was stirred for 30 minutes. Once the reaction was complete, an organic layer was extracted therefrom five times by using 100 mL of water, and ethylacetate. Then, the obtained organic layer was dried by using MgSO$_4$, and a solvent was removed therefrom by evaporation. The obtained residue was recrystallized with a mixture solution of methylene chloride and n-hexane to thereby obtain 1.34 g (5.54 mmol) of Intermediate I-6 (yield: 83.5%). The obtained compound was identified by MS/FAB.

C15H11ClO cal. 242.70, found 242.73.

Synthesis of Intermediate I-7

1.34 g (5.54 mmol) of Intermediate I-6 and 4.67 g (27.8 mmol) of sodium ethanethiolate were dissolved in 100 mL of dimethylformamide (DMF), and the resulting solution was stirred at 130° C. 4 hours later, the result was allowed to cool down to room temperature. Then, an organic layer was extracted six times therefrom by using water and ethyl acetate. The obtained organic layer was dried by using MgSO4. Then, a solvent was removed therefrom by evaporation. The obtained residue was separated and purified through a silica gel chromatography to thereby obtain 1.19 g (5.21 mmol) of Intermediate I-7 (yield: 94%). The obtained compound was identified by MS/FAB.

C14H9ClO cal. 228.67, found 228.70.

Synthesis of Intermediate I-8

1.19 g (5.21 mmol) of Intermediate I-7 and 2.24 g (15.6 mmol) of copper (I) oxide were added to 100 mL of nitro-benzene and the resulting solution was stirred at 190° C. for 48 hours. The result was allowed to cool down to room temperature, and then, an organic layer was extracted four times therefrom by using 50 mL of water and 50 mL of diethyl ether. The obtained organic layer was dried by using MgSO4. Then, a solvent was removed therefrom by evaporation. The obtained residue was separated and purified through a silica gel chromatography to thereby obtain 0.93 g (4.11 mmol) of Intermediate I-8 (yield: 79.3%). The obtained compound was identified by MS/FAB.

C14H7ClO cal. 226.65, found 226.71.

Synthesis of Intermediate I-A 0.93 g (4.11 mmol) of Intermediate I-8, 0.28 g (3.00 mmol) of aniline, 0.03 g (0.03 mmol) of Pd2(dba)3, 0.003 g (0.03 mmol) of PtBu3, and 0.86 g (9 mmol) of NaOtBu were dissolved in 30 mL of toluene, and then, the resulting solution was stirred at 85° C. for 4 hours. After allowing the result to cool down to room temperature, an organic layer was extracted three times therefrom by using 30 mL of water and 30 mL of diethyl ether. The obtained organic layer was dried by using MgSO4. A solvent was removed therefrom by evaporation. The obtained residue was separated and purified through a silica gel chromatography to obtain 0.61 g (2.16 mmol) of Intermediate I-A (yield: 72%). The obtained compound was identified by MS/FAB.

C20H13NO cal. 283.33, found 283.35.

Synthesis of Intermediate 8-1

3.6 g (20.0 mmol) of 1,6-dibromopyrene, 0.38 g (2.0 mmol) of CuI, and 6.7 g (120.0 mmol) of KOH were dissolved in 100 mL of mixture solution of toluene/PEG400/H2O (at a volume ratio of 5:4:1) under N2 atmosphere, and the resulting solution was stirred for 8 hours while heating up to maintain 110° C. The result was allowed to cool down to room temperature, and then, 10 mL of 1N HCl was added thereto to adjust pH to be in a range of about 2 to about 3. Then, an organic layer was extracted three times therefrom by using 60 mL of ethyl acetate. The obtained organic layer was dried by using MgSO4. Then, a solvent was removed therefrom by evaporation. The obtained residue was separated and purified through a silica gel chromatography to thereby obtain 3.8 g (12.8 mmol) of Intermediate 8-1 (yield: 64%). The obtained compound was identified by MS/FAB.

C16H9BrO cal. 297.15, found 297.21.

Synthesis of Intermediate 8-2

2.97 g (10.0 mmol) of Intermediate 8-1, 3.11 g (11.0 mmol) of Intermediate I-A, 0.18 g (0.2 mmol) of Pd2(dba)3, 0.04 g (0.2 mmol) of PtBu3, and 1.9 g (20.0 mmol) of NaOtBu were dissolved in 30 mL of toluene, and then the resulting solution was stirred at 85° C. for 4 hours. After allowing the result to cool down to room temperature, an organic layer was extracted three times therefrom by using 30 mL of water and 30 mL of diethyl ether. The obtained organic layer was dried by using MgSO4. A solvent was removed therefrom by evaporation. The obtained residue was separated and purified through a silica gel chromatography to obtain 4.68 g (7.2 mmol) of Intermediate 8-2 (yield: 72%). The obtained compound was identified by MS/FAB.

C36H21NO2 cal. 499.56, found 499.61.

Synthesis of Intermediate 8-3

4.27 g (6.77 mmol) of Intermediate 8-3 (yield: 94%) was obtained in the same (or substantially the same) manner as in Synthesis of Intermediate I-3 except that Intermediate 8-2 was used instead of 2-methoxyphenol. The obtained compound was identified by MS/FAB.

C37H20F3NO4S cal. 631.62, found 631.66.

Synthesis of Compound 8

4.28 g (6.77 mmol) of Intermediate 8-3, 1.84 g (7.11 mmol) of Compound 8-A, 0.06 g (0.07 mmol) of Pd2(dba)3, 0.01 g (0.07 mmol) of PtBu3, and 0.97 g (10.2 mmol) of NaOtBu were dissolved in 30 mL of toluene, and then the resulting solution was stirred at 85° C. for 4 hours. After allowing the result to cool down to room temperature, an organic layer was extracted three times therefrom by using 30 mL of water and 30 mL of diethyl ether. The obtained organic layer was dried by using MgSO4. Then, a solvent was removed therefrom by evaporation. The obtained residue was separated and purified through a silica gel chromatography to thereby obtain 4.31 g (5.82 mmol) of Compound 8 (yield: 86%). The obtained compound was identified by MS/FAB and $_1$H NMR.

C55H36N2O cal. 740.90, found 740.92.

$^1$H NMR (400 MHz, CDCl3) ** 7.93-7.48 (m, 16H), 7.13-6.51 (m, 15H), 6.29-6.27 (m, 2H), 1.86 (s, 3H)

Synthesis Example 2

Synthesis of Compound 14

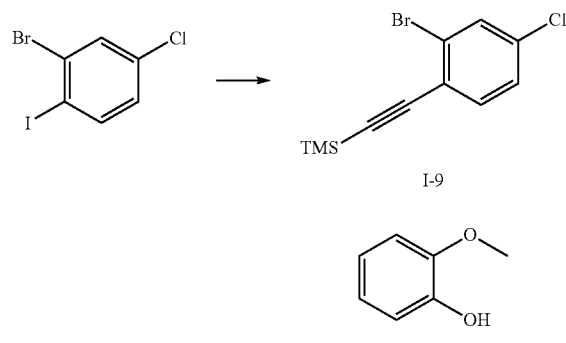

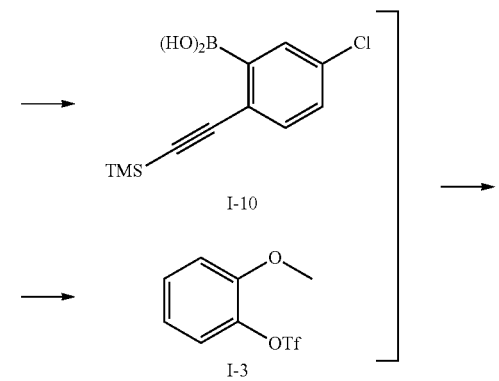

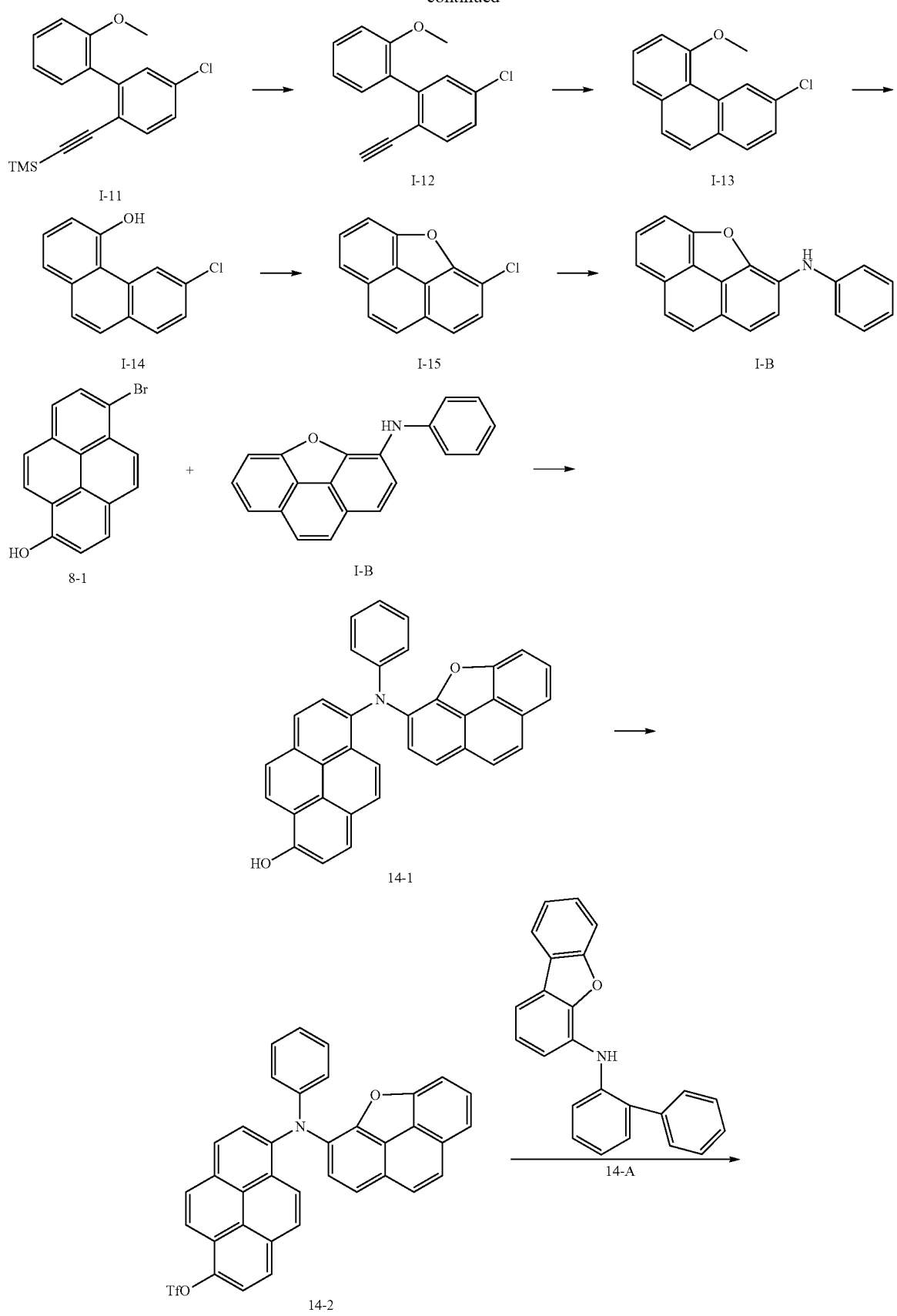

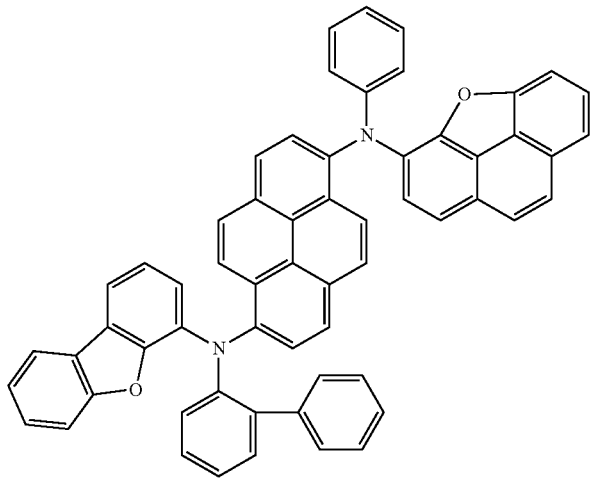

14

Synthesis of Intermediate I-9

12.8 g (45 mmol) of Intermediate I-9 (yield: 86%) was obtained in the same (or substantially the same) manner as in Synthesis of Intermediate I-1 except that 2-bromo-4-chloro-1-iodobenzene was used instead of 1-bromo-4-chloro-2-iodobenzene. The obtained compound was identified by MS/FAB.

C11H12BrClSi cal. 287.66, found 287.69.

Synthesis of Intermediate I-10

8.51 g (33.8 mmol) of Intermediate I-10 (yield: 75%) was obtained in the same (or substantially the same) manner as in Synthesis of Intermediate I-2 except that Intermediate I-9 was used instead of Intermediate I-1. The obtained compound was identified by MS/FAB.

C11H14BClO2Si cal. 252.57, found 252.62.

Synthesis of Intermediate I-11

6.58 g (20.9 mmol) of Intermediate I-11 (yield: 62%) was obtained in the same (or substantially the same) manner as in Synthesis of Intermediate I-4 except that Intermediate I-10 was used instead of Intermediate I-2. The obtained compound was identified by MS/FAB.

C18H19ClOSi cal. 314.88, found 314.96.

Synthesis of Intermediate I-12

4.60 g (19.0 mmol) of Intermediate I-12 (yield: 91%) was obtained in the same (or substantially the same) manner as in Synthesis of Intermediate I-5 except that Intermediate I-11 was used instead of Intermediate I-4. The obtained compound was identified by MS/FAB.

C15H11ClO cal. 242.70, found 242.73.

Synthesis of Intermediate I-13

3.63 g (15.0 mmol) of Intermediate I-13 (yield: 79%) was obtained in the same (or substantially the same) manner as in Synthesis of Intermediate I-6 except that Intermediate I-12 was used instead of Intermediate I-5. The obtained compound was identified by MS/FAB.

C15H11ClO cal. 242.70, found 242.74.

Synthesis of Intermediate I-14

2.91 g (12.8 mmol) of Intermediate I-14 (yield: 85%) was obtained in the same (or substantially the same) manner as in Synthesis of Intermediate I-7 except that Intermediate I-13 was used instead of Intermediate I-6. The obtained compound was identified by MS/FAB.

C14H9ClO cal. 228.67, found 228.72.

Synthesis of Intermediate I-15

2.35 g (10.4 mmol) of Intermediate I-15 (yield: 81.1%) was obtained in the same (or substantially the same) manner as in Synthesis of Intermediate I-8 except that Intermediate I-14 was used instead of Intermediate I-7. The obtained compound was identified by MS/FAB.

C14H7ClO cal. 226.66, found 226.68.

Synthesis of Intermediate I-B 2.53 g (8.94 mmol) of Intermediate I-B (yield: 86%) was obtained in the same (or substantially the same) manner as in Synthesis of Intermediate I-A except that Intermediate I-15 was used instead of Intermediate I-8. The obtained compound was identified by MS/FAB.

C20H13NO cal. 283.33, found 283.37.

Synthesis of Intermediate 14-1

2.35 g (5.8 mmol) of Intermediate 14-1 (yield: 79.5%) was obtained in the same (or substantially the same) manner as in Synthesis of Intermediate 8-2 except that Intermediate I-B was used instead of Intermediate I-A. The obtained compound was identified by MS/FAB.

C36H21NO2 cal. 499.57, found 499.60.

Synthesis of Intermediate 14-2

3.44 g (5.45 mmol) of Intermediate 14-2 (yield: 94%) was obtained in the same (or substantially the same) manner as in Synthesis of Intermediate I-3 except that Intermediate 14-1 was used instead of 2-methoxyphenol. The obtained compound was identified by MS/FAB.

C37H20F3NO4S cal. 631.62, found 631.65.

Synthesis of Compound 14

3.17 g (3.87 mmol) of Compound 14 (yield: 71%) was obtained in the same (or substantially the same) manner as in Synthesis of Compound 8 except that Intermediate 14-2 was used instead of Intermediate 8-3, and Compound 14-A was used instead of Compound 8-A. The obtained compound was identified by MS/FAB and $_1$H NMR.

C60H36N2O2 cal. 816.96, found 816.99.

$^1$H NMR (400 MHz, CDCl$_3$) □□ 7.98-7.42 (m, 22H), 7.42-6.85 (m, 11H), 6.63-6.61 (m, 1H), 6.29-6.27 (m, 2H)

Synthesis Example 3
Synthesis of Compound 21
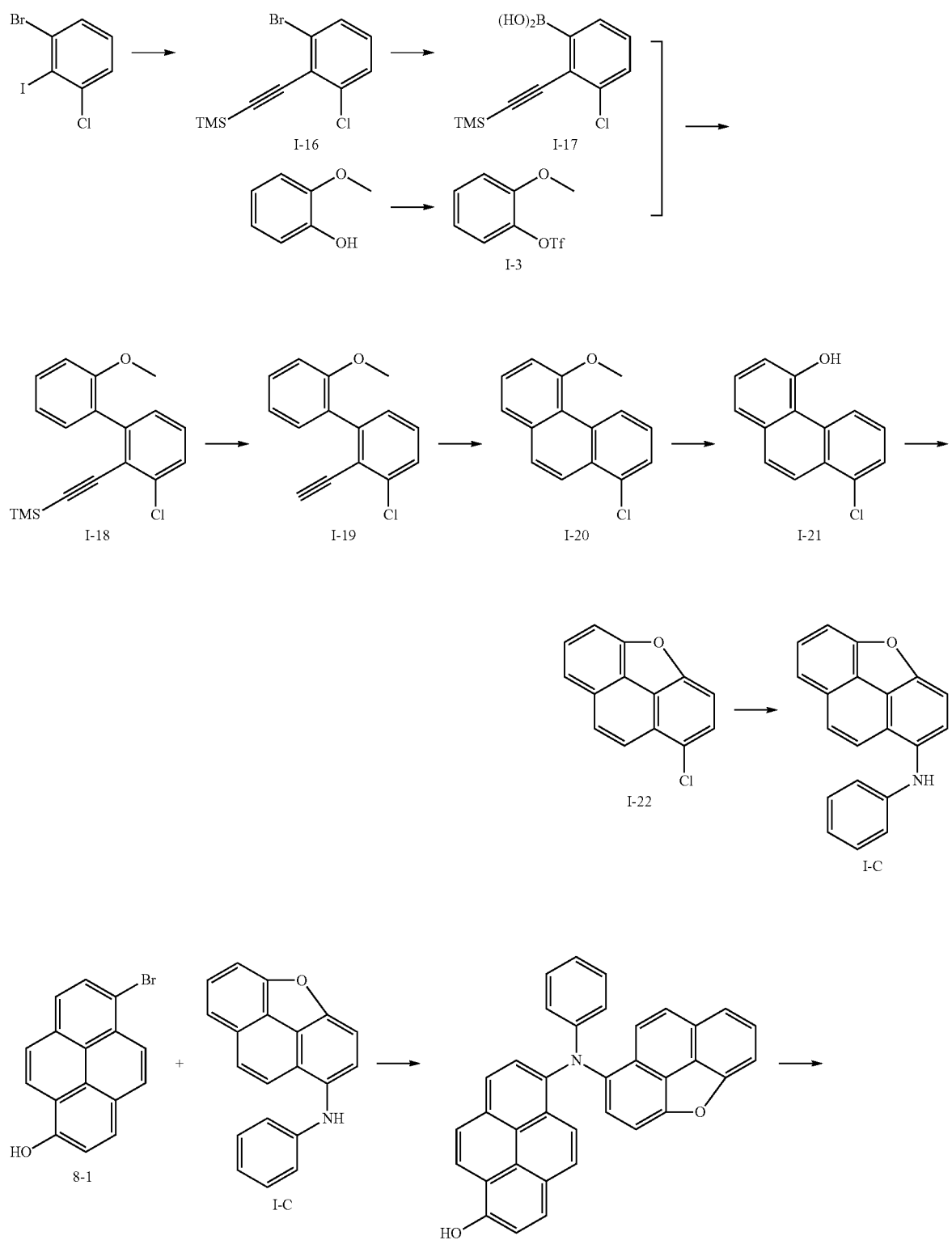

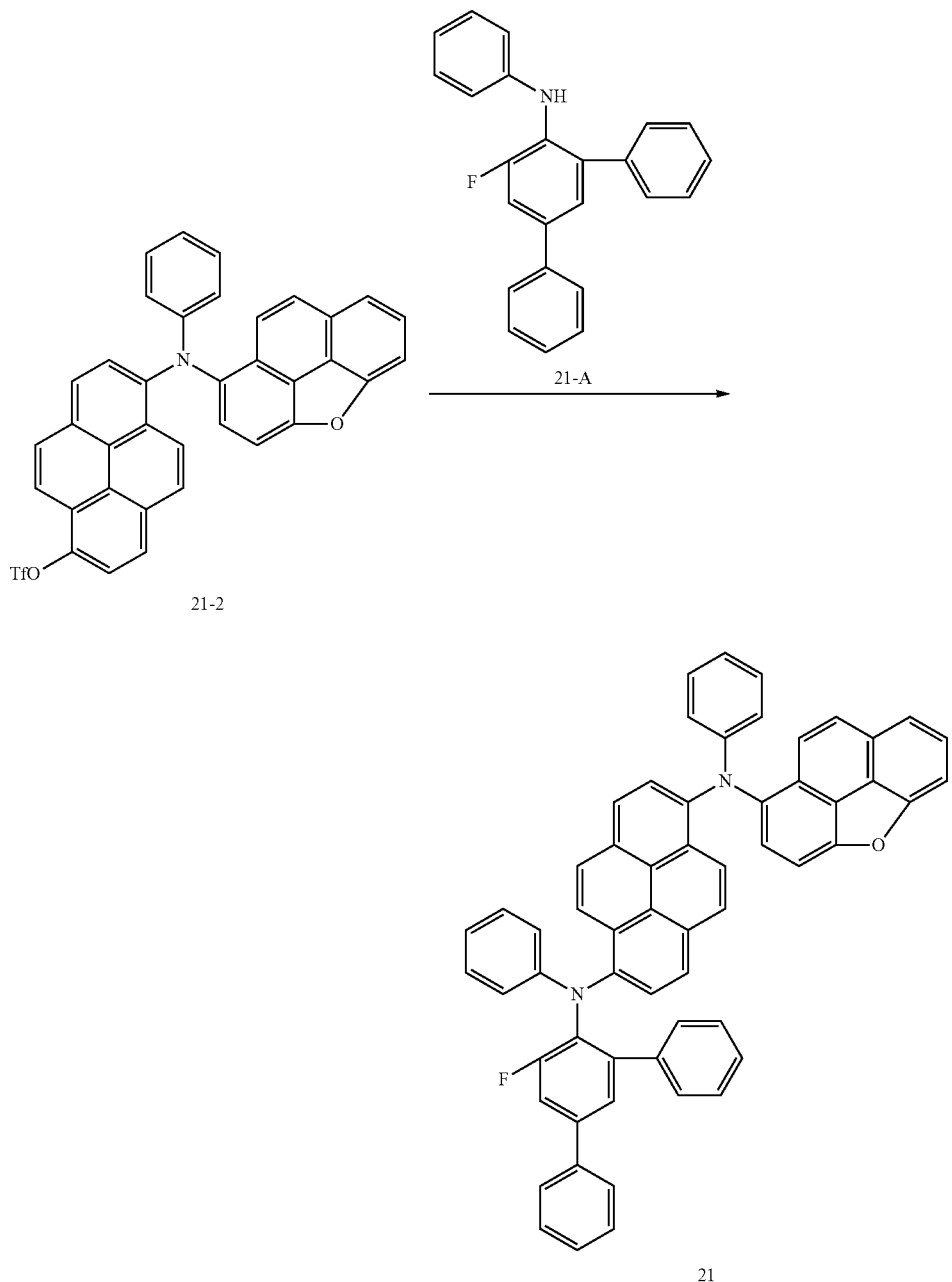

Synthesis of Intermediate I-16

10.3 g (36 mmol) of Intermediate I-16 (yield: 82%) was obtained in the same (or substantially the same) manner as in Synthesis of Intermediate I-1 except that 1-bromo-3-chloro-2-iodobenzene was used instead of 1-bromo-4-chloro-2-iodobenzene.

The obtained compound was identified by MS/FAB.

C11H12BrClSi cal. 287.66, found 287.69.

Synthesis of Intermediate I-17

7.17 g (28.4 mmol) of Intermediate I-17 (yield: 79%) was obtained in the same (or substantially the same) manner as in Synthesis of Intermediate I-2 except that Intermediate I-16 was used instead of Intermediate I-1. The obtained compound was identified by MS/FAB.

C11H14BClO2Si cal. 252.57, found 252.62.

Synthesis of Intermediate I-18

5.89 g (18.7 mmol) of Intermediate I-18 (yield: 66%) was obtained in the same (or substantially the same) manner as in Synthesis of Intermediate I-4 except that Intermediate I-17 was used instead of Intermediate I-2. The obtained compound was identified by MS/FAB.

C18H19ClOSi cal. 314.88, found 314.96.

Synthesis of Intermediate I-19

4.30 g (17.8 mmol) of Intermediate I-19 (yield: 95%) was obtained in the same (or substantially the same) manner as in Synthesis of Intermediate I-5 except that Intermediate I-18 was used instead of Intermediate I-4. The obtained compound was identified by MS/FAB.

C15H11ClO cal. 242.70, found 242.73.

Synthesis of Intermediate I-20

2.97 g (12.3 mmol) of Intermediate I-20 (yield: 69%) was obtained in the same (or substantially the same) manner as in Synthesis of Intermediate I-6 except that Intermediate I-19 was used instead of Intermediate I-5. The obtained compound was identified by MS/FAB.

C15H11ClO cal. 242.70, found 242.74.

Synthesis of Intermediate I-21

2.53 g (11.1 mmol) of Intermediate I-21 (yield: 90%) was obtained in the same (or substantially the same) manner as in Synthesis of Intermediate I-7 except that Intermediate I-20 was used instead of Intermediate I-6. The obtained compound was identified by MS/FAB.

C14H9ClO cal. 228.67, found 228.72.

Synthesis of Intermediate I-22

1.91 g (8.44 mmol) of Intermediate I-22 (yield: 76%) was obtained in the same (or substantially the same) manner as in Synthesis of Intermediate I-8 except that Intermediate I-21 was used instead of Intermediate I-7. The obtained compound was identified by MS/FAB.

C14H7ClO cal. 226.66, found 226.68.

Synthesis of Intermediate I-C 1.94 g (6.84 mmol) of Intermediate I-C (yield: 81%) was obtained in the same (or substantially the same) manner as in Synthesis of Intermediate I-A except that Intermediate I-22 was used instead of Intermediate I-8. The obtained compound was identified by MS/FAB.

C20H13NO cal. 283.33, found 283.37.

Synthesis of Intermediate 21-1

2.50 g (5.0 mmol) of Intermediate 21-1 (yield: 77%) was obtained in the same (or substantially the same) manner as in Synthesis of Intermediate 8-2 except that Intermediate I-C was used instead of Intermediate I-A. The obtained compound was identified by MS/FAB.

C36H21NO2 cal. 499.57, found 499.60.

Synthesis of Intermediate 21-2

2.97 g (4.70 mmol) of Intermediate 21-2 (yield: 94%) was obtained in the same (or substantially the same) manner as in Synthesis of Intermediate I-3 except that Intermediate 21-1 was used instead of 2-methoxyphenol. The obtained compound was identified by MS/FAB.

C37H20F3NO4S cal. 631.62, found 631.65.

Synthesis of Compound 21

2.74 g (3.34 mmol) of Compound 21 (yield: 71%) was obtained in the same (or substantially the same) manner as in Synthesis of Compound 8 except that Intermediate 21-2 was used instead of Intermediate 8-3, and Compound 21-A was used instead of Compound 8-A. The obtained compound was identified by MS/FAB and $_1$H NMR.

C60H37FN2O cal. 820.96, found 820.99.

$^1$H NMR (400 MHz, CDCl$_3$) □□ 7.84-7.32 (m, 24H), 7.11-7.00 (m, 6H), 6.82-6.80 (m, 1H), 6.59-6.55 (m, 2H), 6.17-6.12 (m, 4H)

Synthesis Example 4

Synthesis of Compound 31

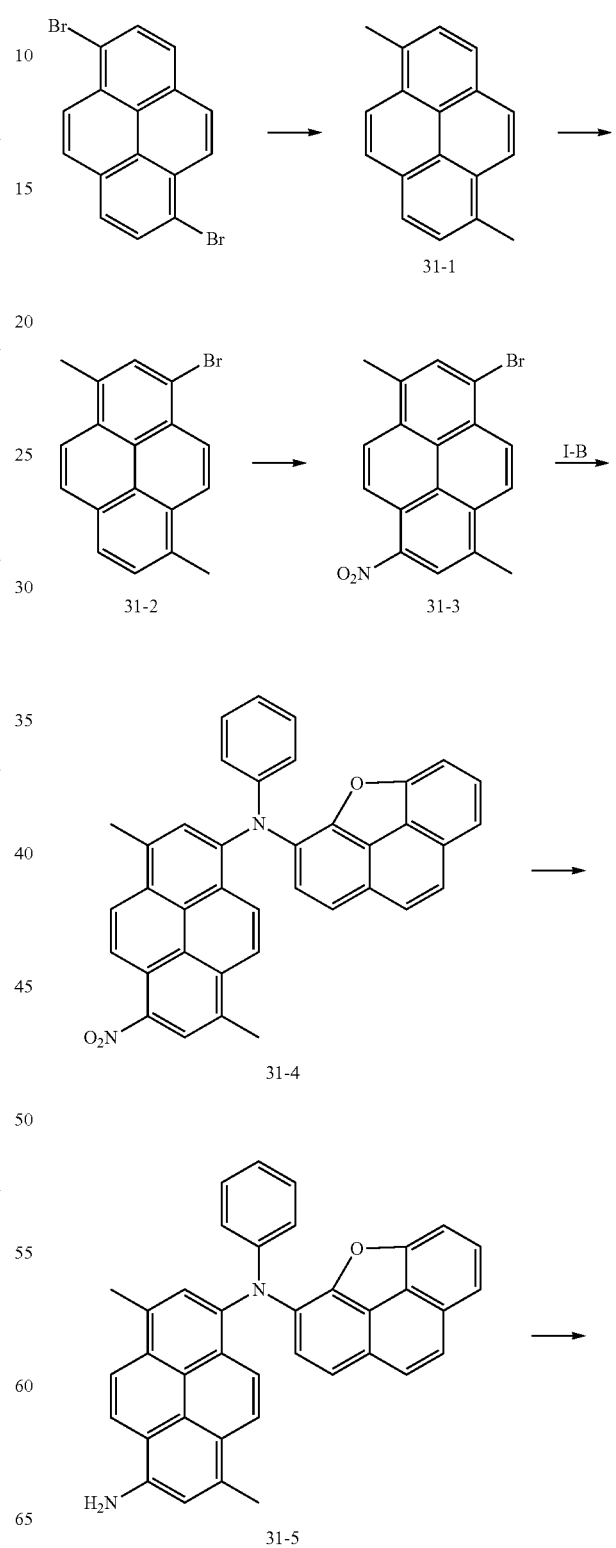

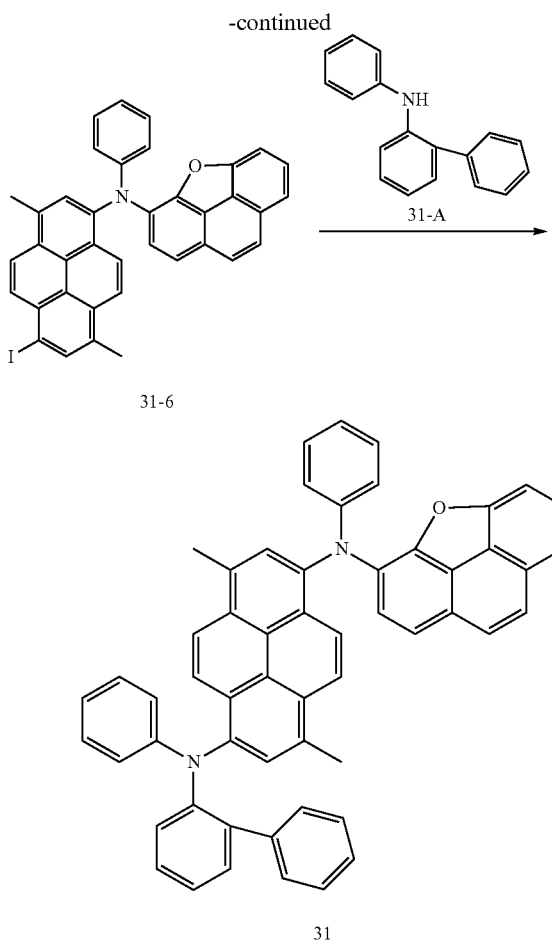

Synthesis of Intermediate 31-1

7.2 g (20.0 mmol) of 1,6-dibromopyrene was dissolved in 60 mL of THF, and was cooled to −78° C. 48.0 mL of n-BuLi (2.5M in hexane) was slowly added thereto, and the resulting solution was heated up to −30° C., and then was stirred. 1 hour later, the result was cooled to −78° C. 7.5 mL of iodomethane was slowly added thereto, and the resulting solution was stirred at room temperature for 4 hours. An organic layer was extracted three times therefrom by using 60 mL of water and 60 mL of diethyl ether. The obtained organic layer was dried by using MgSO$_4$. Then, a solvent was removed therefrom by evaporation. The obtained residue was separated and purified through a silica gel chromatography to thereby obtain 2.99 g (13 mmol) of Intermediate 31-1 (yield: 65%). The obtained compound was identified by MS/FAB.

C18H14 cal. 230.31, found 230.35.

Synthesis of Intermediate 31-2

2.9 g (12.6 mmol) of Intermediate 31-1 was dissolved in 30 mL of a mixture solution of diethyl ether/methanol (at a volume ratio of 2.5:1). 3.8 mL of HBr (33 wt % in AcOH) was slowly added thereto at 0° C., and the resulting solution was stirred for 30 minutes. 1.73 mL of hydrogenperoxide (30 wt % in H$_2$O) was slowly added to the resulting solution at the same temperature, and the obtained solution was stirred at room temperature for 8 hours. Once the reaction was complete, an organic layer was extracted three times therefrom by using 30 mL of water and 30 mL of diethyl ether. The obtained organic layer was dried by using MgSO$_4$. Then, a solvent was removed therefrom by evaporation. The obtained residue was separated and purified through a silica gel chromatography to thereby obtain 3.58 g (11.6 mmol) of Intermediate 31-2 (yield: 92%). The obtained compound was identified by MS/FAB.

C18H13Br cal. 309.21, found 309.26.

Synthesis of Intermediate 31-3

3.5 g (11.3 mmol) of Intermediate 31-2 was dissolved in 30 mL of dichloromethane, and then, a solution of 0.85 g (12.4 mmol) of NaNO$_2$ dissolved in 10 mL of trifluoroacetic acid was slowly added thereto, and the resulting solution was stirred at 0° C. for 30 minutes. 10 mL of triethylamine was then added to the resulting solution in order to complete the reaction. Then, the formed solid was filtered. Then, an organic layer was extracted three times therefrom by using 40 mL of water and 30 mL of dichloromethane. The obtained organic layer was dried by using MgSO$_4$. Then, a solvent was removed therefrom by evaporation. The obtained residue was separated and purified through a silica gel chromatography to thereby obtain 2.88 g (8.14 mmol) of Intermediate 31-3 (yield: 72%). The obtained compound was identified by MS/FAB.

C18H12BrNO2 cal. 354.20, found 354.24.

Synthesis of Intermediate 31-4

2.86 g (8.1 mmol) of Intermediate 31-3, 2.75 g (9.72 mmol) of Intermediate I-B, 0.15 g (0.17 mmol) of Pd$_2$(dba)$_3$, 0.03 g (0.17 mmol) of PtBu$_3$, and 1.2 g (12.5 mmol) of NaOtBu were dissolved in 30 mL of toluene, and then the resulting solution was stirred at 85° C. for 4 hours. After allowing the result to cool down to room temperature, an organic layer was extracted three times therefrom by using each of 30 mL of water and 30 mL of diethyl ether. The obtained organic layer was dried by using MgSO$_4$. Then, a solvent was removed therefrom by evaporation. The obtained residue was separated and purified through a silica gel chromatography to thereby obtain 3.38 g (6.08 mmol) of Intermediate 31-4 (yield: 75%). The obtained compound was identified by MS/FAB.

C38H24N2O3 cal. 556.62, found 556.66.

Synthesis of Intermediate 31-5

3.38 g (6.08 mmol) of Intermediate 31-4 was dissolved in 20 mL of a mixture solution of dichloromethane/methanol (at a volume ratio of 1:1). Then, 0.5 g of Pd/C was added thereto, and the resulting solution was stirred in a reaction vessel while introducing hydrogen gas into the reaction vessel at 1 atm for 3 hours. Once the reaction was complete, the resulting solution was filtrated by using a celite. The obtained organic layer was dried by using MgSO$_4$. Then, a solvent was removed therefrom by evaporation. The obtained residue was separated and purified through a silica gel chromatography to thereby obtain 2.85 g (5.41 mmol) of Intermediate 31-5 (yield: 89%). The obtained compound was identified by MS/FAB.

C38H26N2O3 cal. 526.63, found 526.67.

Synthesis of Intermediate 31-6

2.85 g (5.41 mmol) of Intermediate 31-5 was dissolved in 15 mL of acetonitrile. Then, 16 mL of 1N HCl was added slowly thereto at 0° C. The resulting solution was stirred at the same temperature for 30 minutes. NaNO$_2$ 0.92 g (13.3 mmol) was slowly added thereto, and the obtained solution was stirred for additional 30 minutes. 8 g (48 mmol) of potassium iodide (KI) was added to the resulting solution, and the obtained reaction mixture was stirred for 2 hours. 20 mL of saturated NaHCO$_3$ solution was added to the reaction mixture. Then, an organic layer was extracted three times therefrom by using 30 mL of ethyl acetate. The obtained organic layer was dried by using MgSO$_4$. Then, a solvent was removed therefrom by evaporation. The obtained residue was separated and purified through a silica gel chromatography to thereby obtain 2.10 g (3.30 mmol) of Intermediate 31-6 (yield: 61%). The obtained compound was identified by MS/FAB.

C38H24INO cal. 637.52, found 637.55.

Synthesis of Compound 31

1.97 g (3.1 mmol) of Intermediate 31-6, 0.88 g (3.6 mmol) of Compound 31-A, 0.05 g (0.06 mmol) of Pd$_2$(dba)$_3$, 0.01 g (0.06 mmol) of PtBu$_3$, and 0.44 g (4.6 mmol) of NaOtBu were dissolved in 20 mL of toluene, and then the resulting solution was stirred at 85° C. for 4 hours. After allowing the result to cool down to room temperature, an organic layer was extracted three times therefrom by using each of 20 mL of water and 20 mL of diethyl ether. The obtained organic layer was dried by using MgSO$_4$. Then, a solvent was removed therefrom by evaporation. The obtained residue was separated and purified through a silica gel chromatography to thereby obtain 1.94 g (2.57 mmol) of Compound 31 (yield: 83%). The obtained compound was identified by MS/FAB and $_1$H NMR.

C38H24INO cal. 754.93, found 754.96.

$^1$H NMR (400 MHz, CDCl$_3$) 8.09 (d, 1H), 7.98 (d, 1H), 7.78-7.45 (m, 13H), 7.25-7.00 (m, 9H), 6.82 (d, 1H), 6.63-6.55 (m, 3H), 6.28-6.26 (m, 2H), 6.04-6.02 (m, 2H), 2.57 (s, 6H)

Synthesis Example 5

Synthesis of Compound 42

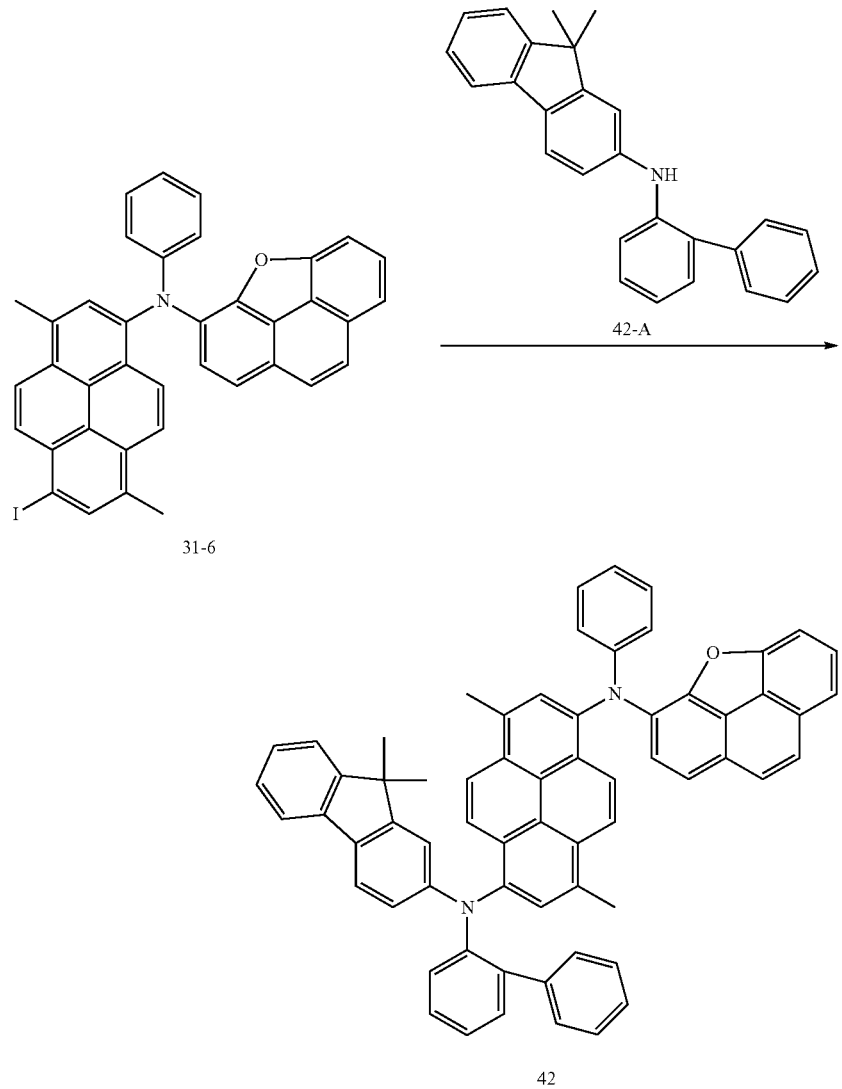

2.65 g (3.04 mmol) of Compound 42 (yield: 79%) was obtained in the same (or substantially the same) manner as in Synthesis of Compound 31 except that Compound 42-A was used instead of Compound 31-A. The obtained compound was identified by MS/FAB and $_1$H NMR.

C65H46N2O cal. 871.09, found 871.14.

$^1$H NMR (400 MHz, CDCl$_3$) 8.00 (d, 1H), 7.97 (d, 1H), 7.78-7.70 (m, 6H), 7.65-7.43 (m, 8H), 7.36-7.30 (m, 2H), 7.21 (d, 1H), 7.15-6.93 (m, 9H), 6.63-6.55 (m, 3H), 6.30-6.24 (m, 3H), 6.06 (s, 1H), 2.57 (s, 6H), 1.61 (s, 6H)

Synthesis Example 6

Synthesis of Compound 48

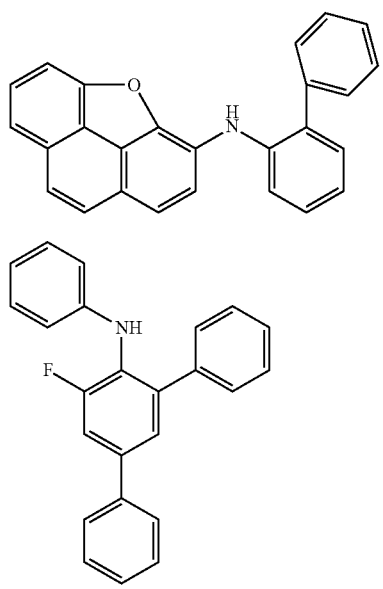

3.10 g (3.46 mmol) of Compound 48 (yield: 71%) was obtained in the same (or substantially the same) manner as in Synthesis of Compound 8 except that Intermediate I-D was used instead of Intermediate I-A, and Compound 48-A was used instead of Compound 8-A. The obtained compound was identified by MS/FAB and $_1$H NMR.

C66H41FN2O cal. 897.06, found 897.12.

$^1$H NMR (400 MHz, CDCl$_3$) 7.91-7.30 (m, 28H), 7.13-6.89 (m, 8H), 6.76-6.61 (m, 3H), 6.10-6.08 (m, 2H)

Synthesis Example 7

Synthesis of Compound 55

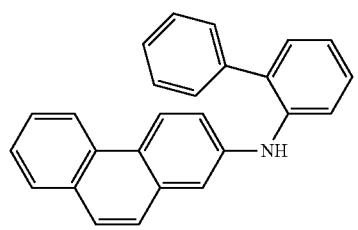

2.50 g (3.02 mmol) of Compound 55 (yield: 78%) was obtained in the same (or substantially the same) manner as in Synthesis of Compound 14 except that Compound 55-A was used instead of Compound 14-A. The obtained compound was identified by MS/FAB and $_1$H NMR.

C62H38N2O cal. 826.99, found 827.03.

$^1$H NMR (400 MHz, CDCl$_3$) 8.46 (d, 1H), 7.98-7.45 (m, 22H), 7.16-6.67 (m, 10H), 6.63-6.60 (m, 2H), 6.29-6.27 (m, 2H)

Synthesis Example 8

Synthesis of Compound 60

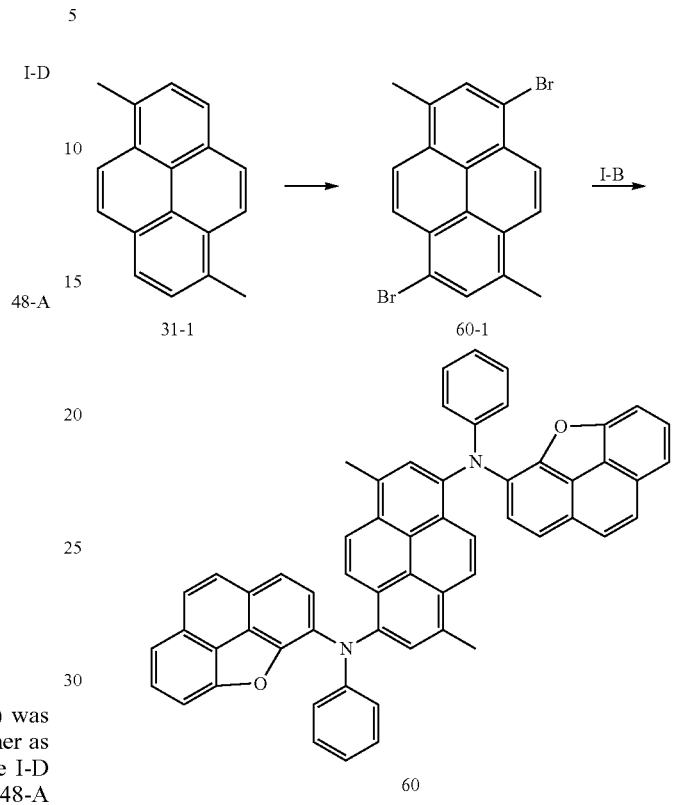

Synthesis of Intermediate 60-1

2.9 g (12.6 mmol) of Compound 31-1 was dissolved in 30 mL of a mixture solution of diethyl ether/methanol (at a volume ratio of 2.5:1). 7.6 mL of HBr (33 wt % in AcOH) was slowly added thereto at 0° C., and the resulting solution was stirred for 30 minutes. 3.4 mL of hydrogenperoxide (30 wt % in H$_2$O) was slowly added to the resulting solution at the same temperature, and the mixture was stirred at room temperature for 8 hours. Once the reaction was complete, an organic layer was extracted three times therefrom by using each of 30 mL of water and 30 mL of diethyl ether. The obtained organic layer was dried by using MgSO$_4$. Then, a solvent was removed therefrom by evaporation. The obtained residue was separated and purified through a silica gel chromatography to thereby obtain 4.11 g (10.6 mmol) of Intermediate 60-1 (yield: 84%). The obtained compound was identified by MS/FAB.

C18H12Br2 cal. 388.10, found 388.22.

Synthesis of Compound 60

2.08 g (2.62 mmol) of Compound 60 (yield: 81%) was obtained in the same (or substantially the same) manner as in Synthesis of Intermediate 31-4 except that Intermediate 60-1 was used instead of Intermediate 31-3. The obtained compound was identified by MS/FAB and $_1$H NMR.

C58H36N2O2 cal. 792.93, found 792.95.

$^1$H NMR (400 MHz, CDCl$_3$) 8.11-8.09 (m, 2H), 7.76-7.49 (m, 14H), 7.23-7.21 (m, 2H), 7.06-7.00 (m, 6H), 6.63-6.60 (m, 2H), 6.28-6.20 (m, 4H), 2.57 (m, 6H),

Synthesis Example 8

Synthesis of Compound 72

3.11 g (3.39 mmol) of Compound 72 (yield: 72%) was obtained in the same (or substantially the same) manner as in Synthesis of Intermediate 31-4 except that 1,6-dibromopyrene was used instead of Intermediate 31-3, and Intermediate I-D was used instead of Intermediate I-B. The obtained compound was identified by MS/FAB and $_1$H NMR.

C68H40N2O2 cal. 917.08, found 917.13.

$^1$H NMR (400 MHz, CDCl$_3$) 7.96-7.94 (m, 2H), 7.78-7.30 (m, 26H), 7.20-7.15 (m, 6H), 7.01-6.97 (m, 6H)

The following Compounds were prepared and identified by $^1$H NMR and MS/FAB. The results thereof are shown in Table 1.

Methods of synthesizing compounds other than Compounds shown in Table 1 should be apparent to those skilled in the art by referring to the synthesis pathways and raw materials described in Synthesis Examples 1 to 8.

Example 1

A Corning 15 Ohms per square centimeter (Ω/cm$_2$) (1200 Å) ITO glass substrate was cut to a size of 50 millimeters (mm)×50 mm×0.7 mm, sonicated in isopropyl alcohol and pure water, for 5 minutes in each solvent, and cleaned by exposure to ultraviolet rays with ozone so as to use the glass substrate as an anode. Then, the obtained glass substrate was mounted in a vacuum-deposition apparatus. 4,4'-Bis[N-phenyl-N-(9-phenylcarbazol-3-yl)amino]-1,1'-biphenyl (Compound 301) was first vacuum-deposited on the substrate as a hole injection layer having a thickness of about 600 Å. Then, a hole transporting compound (N-[1,1'-biphenyl]-4-yl-9,9-dimethyl-N-[4-(9-phenyl-9H-carbazol-3-yl)phenyl]-9H-fluorene-2-amine (Compound 311)) was vacuum-deposited on the hole injection layer to form a hole transport layer having a thickness of about 300 Å.

TABLE 1

| Compound | $^1$H NMR (CDCl$_3$, 400 MHz) | MS/FAB found | MS/FAB calc. |
|---|---|---|---|
| 1 | δ = 7.93-7.90 (m, 2H), 7.80-7.70 (m, 3H), 7.52-7.47 (m, 7H), 7.14-7.02 (m, 8H), 6.71-6.61 (m, 4H), 6.29-6.27 (m, 2H), 6.14-6.10 (m, 4H) | 650.80 | 650.78 |
| 4 | δ = 7.97 (d, 1H), 7.90 (d, 1H), 7.78-7.74 (m, 3H), 7.65-7.45 (m, 7H), 7.40-7.32 (m, 5H), 7.23-7.15 (m, 3H), 7.06-7.01 (m, 2H), 6.65-6.62 (m, 1H), 6.56-6.50 (m, 5H), 6.20-6.12 (m, 2H), 0.24 (s, 9H), 0.27 (s, 9H) | 795.16 | 795.14 |
| 12 | δ = 7.98-7.70 (m, 3H), 7.55-7.48 (m, 5H), 7.35-7.07 (m, 22H), 6.53-6.50 (m, 2H), 6.32-6.29 (m, 3H), 6.25-6.20 (m, 1H), 1.61 (s, 6H) | 843.06 | 843.04 |
| 16 | δ = 7.96-7.30 (m, 22H), 7.11-7.07 (m, 8H), 6.71-6.65 (m, 3H), 6.29-6.25 (m, 2H), 6.08-6.05 (m, 2H) | 820.97 | 820.96 |
| 20 | δ = 8.11-7.75 (m, 9H), 7.70-7.35 (m, 13H), 7.29-6.97 (m, 10H), 6.67-6.60 (m, 2H), 6.29-6.25 (m, 2H) | 833.04 | 833.02 |
| 23 | δ = 7.99 (d, 1H), 7.85-7.75 (m, 5H), 7.66-7.39 (m, 17H), 7.30-6.82 (m, 10H), 6.63-6.61 (m, 1H), 6.04-6.02 (m, 2H) | 816.99 | 816.96 |
| 29 | δ = 8.01-7.70 (m, 7H), 7.48-7.45 (m, 2H), 7.32 (d, 1H), 7.05-7.00 (m, 8H), 6.83 (d, 1H), 6.64-6.62 (m, 3H), 6.15-6.10 (m, 6H), 2.57 (s, 6H) | 772.29 | 772.29 |
| 34 | δ = 7.91 (d, 1H), 7.85-7.68 (m, 4H), 7.60-7.43 (m, 11H), 7.40-7.37 (m, 2H), 7.20-7.09 (m, 4H), 7.04-6.95 (m, 4H), 6.83 (d, 1H), 6.69-6.59 (m, 4H), 6.04-6.02 (m, 2H), 0.24 (s, 9H) | 799.07 | 799.06 |
| 38 | δ = 8.32-8.30 (m, 2H), 8.04-7.96 (m, 2H), 7.80-7.68 (m, 3H), 7.60-7.45 (m, 11H), 7.34 (d, 1H), 7.20-7.11 (m, 3H), 7.06-6.97 (m, 7H), 6.82-6.79 (m, 2H), 6.74-6.63 (m, 2H), 6.63-6.60 (m, 1H), 6.03-6.00 (m, 2H), 1.48 (s, 18H) | 915.21 | 915.19 |
| 40 | δ = 7.93-7.70 (m, 5H), 7.52-7.39 (m, 13H), 7.16-7.00 (m, 8H), 6.79-6.63 (m, 5H), 6.04-6.02 (m, 2H), | 751.90 | 751.88 |
| 44 | δ = 7.93-7.30 (m, 22H), 7.07-7.00 (m, 5H), 6.74-6.52 (m, 5H), 6.10-6.08 (m, 2H), 2.28 (s, 3H), 2.15 (s, 6H) | 863.10 | 863.04 |
| 49 | δ = 7.93-7.41 (m, 22H), 7.18-7.06 (m, 7H), 6.80-6.69 (m, 5H), 6.27-6.20 (m, 4H) | 802.99 | 802.97 |
| 62 | δ = 8.45-8.43 (m, 2H), 8.27-8.25 (m, 2H), 7.78-7.75 (m, 6H), 7.68-7.63 (m, 4H), 7.48-7.46 (m, 2H), 7.23-7.21 (m, 2H), 7.09-7.02 (m, 6H), 6.63-6.59 (m, 2H), 6.27-6.23 (m, 4H), 0.41 (s, 18H) | 909.27 | 909.25 |
| 67 | δ = 8.08-7.99 (m, 6H), 7.64-7.58 (m, 6H), 7.50-7.43 (m, 12H), 7.18-7.04 (m, 8H), 6.73-6.70 (m, 4H), 6.32-6.28 (m, 4H) | 917.10 | 917.08 |
| 70 | δ = 8.00-7.98 (m, 2H), 7.90-7.84 (m, 2H), 7.78-7.71 (m, 7H), 7.67-7.54 (m, 6H), 7.48-7.40 (m, 3H), 7.33-7.30 (m, 1H), 7.11-7.09 (m, 2H), 7.06-7.01 (m, 4H), 6.67-6.59 (m, 2H), 6.46-6.44 (m, 1H), 6.29-6.27 (m, 2H), 1.61 (s, 6H) | 881.07 | 881.04 |

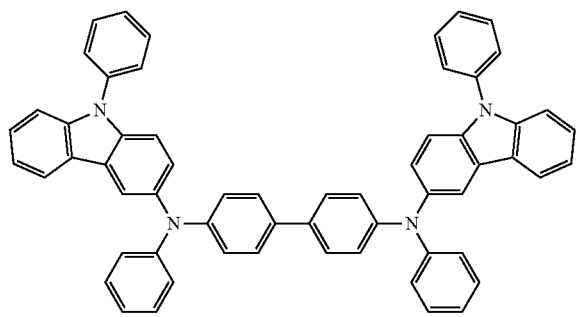

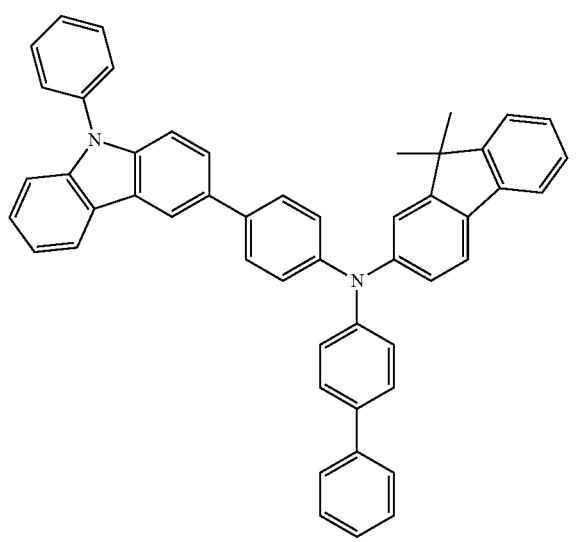

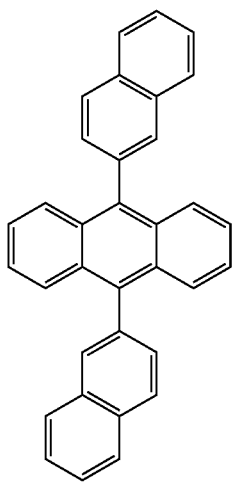

ADN 9,10-di-naphthalene-2-yl-anthracene (ADN) as a blue fluorescent host, and

Compound 8 as a blue fluorescent dopant, were co-deposited at a weight ratio of about 98:2 on the hole transport layer to form an emission layer having a thickness of about 300 Å.

Afterward, Alq$_3$ was vacuum-deposited on the emission layer to form an electron transport layer having a thickness of about 300 Å. Then, LiF, an alkali metal halide, was vacuum-deposited on the electron transport layer to form an electron injection layer having a thickness of about 10 Å. Aluminum (Al) was vacuum-deposited on the electron injection layer to form a cathode having a thickness of about 3000 Å, thereby forming a LiF/Al electrode to complete the manufacture of an organic light-emitting device.

Example 2

Organic light-emitting devices were manufactured in the same (or substantially the same) manner as in Example 1 except that Compound 14 was used instead of Compound 8 to form an emission layer.

Example 3

Organic light-emitting devices were manufactured in the same (or substantially the same) manner as in Example 1 except that Compound 21 was used instead of Compound 8 to form an emission layer.

Example 4

Organic light-emitting devices were manufactured in the same (or substantially the same) manner as in Example 1 except that Compound 31 was used instead of Compound 8 to form an emission layer.

Example 5

Organic light-emitting devices were manufactured in the same (or substantially the same) manner as in Example 1 except that Compound 42 was used instead of Compound 8 to form an emission layer.

Example 6

Organic light-emitting devices were manufactured in the same (or substantially the same) manner as in Example 1 except that Compound 48 was used instead of Compound 8 to form an emission layer.

Example 7

Organic light-emitting devices were manufactured in the same (or substantially the same) manner as in Example 1 except that Compound 55 was used instead of Compound 8 to form an emission layer.

Example 8

Organic light-emitting devices were manufactured in the same (or substantially the same) manner as in Example 1 except that Compound 60 was used instead of Compound 8 to form an emission layer.

Example 9

Organic light-emitting devices were manufactured in the same (or substantially the same) manner as in Example 1 except that Compound 72 was used instead of Compound 8 to form an emission layer.

Comparative Example 1

Organic light-emitting devices were manufactured in the same (or substantially the same) manner as in Example 1 except that N,N,N',N'-tetraphenyl-pyrene-1,6-diamine (TPD) was used as a dopant instead of Compound 8.

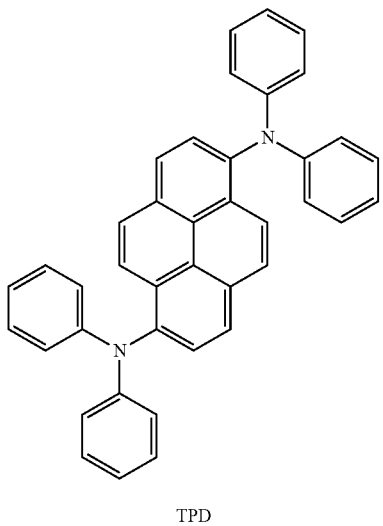

TPD

The characteristics of organic light-emitting devices according to Examples 1 to 9 and Comparative Example 1 are shown in Table 2.

Example 11

An organic light-emitting device was manufactured in the same (or substantially the same) manner as in Example 10 except that Compound 14 was used instead of Compound 8 to form an emission layer.

Example 12

An organic light-emitting device was manufactured in the same (or substantially the same) manner as in Example 10 except that Compound 21 was used instead of Compound 8 to form an emission layer.

Example 13

An organic light-emitting device was manufactured in the same (or substantially the same) manner as in Example 10 except that Compound 31 was used instead of Compound 8 to form an emission layer.

Example 14

An organic light-emitting device was manufactured in the same (or substantially the same) manner as in Example 10 except that Compound 42 was used instead of Compound 8 to form an emission layer.

TABLE 2

| | Dopant | Driving voltage (V) | Current density (mA/cm$^2$) | Luminance (cd/m$^2$) | Efficiency (cd/A) | Emission color | Half-life (hr @100 mA/cm$^2$) |
|---|---|---|---|---|---|---|---|
| Example 1 | Compound 8 | 6.64 | 50 | 3,105 | 6.21 | blue | 333 hr |
| Example 2 | Compound 14 | 6.67 | 50 | 3,185 | 6.37 | blue | 342 hr |
| Example 3 | Compound 21 | 6.70 | 50 | 3,200 | 6.40 | blue | 338 hr |
| Example 4 | Compound 31 | 6.62 | 50 | 3,210 | 6.42 | blue | 347 hr |
| Example 5 | Compound 42 | 6.71 | 50 | 3,230 | 6.46 | blue | 361 hr |
| Example 6 | Compound 48 | 6.72 | 50 | 3,165 | 6.33 | blue | 341 hr |
| Example 7 | Compound 55 | 6.75 | 50 | 3,205 | 6.41 | blue | 376 hr |
| Example 8 | Compound 60 | 6.64 | 50 | 3,325 | 6.65 | blue | 383 hr |
| Example 9 | Compound 72 | 6.58 | 50 | 3,290 | 6.58 | blue | 365 hr |
| Comparative Example 1 | TPD | 6.96 | 50 | 2,730 | 5.46 | blue | 248 hr |

Comparative Example 2

An organic emission layer was manufactured in the same (or substantially the same) manner as in Example 1 except that in forming an emission layer, Compound H9 represented by Formula 4 was used as a host instead of ADN, and TPD was used as a dopant instead of Compound 8.

Example 10

An organic light-emitting device was manufactured in the same (or substantially the same) manner as in Example 1 except that in forming an emission layer, Compound H9 represented by Formula 4 was used as a host instead of ADN.

Example 15

An organic light-emitting device was manufactured in the same (or substantially the same) manner as in Example 10 except that in forming an emission layer, Compound H45 was used as a host instead of Compound H9, and Compound 14 was used as a dopant instead of Compound 8.

Example 16

An organic light-emitting device was manufactured in the same (or substantially the same) manner as in Example 15 except that Compound 21 was used instead of Compound 14 to form an emission layer.

Example 17

An organic light-emitting device was manufactured in the same (or substantially the same) manner as in Example 15 except that Compound 31 was used instead of Compound 14 to form an emission layer.

Example 18

An organic light-emitting device was manufactured in the same (or substantially the same) manner as in Example 15 except that Compound 42 was used instead of Compound 14 to form an emission layer.

Example 19

An organic light-emitting device was manufactured in the same (or substantially the same) manner as in Example 15 except that Compound 48 was used instead of Compound 14 to form an emission layer.

Example 20

An organic light-emitting device was manufactured in the same (or substantially the same) manner as in Example 15 except that Compound 55 was used instead of Compound 14 to form an emission layer.

Example 21

An organic light-emitting device was manufactured in the same (or substantially the same) manner as in Example 15 except that Compound 60 was used instead of Compound 14 to form an emission layer.

Example 22

An organic light-emitting device was manufactured in the same manner as in Example 10 except that in forming an emission layer, Compound H60 was used as a host instead of Compound H9, and Compound 14 was used as a dopant instead of Compound 8.

Example 23

An organic light-emitting device was manufactured in the same (or substantially the same) manner as in Example 22 except that Compound 21 was used instead of Compound 14 to form an emission layer.

Example 24

An organic light-emitting device was manufactured in the same (or substantially the same) manner as in Example 22 except that Compound 42 was used instead of Compound 14 to form an emission layer.

Example 25

An organic light-emitting device was manufactured in the same (or substantially the same) manner as in Example 22 except that Compound 55 was used instead of Compound 14 to form an emission layer.

Example 26

An organic light-emitting device was manufactured in the same (or substantially the same) manner as in Example 22 except that Compound 60 was used instead of Compound 14 to form an emission layer.

Example 27

An organic light-emitting device was manufactured in the same (or substantially the same) manner as in Example 22 except that Compound 72 was used instead of Compound 14 to form an emission layer.

The characteristics of organic light-emitting devices according to Examples 10 to 27 and Comparative Examples 1 and 2 are shown in Table 3.

TABLE 3

| | Host | Dopant | Driving voltage (V) | Current density (mA/cm$^2$) | Luminance (cd/m$^2$) | Efficiency (cd/A) | Emission color | half-life (hr @100 mA/cm$^2$) |
|---|---|---|---|---|---|---|---|---|
| Example 10 | Compound H9 | Compound 8 | 6.54 | 50 | 3,275 | 6.55 | blue | 442 hr |
| Example 11 | Compound H9 | Compound 14 | 6.55 | 50 | 3,330 | 6.66 | blue | 456 hr |
| Example 12 | Compound H9 | Compound 21 | 6.61 | 50 | 3,370 | 6.74 | blue | 437 hr |
| Example 13 | Compound H9 | Compound 31 | 6.58 | 50 | 3,365 | 6.73 | blue | 479 hr |
| Example 14 | Compound H9 | Compound 42 | 6.57 | 50 | 3,375 | 6.75 | blue | 481 hr |
| Example 15 | Compound H45 | Compound 14 | 6.52 | 50 | 3,345 | 6.69 | blue | 467 hr |
| Example 16 | Compound H45 | Compound 21 | 6.58 | 50 | 3,365 | 6.73 | blue | 471 hr |
| Example 17 | Compound H45 | Compound 31 | 6.53 | 50 | 3,425 | 6.85 | blue | 478 hr |
| Example 18 | Compound H45 | Compound 42 | 6.54 | 50 | 3,475 | 6.95 | blue | 492 hr |
| Example 19 | Compound H45 | Compound 48 | 6.52 | 50 | 3,420 | 6.84 | blue | 468 hr |
| Example 20 | Compound H45 | Compound 55 | 6.53 | 50 | 3,505 | 7.01 | blue | 495 hr |
| Example 21 | Compound | Compound | 6.48 | 50 | 3,575 | 7.15 | blue | 490 hr |

TABLE 3-continued

| | Host | Dopant | Driving voltage (V) | Current density (mA/cm$^2$) | Luminance (cd/m$^2$) | Efficiency (cd/A) | Emission color | half-life (hr @100 mA/cm$^2$) |
|---|---|---|---|---|---|---|---|---|
| Example 22 | Compound H60 | H45 Compound 14 | 6.53 | 50 | 3,325 | 6.65 | blue | 420 hr |
| Example 23 | Compound H60 | Compound 21 | 6.53 | 50 | 3,380 | 6.76 | blue | 399 hr |
| Example 24 | Compound H60 | Compound 42 | 6.54 | 50 | 3,430 | 6.86 | blue | 437 hr |
| Example 25 | Compound H60 | Compound 55 | 6.53 | 50 | 3,460 | 6.92 | blue | 445 hr |
| Example 26 | Compound H60 | Compound 60 | 6.48 | 50 | 3,510 | 7.02 | blue | 457 hr |
| Example 27 | Compound H60 | Compound 72 | 6.43 | 50 | 3,490 | 6.98 | blue | 453 hr |
| Comparative Example 1 | ADN | TPD | 6.96 | 50 | 2,730 | 5.46 | blue | 248 hr |
| Comparative Example 2 | H9 | TPD | 6.73 | 50 | 2,835 | 5.67 | blue | 384 hr |

When a compound represented by Formula 1 according to embodiments of the present invention was used as a dopant in a blue emission layer, efficiency and lifespan of an organic light-emitting device may improve compared to those of an organic light-emitting device using a related compound as a blue dopant. In addition, when a compound represented by Formula 4 according to embodiments of the present invention is also used at the same time as a host in the emission layer, this effect may be further increased.

As described above, according to one or more embodiments of the present invention, the compound represented by Formula 1 has excellent stability and is suitable as an electron transporting material. An organic light-emitting device using the compound of Formula 1 may have high efficiency, low voltage, high luminance, and long lifespan.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the drawing, it will be understood by those of ordinary skill in the art that various changes in form and details may be made therein without departing from the spirit and scope as defined by the following claims and equivalents thereof.

What is claimed is:

1. A compound represented by Formula 1:

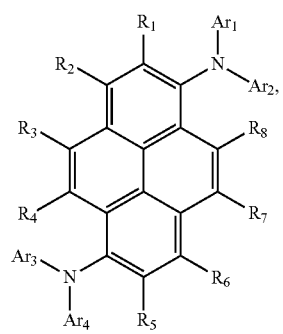

Formula 1 wherein in Formula 1,
R$_1$ to R$_8$ and Ar$_1$ to Ar$_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_2$-C$_{10}$ heterocycloalkyl group, a substituted or unsubstituted C$_3$-C$_{10}$ cycloalkenyl group, a substituted or unsubstituted C$_2$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), and —B(Q$_6$)(Q$_7$);

and at least one selected from Ar$_1$ to Ar$_4$ is represented by Formula 1-a:

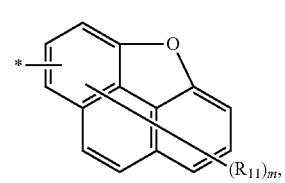

Formula 1-a wherein in Formula 1-a,
R$_{11}$ is as defined in connection with R$_1$ to R$_8$;
m is an integer selected from 1 to 7;
* indicates a binding site; and
wherein in Formulae 1 and 1-a, at least one of the substituents of the substituted C$_1$-C$_{60}$ alkyl group, substituted C$_2$-C$_{60}$ alkenyl group, substituted C$_2$-C$_{60}$ alkynyl group, substituted C$_1$-C$_{60}$ alkoxy group, substituted C$_3$-C$_{10}$ cycloalkyl group, substituted C$_2$-C$_{10}$ heterocycloalkyl group, substituted C$_3$-C$_{10}$ cycloalkenyl group, substituted C$_2$-C$_{10}$ heterocycloalkenyl group, substituted C$_6$-C$_{60}$ aryl group, substituted C$_6$-C$_{60}$ aryloxy group, substituted C$_6$-C$_{60}$ arylthio group, substituted C$_1$-C$_{60}$ heteroaryl group, substituted monovalent non-aromatic condensed polycyclic group, and substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The compound of claim 1, wherein
$Ar_1$ to $Ar_4$ in Formula 1 that are not represented by Formula 1-a are each independently selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

3. The compound of claim 1, wherein
in Formula 1, $R_1$ to $R_8$ are each independently selected from a hydrogen, a deuterium, a substituted or unsubstituted $C_1$-$C_{60}$ alkyl group, a substituted or unsubstituted $C_6$-$C_{60}$ aryl group, and —Si($Q_3$)($Q_4$)($Q_5$).

4. The compound of claim 1, wherein
$Ar_1$ to $Ar_4$ in Formula 1 that are not represented by Formula 1-a are each independently a compound represented by any one of Formulae 2a to 2d:

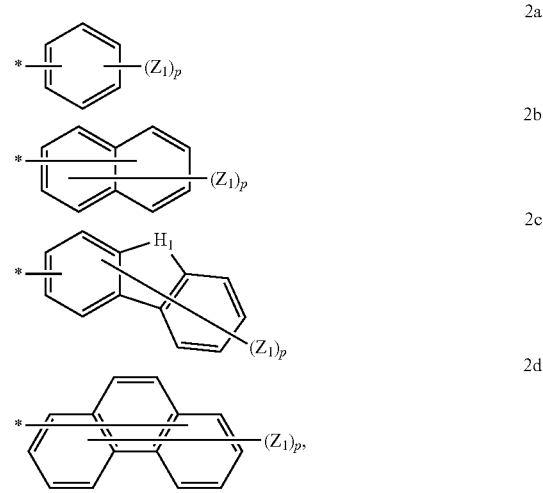

wherein in Formulae 2a to 2d, $Z_1$ is selected from a hydrogen atom, a deuterium, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ condensed polycyclic group, a halogen group, a cyano group, a nitro group, a hydroxyl group, and a carboxyl group;

$H_1$ is selected from —O—, —S—, and —C$R_{51}R_{52}$—;
p is an integer selected from 1 to 9;
$R_{51}$ and $R_{52}$ are as defined in connection with $R_1$ to $R_8$; and
* indicates a binding site.

5. The compound of claim 1, wherein
in Formula 1, $R_2$ and $R_6$ are each independently selected from a hydrogen, a deuterium, a $C_1$-$C_{20}$ alkyl group, a $C_6$-$C_{20}$ aryl group, and —Si($Q_{41}$)($Q_{42}$)($Q_{43}$):
wherein $Q_{41}$ to $Q_{43}$ are each independently selected from a $C_1$-$C_{60}$ alkyl group and a $C_6$-$C_{60}$ aryl group.

6. The compound of claim 1, wherein
in Formula 1, $R_1$, $R_3$ to $R_5$, $R_7$, and $R_8$ are each independently selected from a hydrogen and a deuterium.

7. The compound of claim 1, wherein
in Formula 1-a, $R_{11}$ is selected from a hydrogen and a deuterium.

8. The compound of claim 1, wherein
the compound represented by Formula 1 is represented by any one of Formulae 2 and 3:

Formula 2
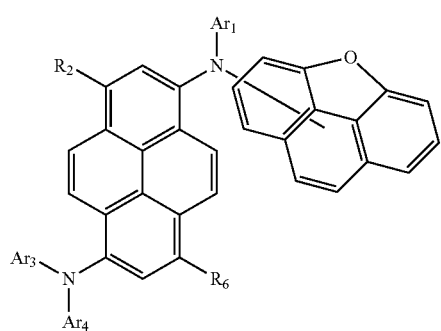
Formula 3
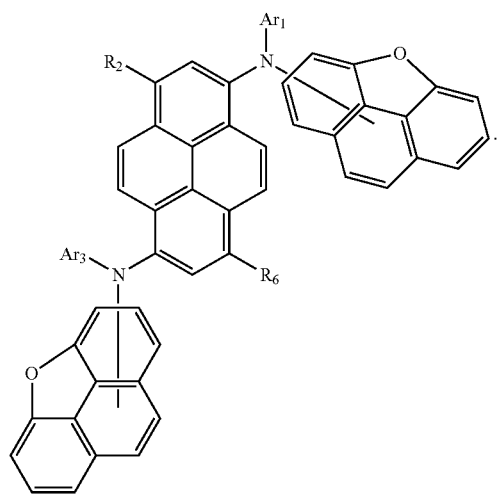
9. The compound of claim 1, wherein
the compound of Formula 1 is selected from compounds 1 through 72:
1
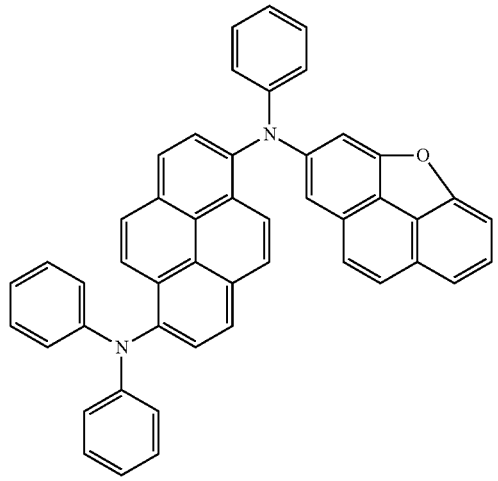
2
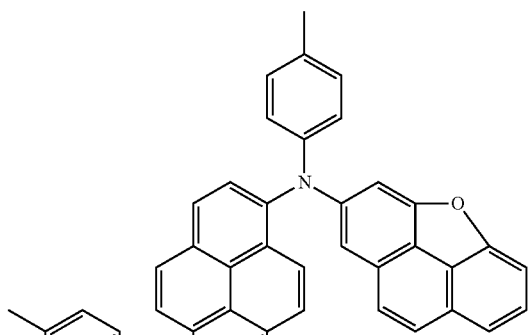
3
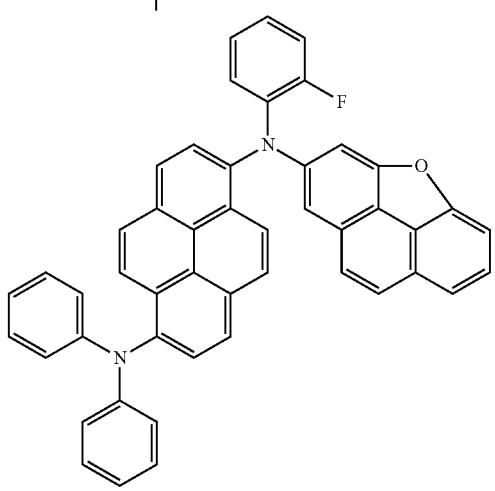
4
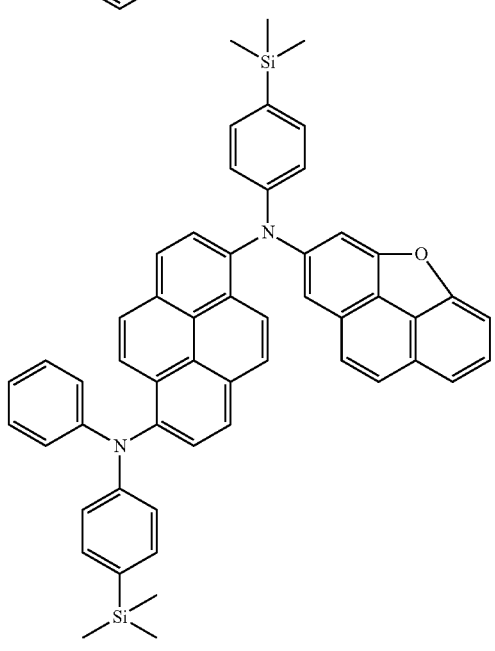

133
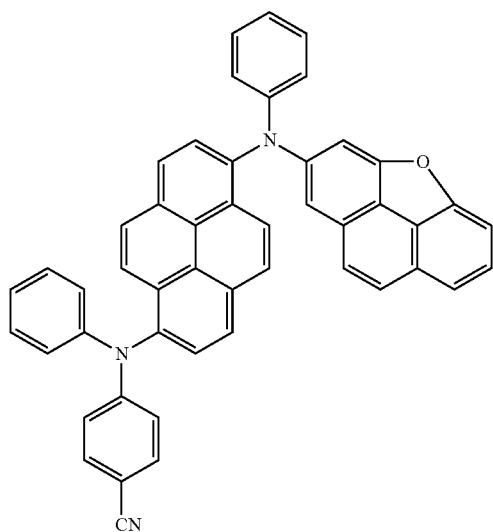
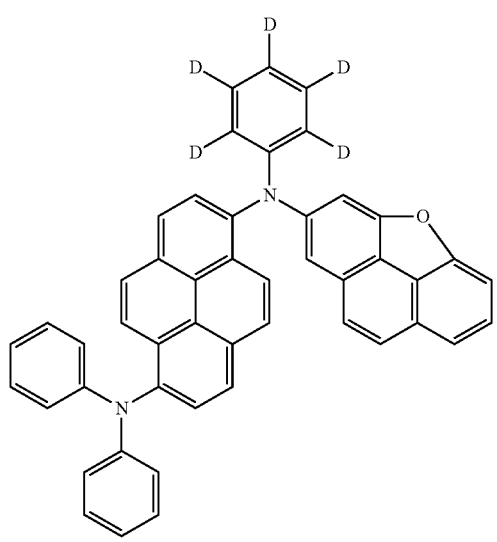
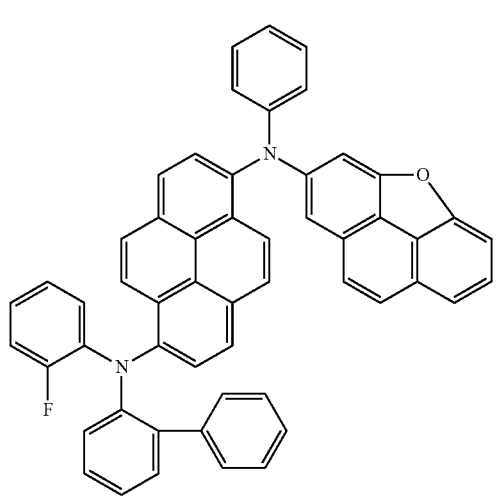
134
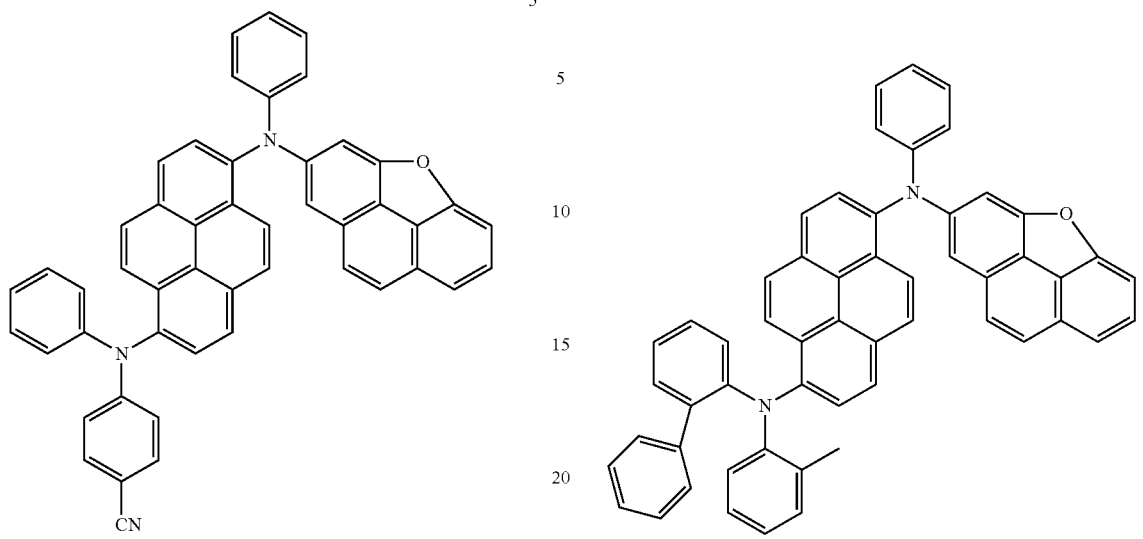
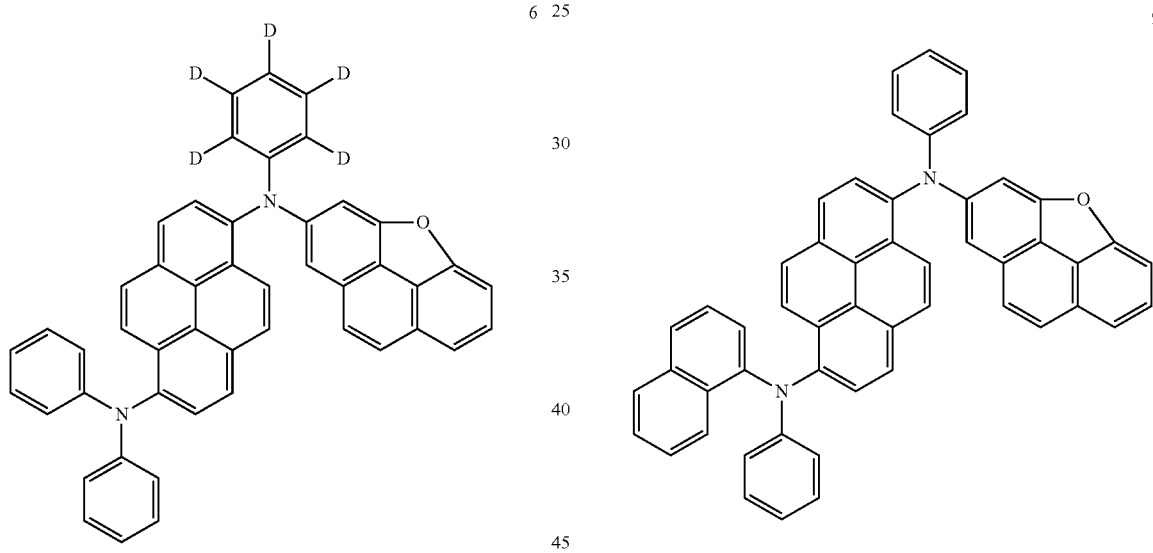
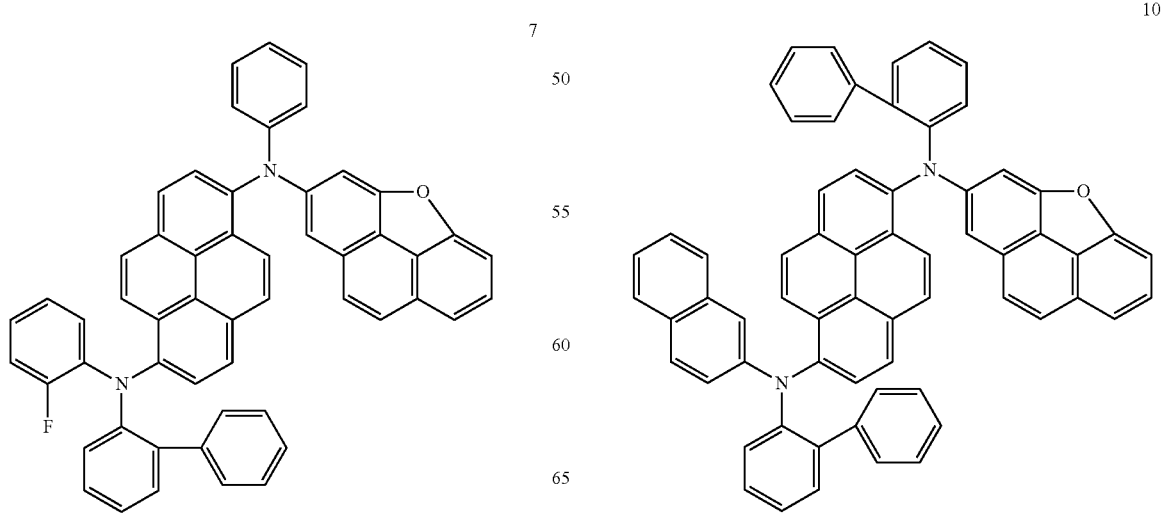

135
-continued
11
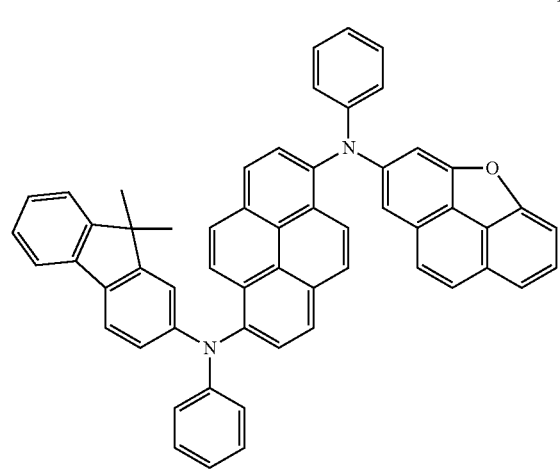
12
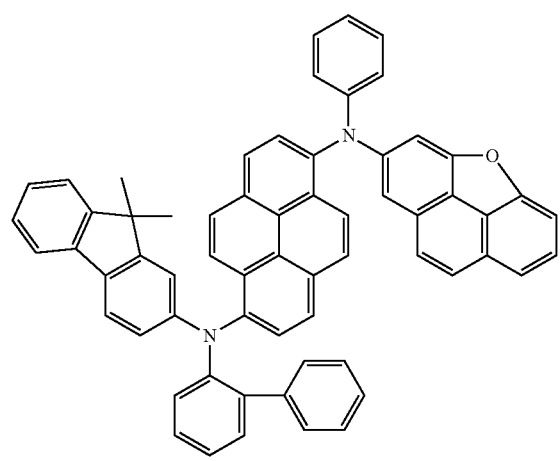
13
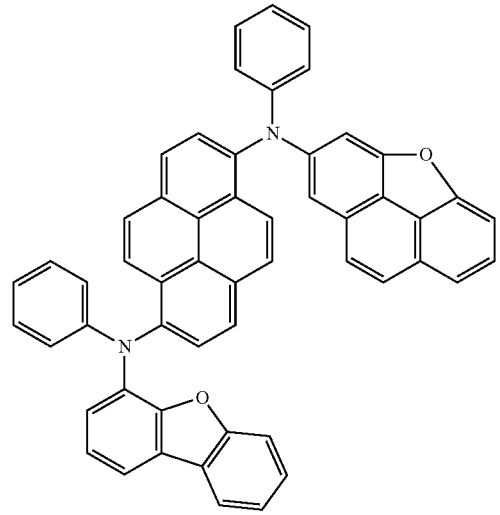
136
-continued
14
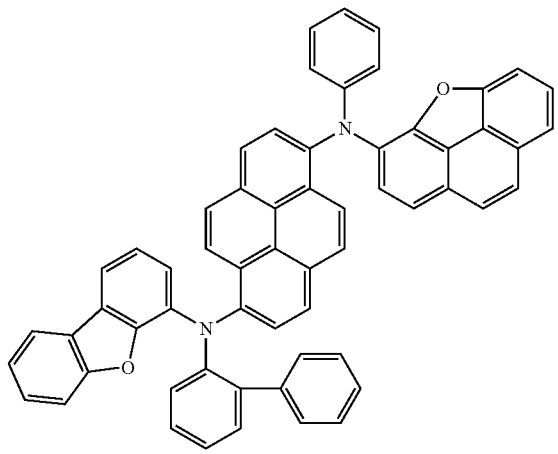
15
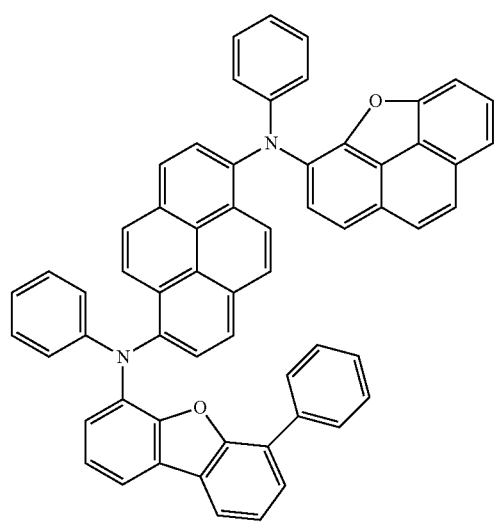
16
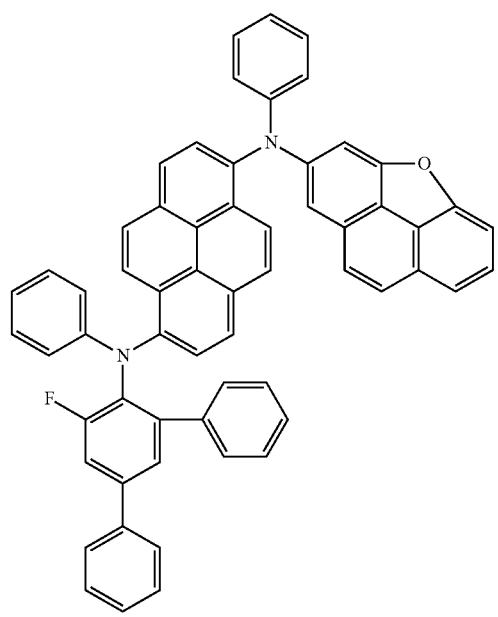

137
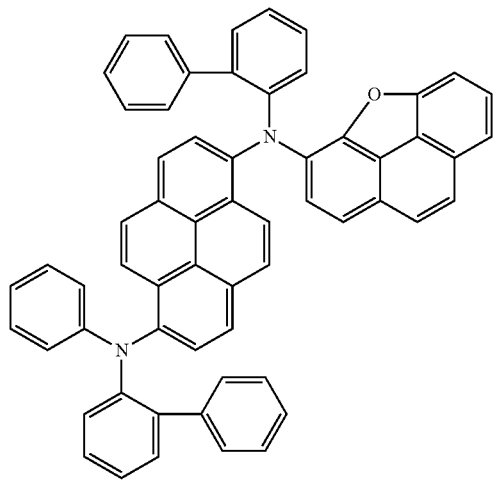
17
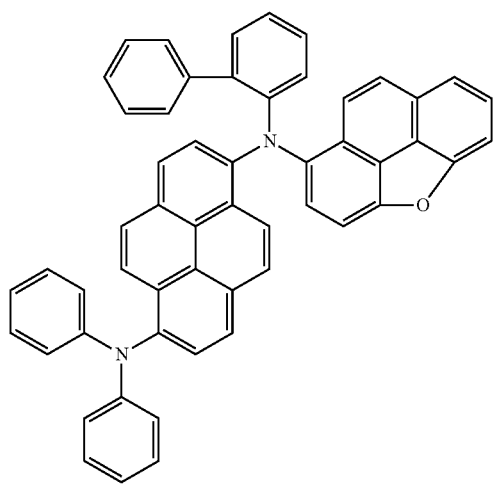
18
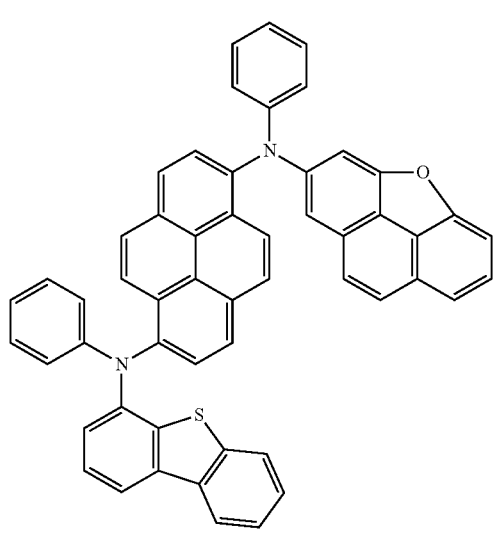
19
138
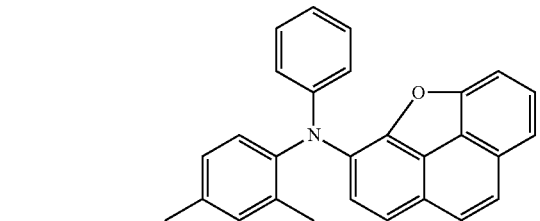
20
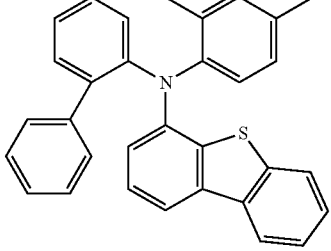
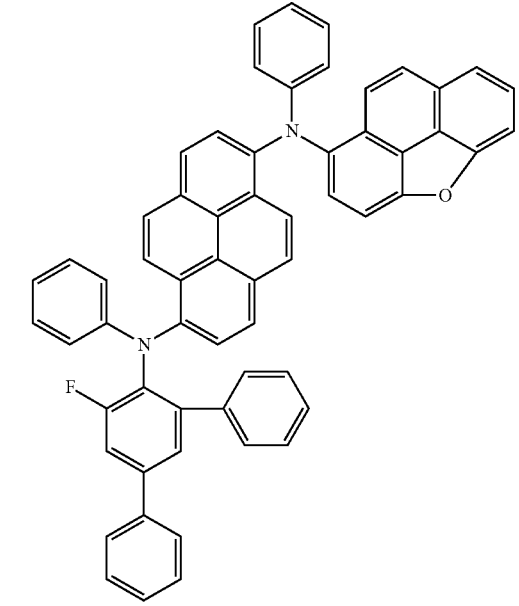
21
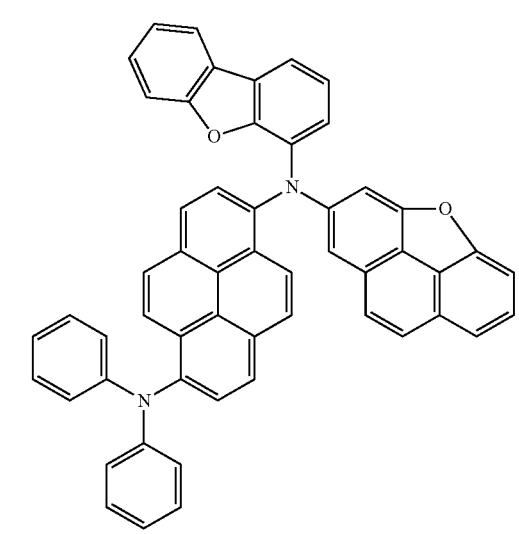
22

23
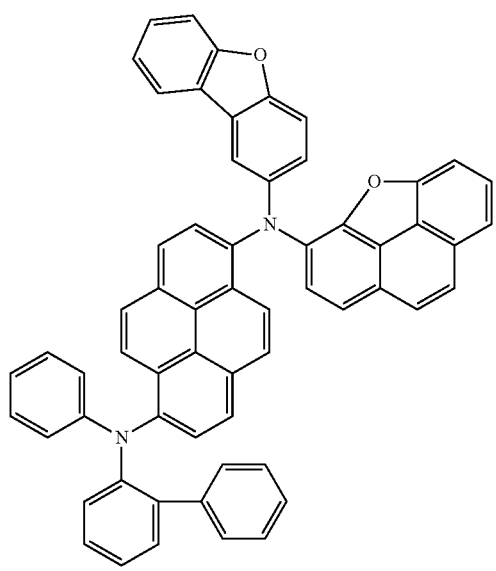
24
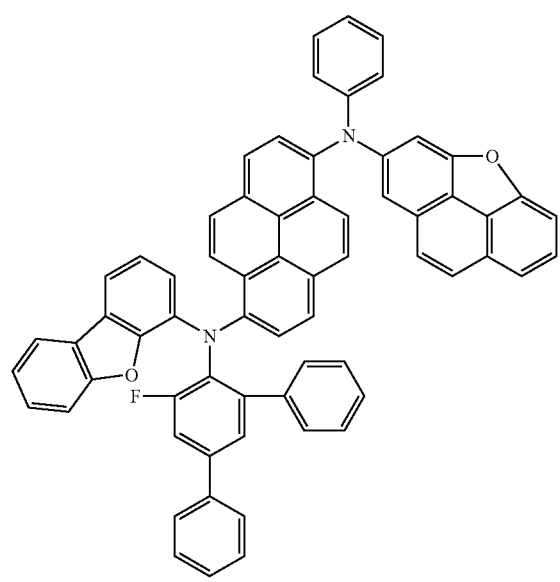
25
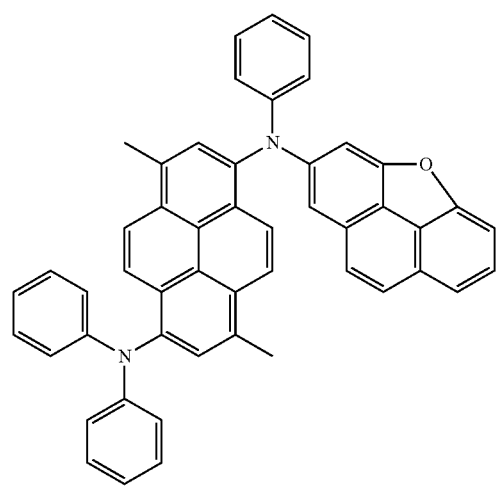
26
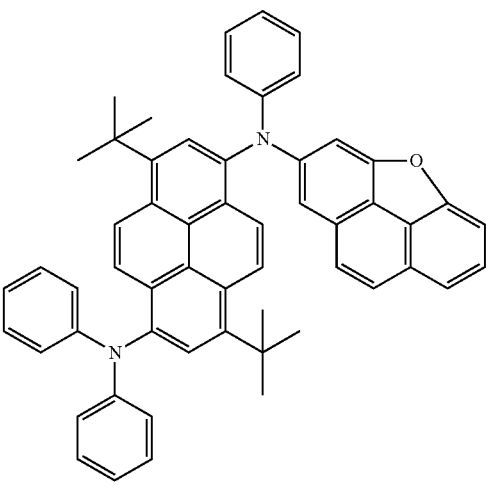
27
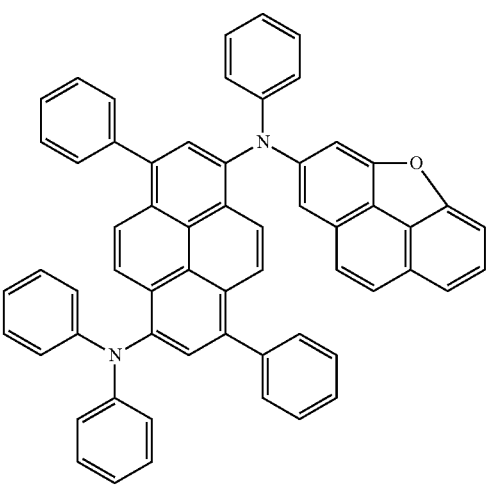
28
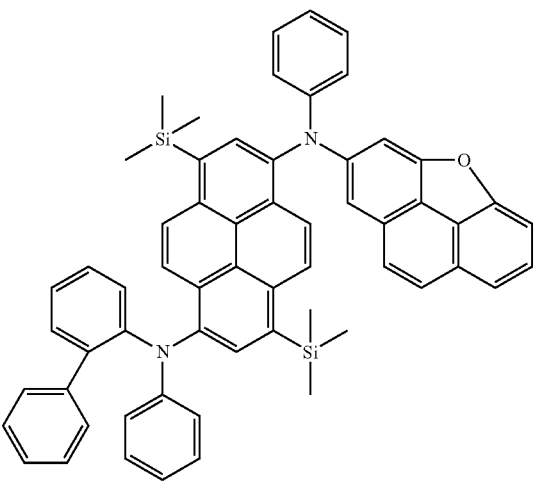

141
-continued
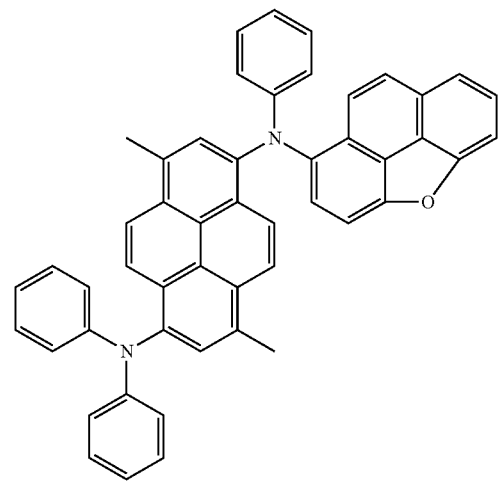
29
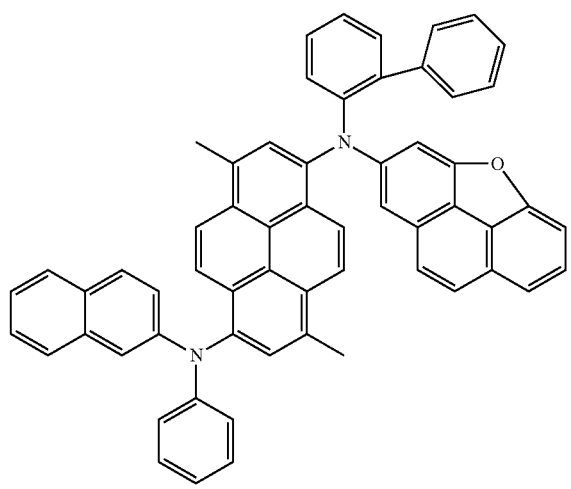
30
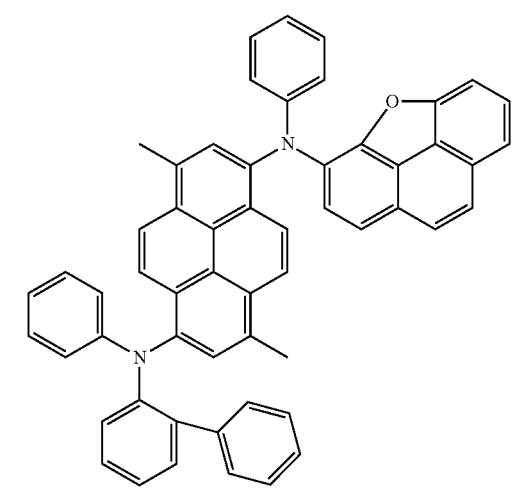
31
142
-continued
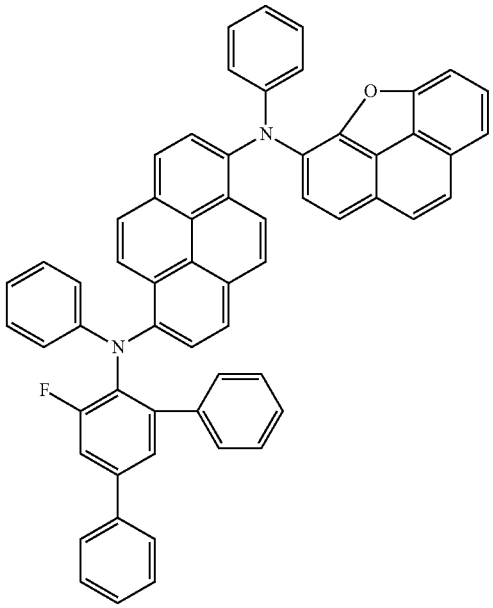
32
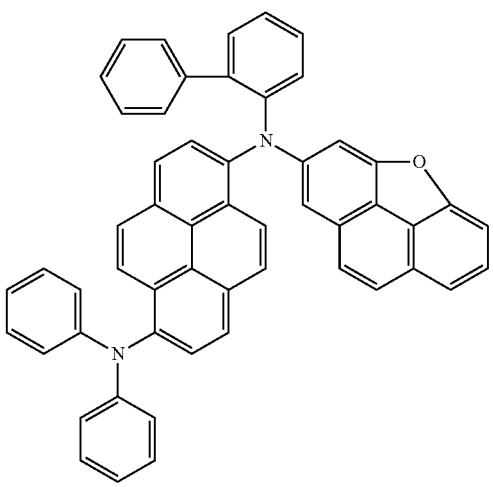
33
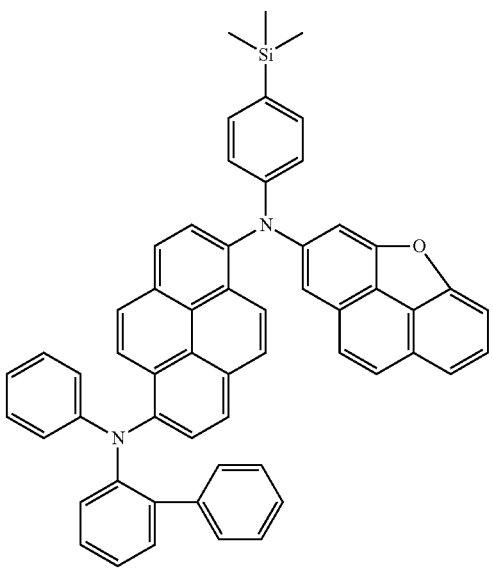
34

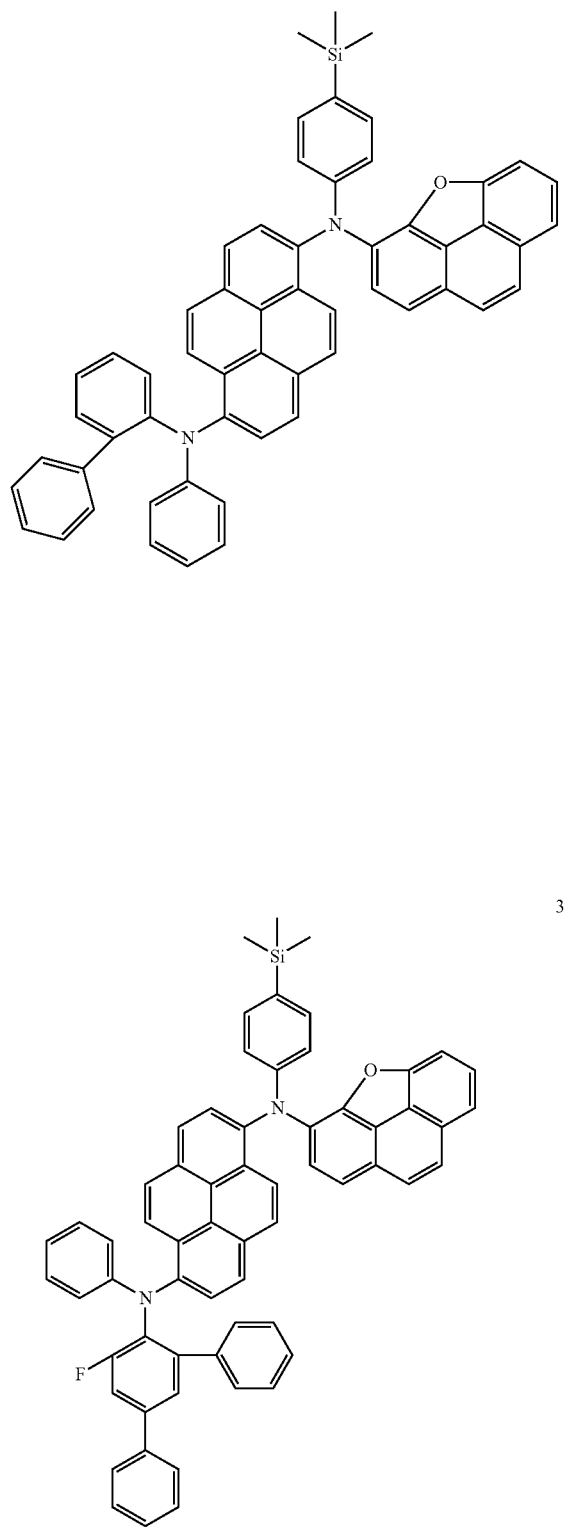
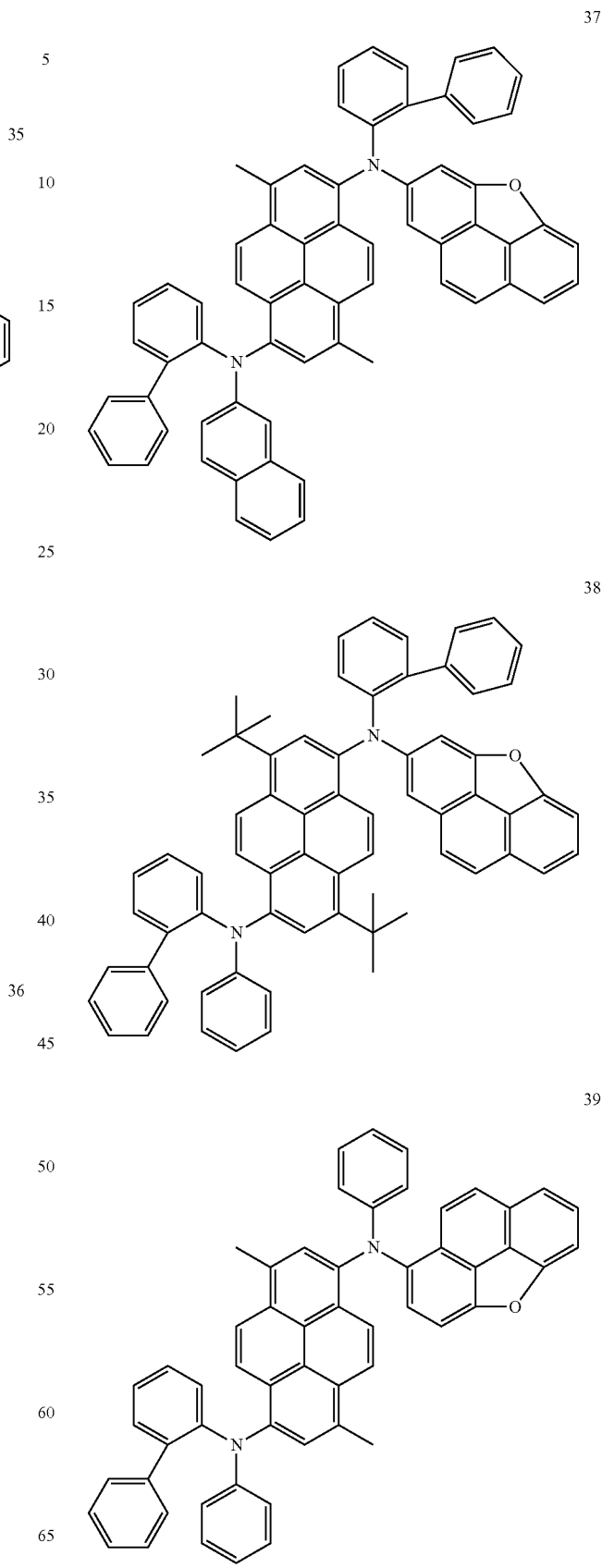

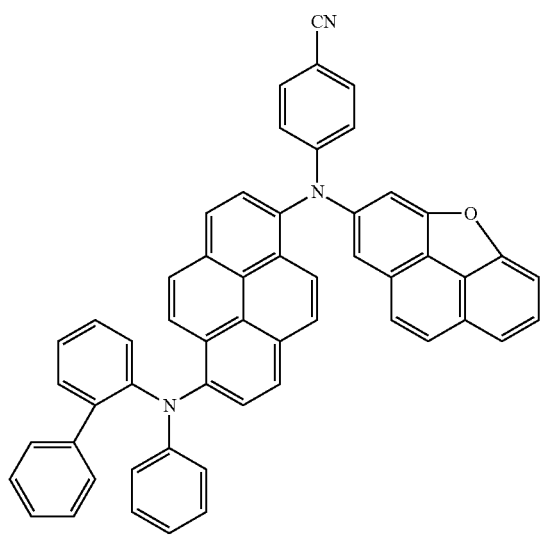
40
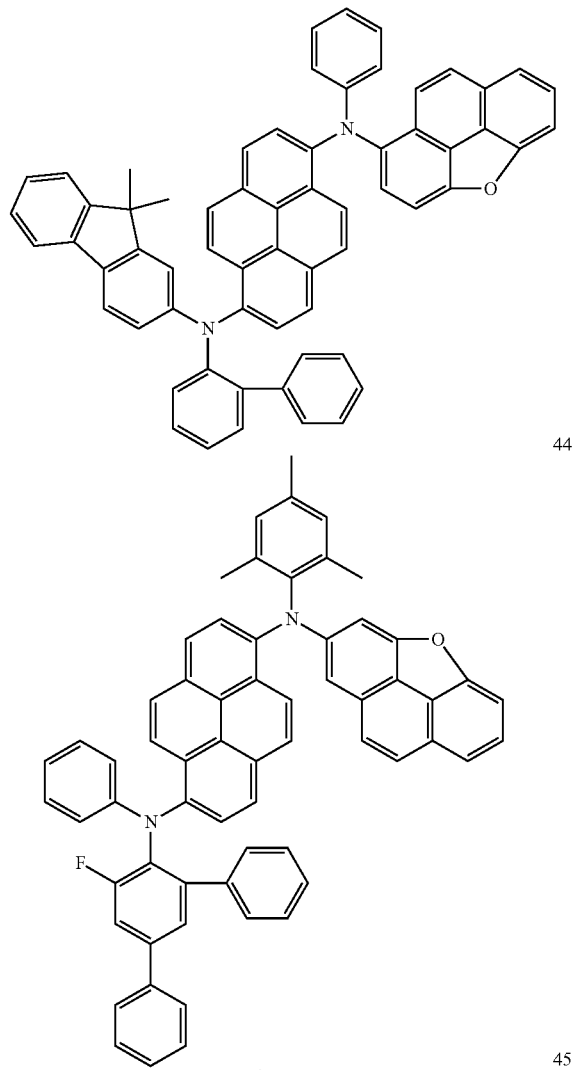
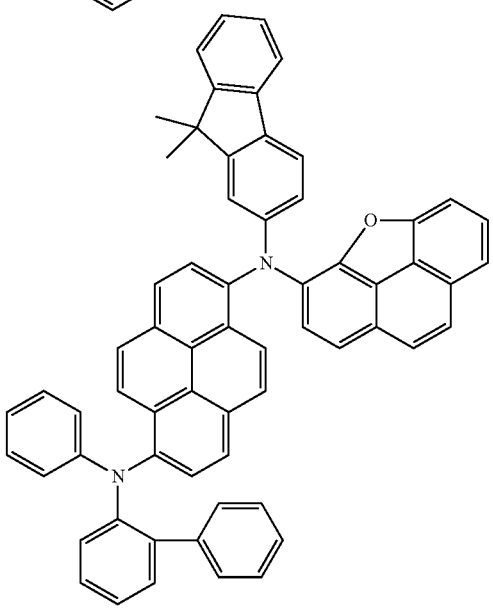

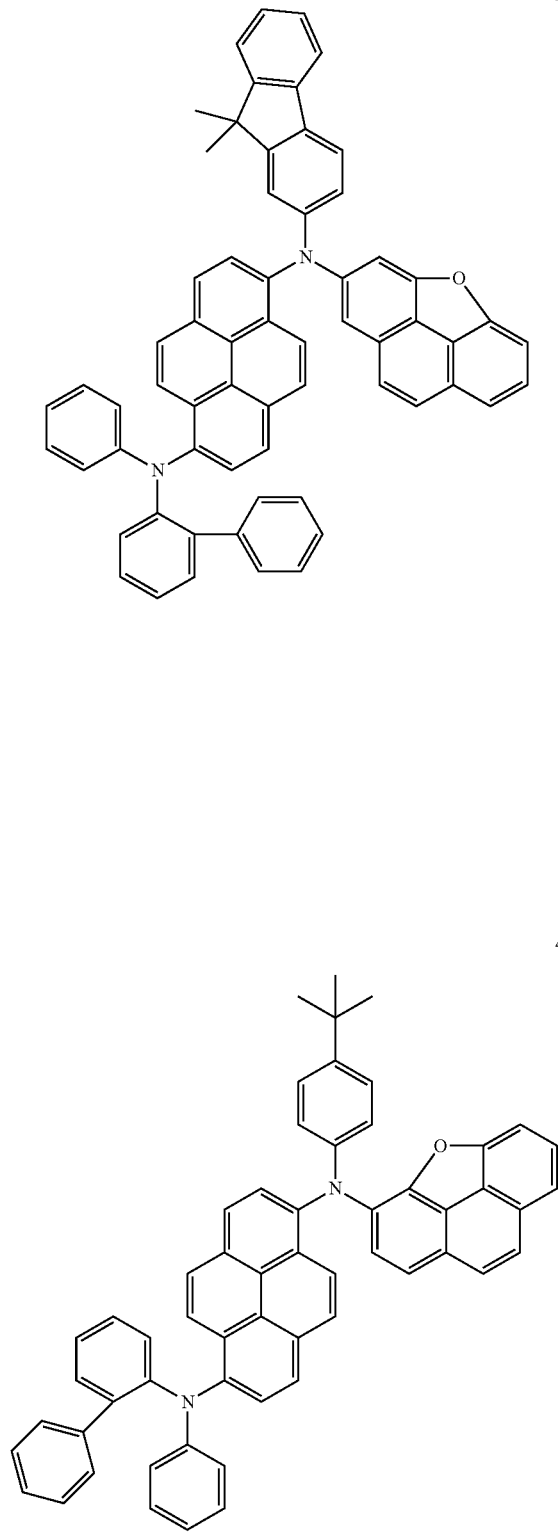
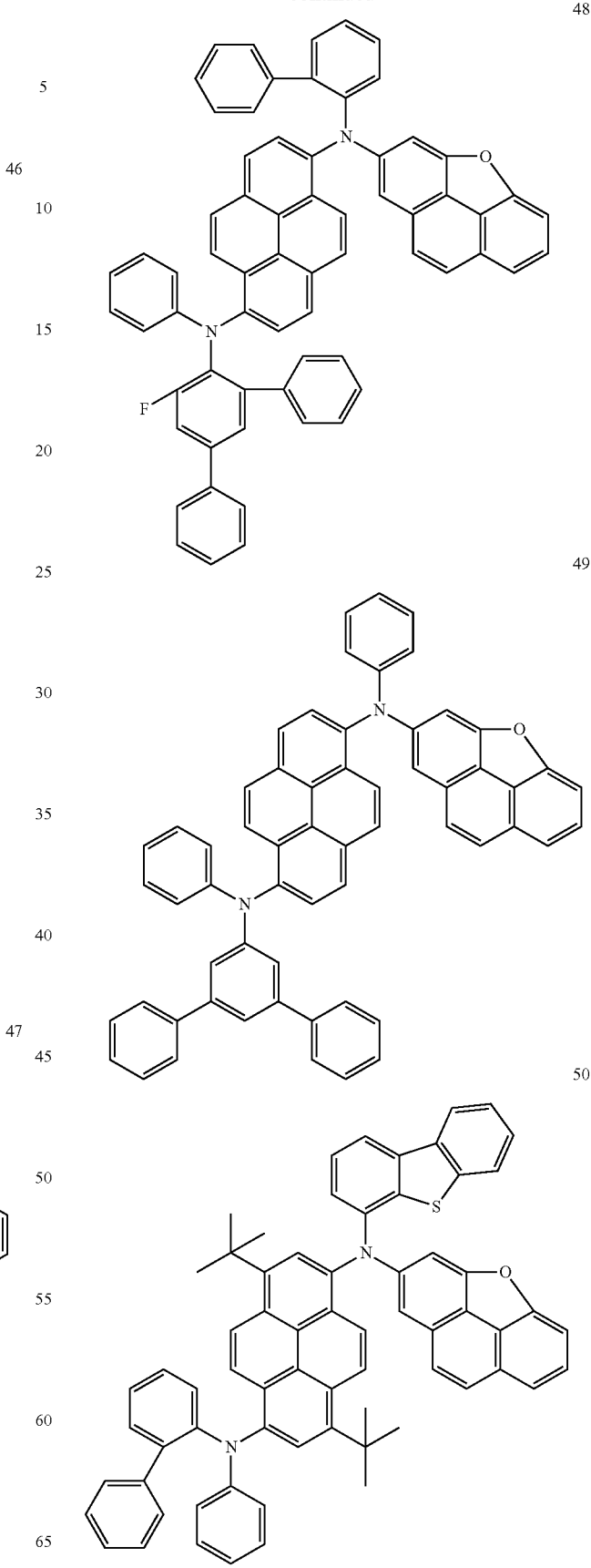

-continued
51
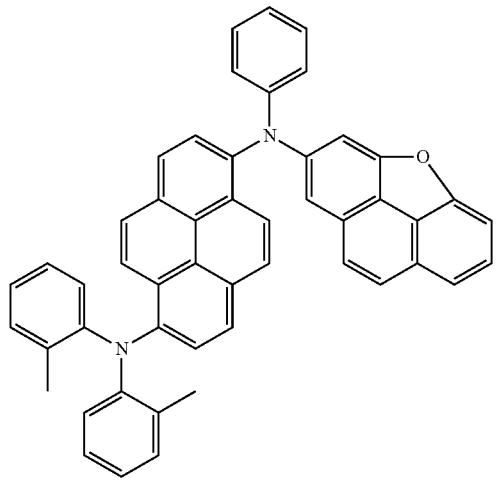
52
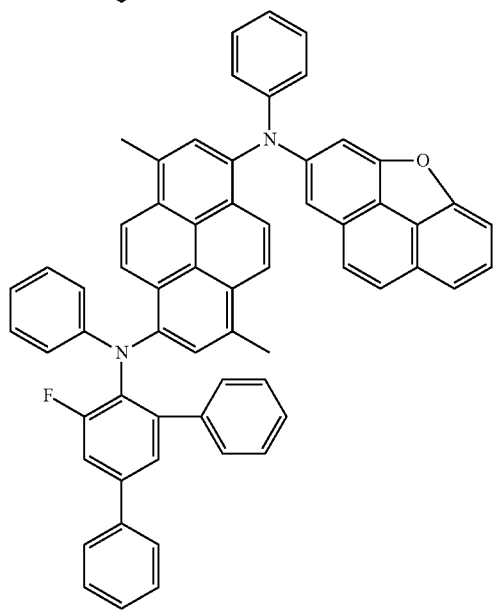
53
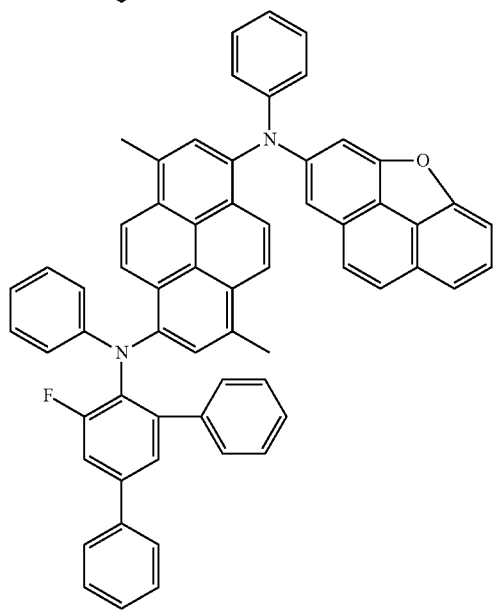
-continued
54
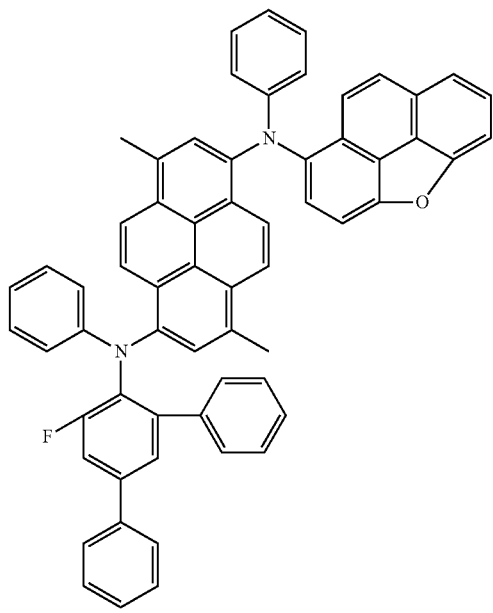
55
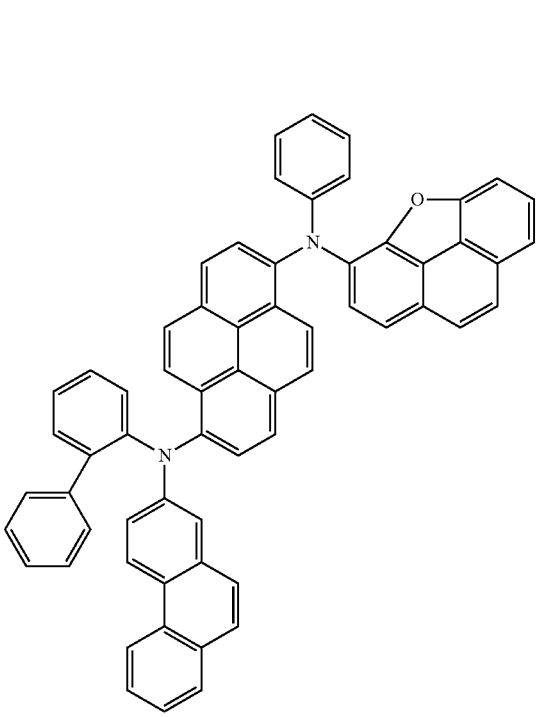

151
56
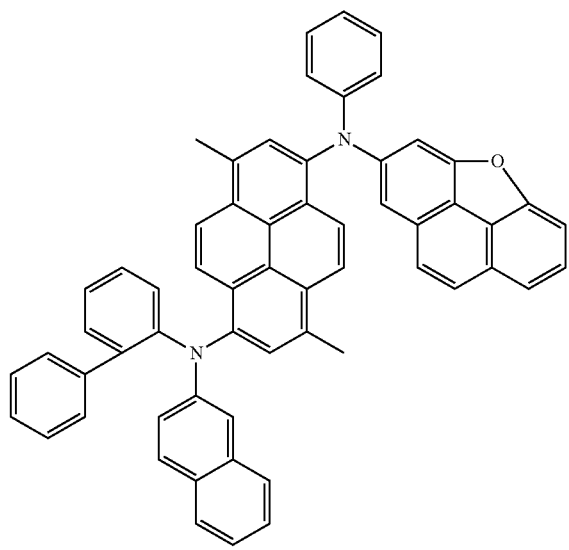
57
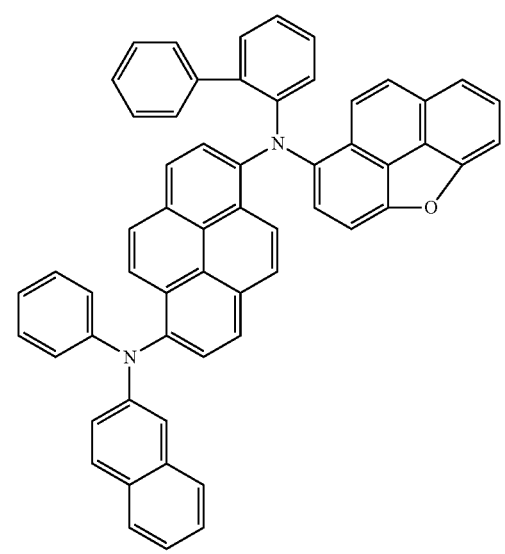
58
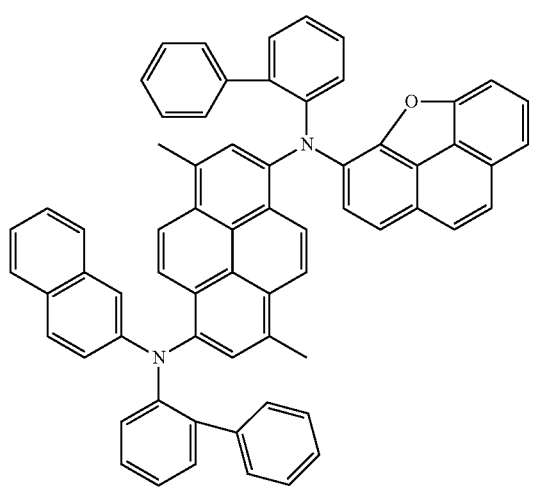
152
59
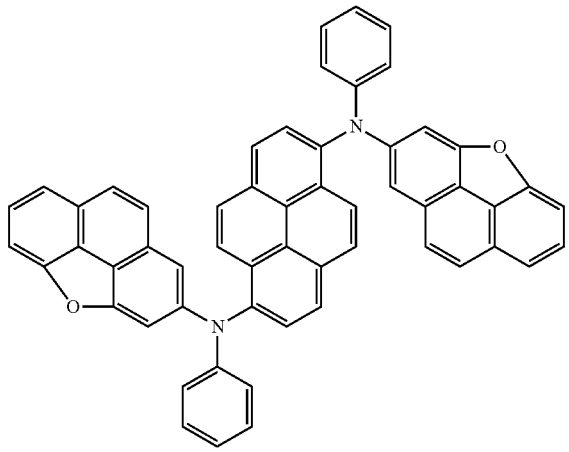
60
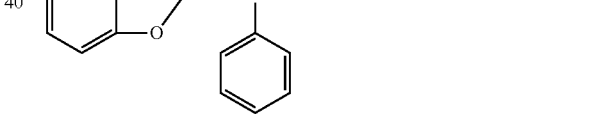
61
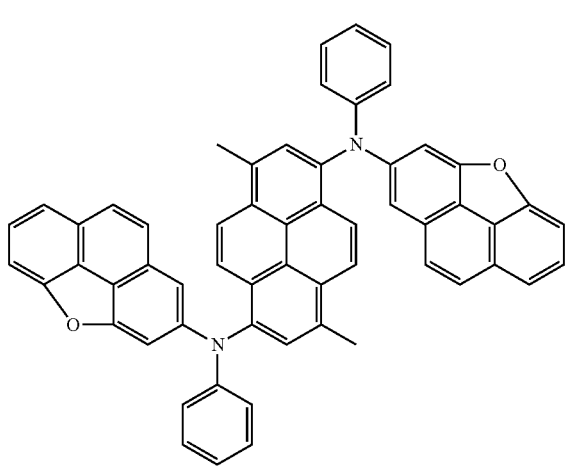

153
-continued
62
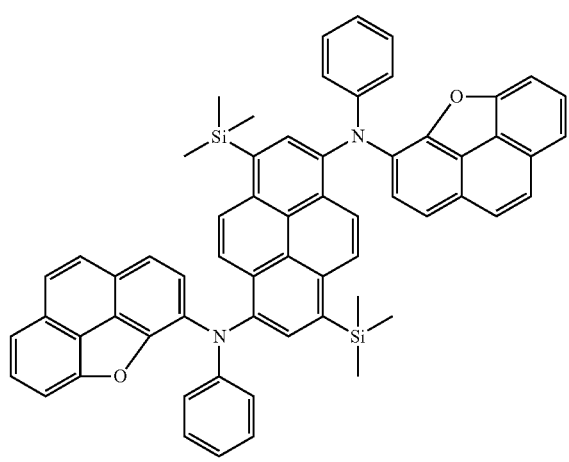
63
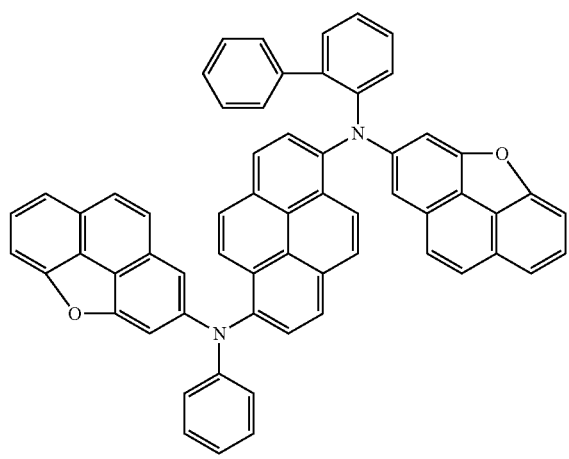
64
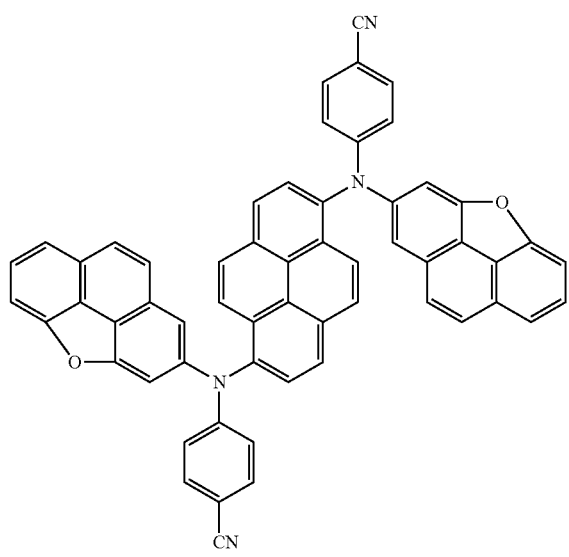
154
-continued
65
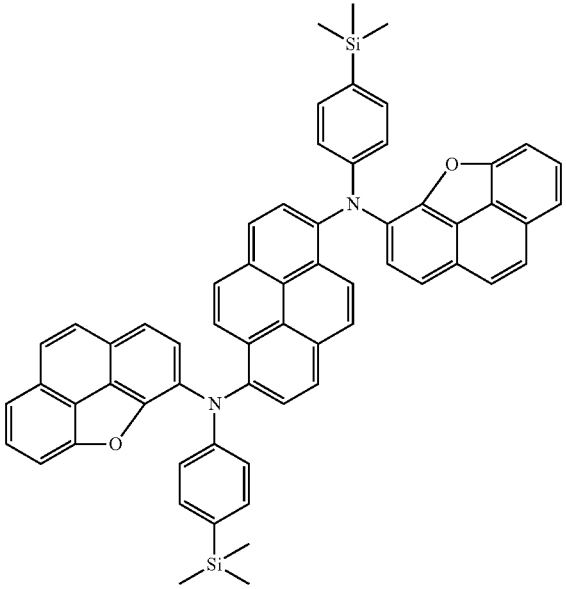
66
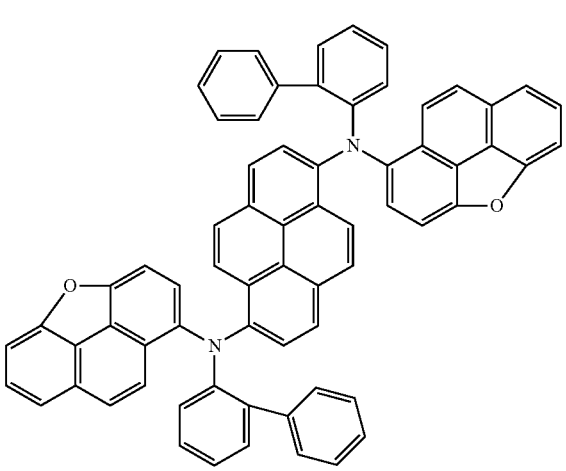
67

68

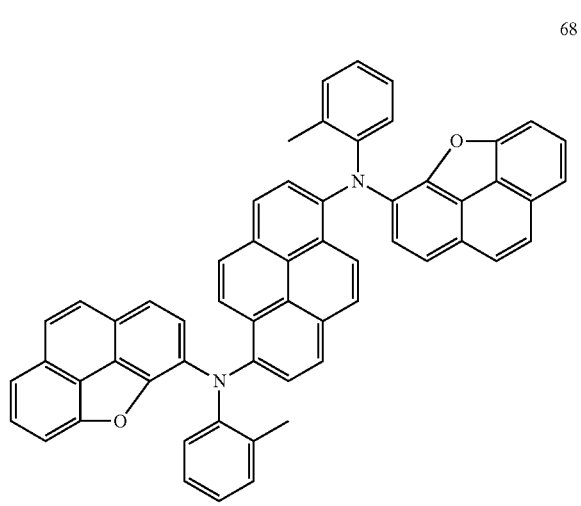

69

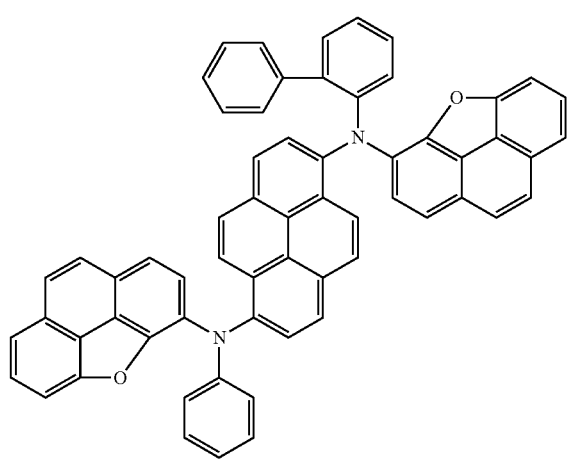

70

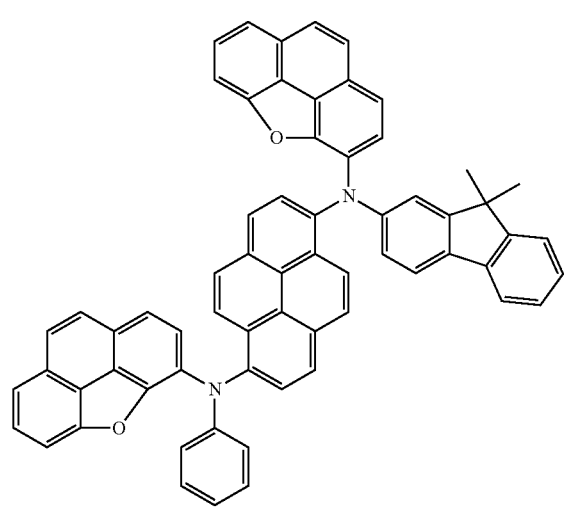

71

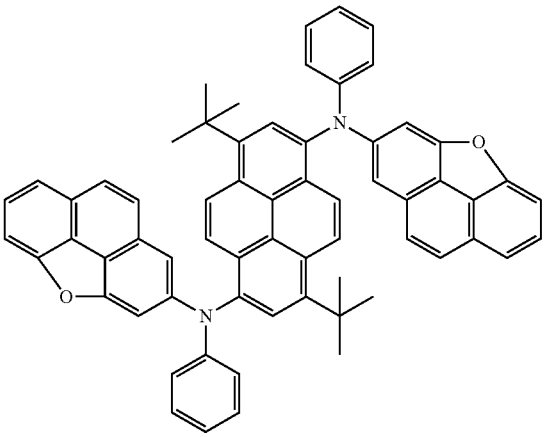

72

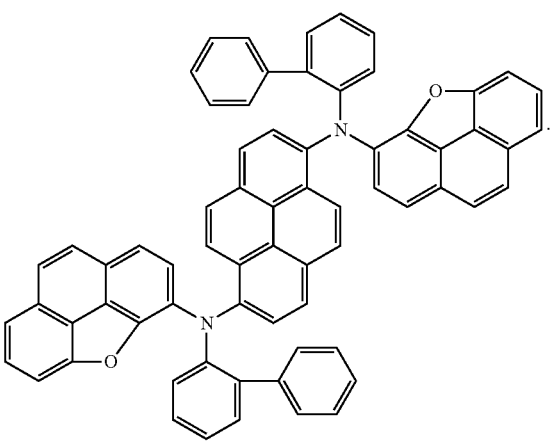

10. An organic light-emitting device comprising:
a first electrode;
a second electrode facing the first electrode; and
an organic layer between the first electrode and the second electrode and comprising an emission layer,
wherein the organic layer comprises the compound represented by Formula 1 of claim 1.

11. The organic light-emitting device of claim 10, wherein the first electrode is an anode,
the second electrode is a cathode,
and the organic layer comprises
a hole transport region between the first electrode and the emission layer, the hole transport region comprising at least one selected from a hole injection layer, a hole transport layer, and an electron blocking layer, and an electron transport region between the emission layer and the second electrode, the electron transport region comprising at least one selected from a hole blocking layer, an electron transport layer, and an electron injection layer.

12. The organic light-emitting device of claim 10, wherein the emission layer comprises the compound represented by Formula 1.

13. The organic light-emitting device of claim 10, wherein the emission layer comprises the compound represented by Formula 1 as a dopant.

14. The organic light-emitting device of claim 10, wherein the emission layer further comprises a compound represented by Formula 4:

Formula 4

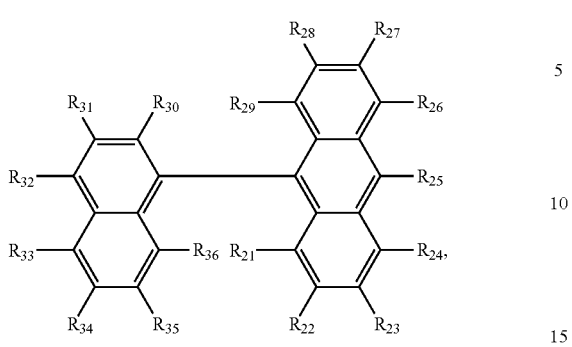

wherein in Formula 4, $R_{21}$ to $R_{36}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

wherein at least one of the substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), and wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

15. The organic light-emitting device of claim 14, wherein the organic light-emitting device comprises the compound represented by Formula 4 as a host.

16. The organic light-emitting device of claim 14, wherein in Formula 4, $R_{25}$, $R_{27}$, $R_{31}$, $R_{32}$, and $R_{33}$ are each independently selected from a hydrogen, a deuterium, a cyano group, a substituted or unsubstituted $C_1$-$C_{60}$ alkyl group, —Si($Q_3$)($Q_4$)($Q_5$), and Formulae 3a to 3c:

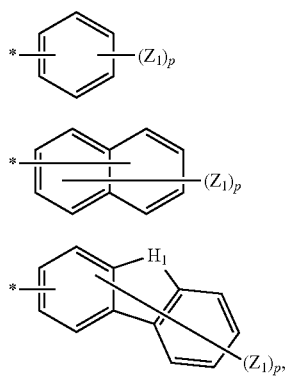

wherein in Formulae 3a to 3c, $Z_1$ is selected from a hydrogen atom, a deuterium, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ condensed polycyclic group, a halogen group, a cyano group, a nitro group, a hydroxyl group, and a carboxyl group;

$H_1$ is selected from —O—, —S—, —$CR_{51}R_{52}$—, and —$NR_{53}$—;

p is an integer selected from 1 to 7;

$R_{51}$ and $R_{53}$ are defined the same as $R_{21}$ to $R_{36}$, wherein, optionally, $R_{51}$ and $R_{52}$ are linked to each other to form a ring; and

* indicates a binding site.

17. The organic light-emitting device of claim 14, wherein in Formula 4, $R_{21}$ to $R_{24}$, $R_{26}$, $R_{28}$ to $R_{30}$, $R_{34}$ to $R_{36}$ are each independently selected from a hydrogen and a deuterium.

18. The organic light-emitting device of claim 14, wherein the emission layer comprises the compound represented by Formula 1 as a fluorescent or phosphorescent dopant and the compound represented by Formula 4 as a fluorescent or phosphorescent host.

19. The organic light-emitting device of claim 14, wherein the compound represented by Formula 4 is represented by one of Compounds H1 to H78:

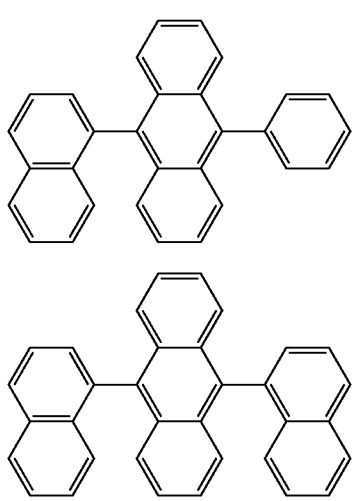

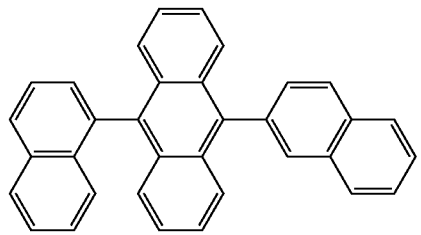

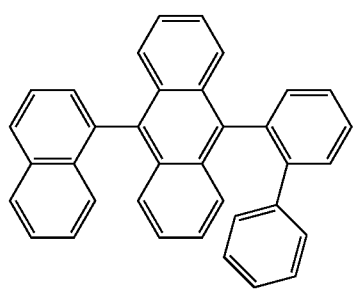

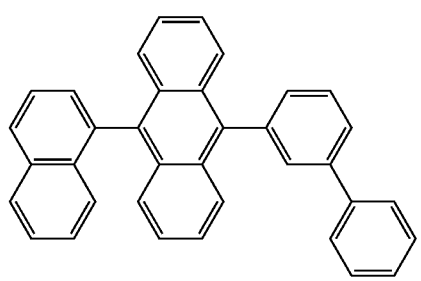

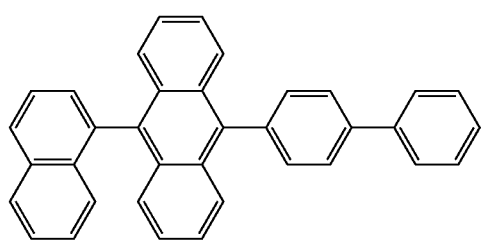

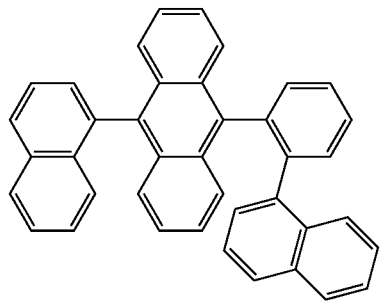

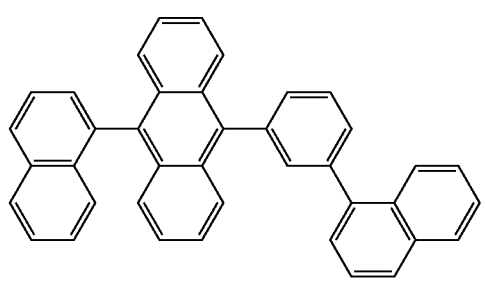

H9
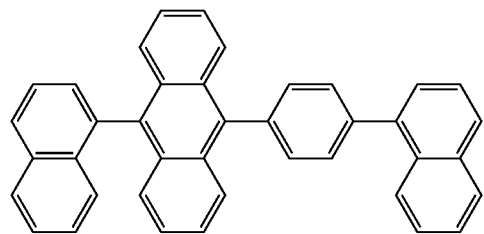
H10
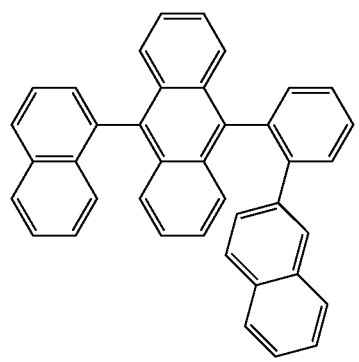
H11
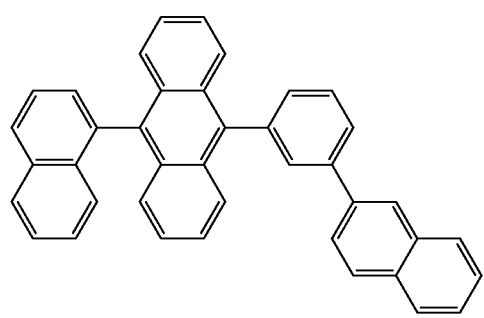
H12
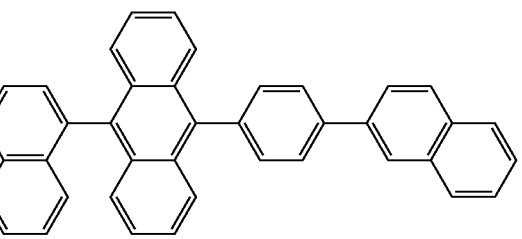
H13
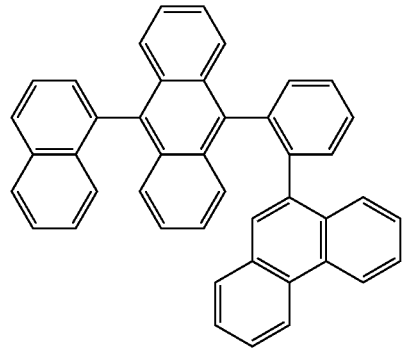
H14
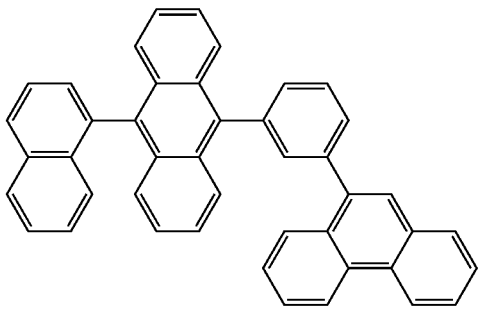
H15
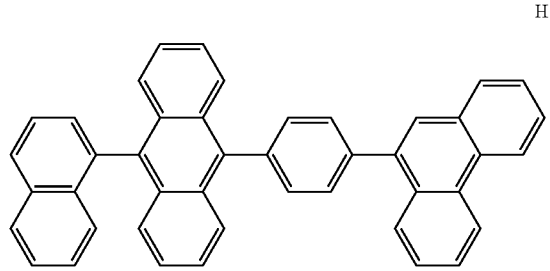
H16
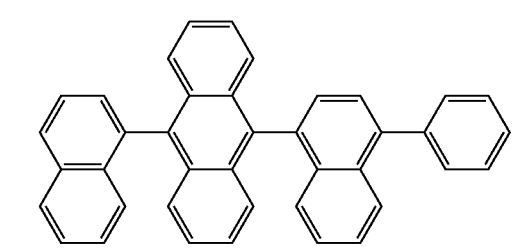
H17
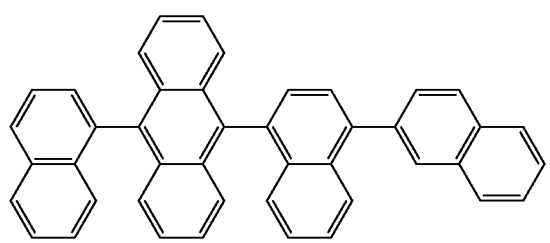
H18
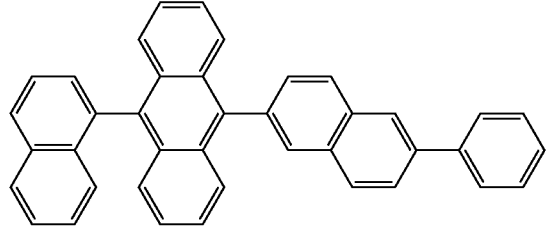
H19
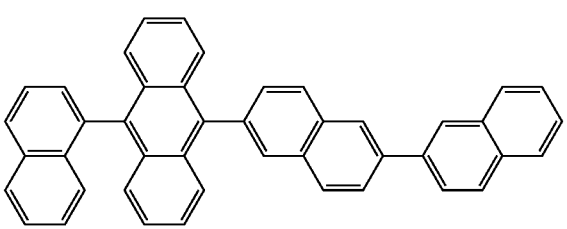

-continued
H20
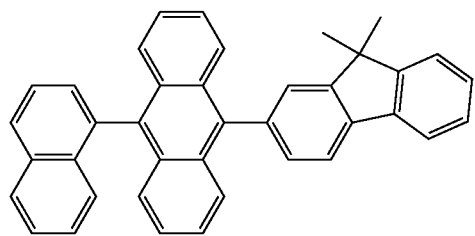
H21
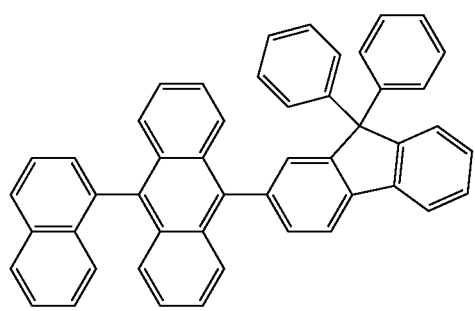
H22
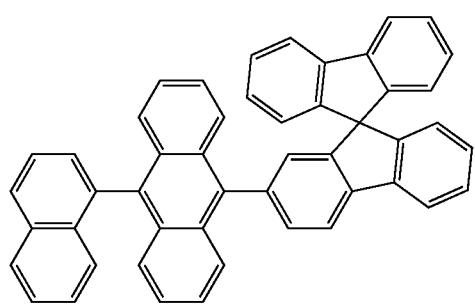
H23
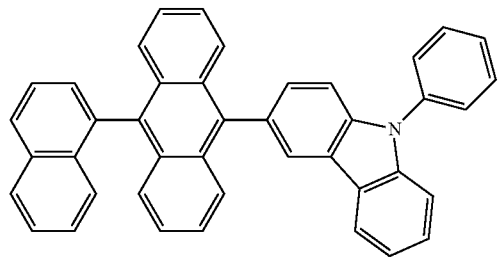
H24
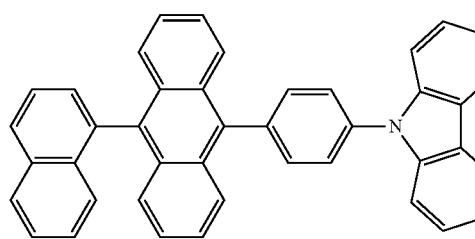
-continued
H25
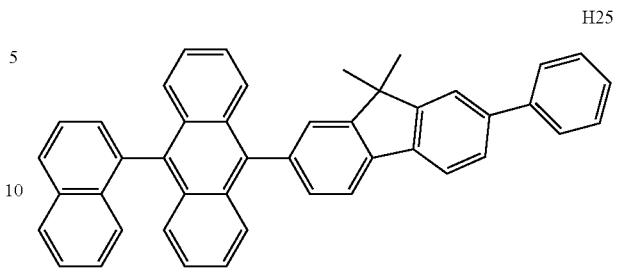
H26
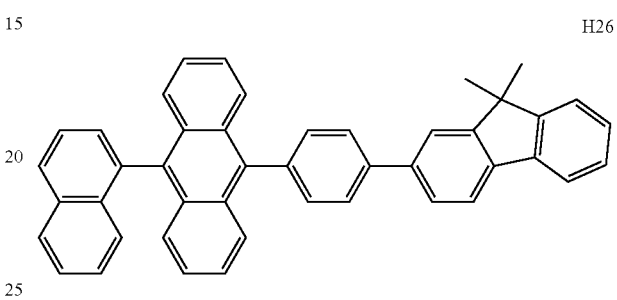
H27
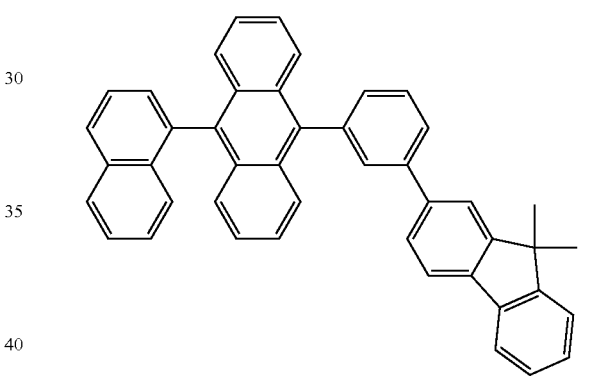
H28
H29
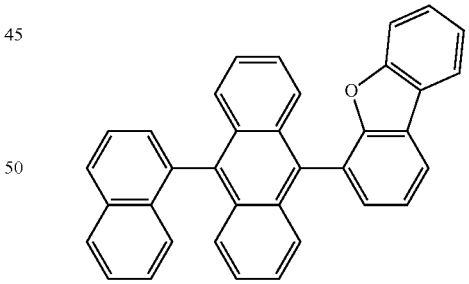

H30
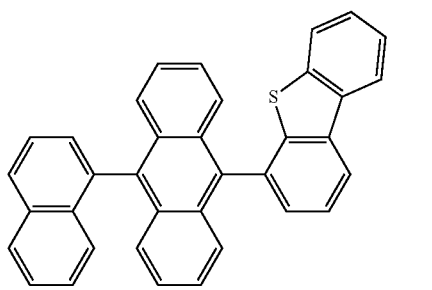
H31
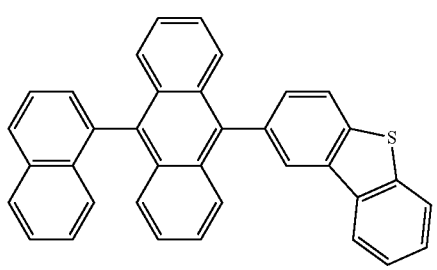
H32
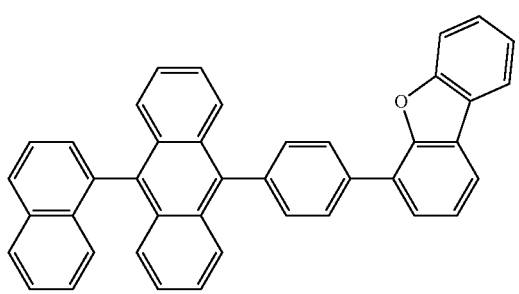
H33
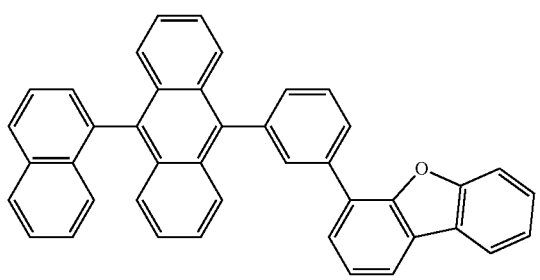
H34
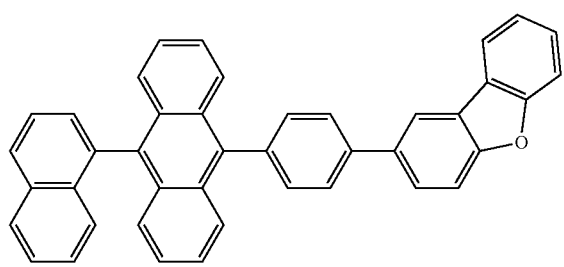
H35
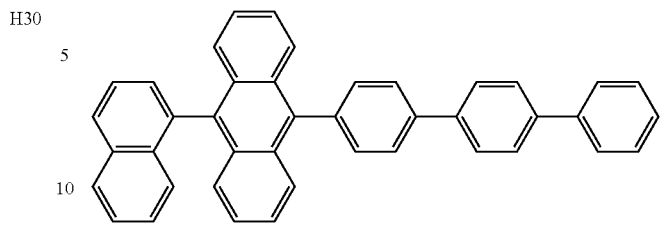
H36
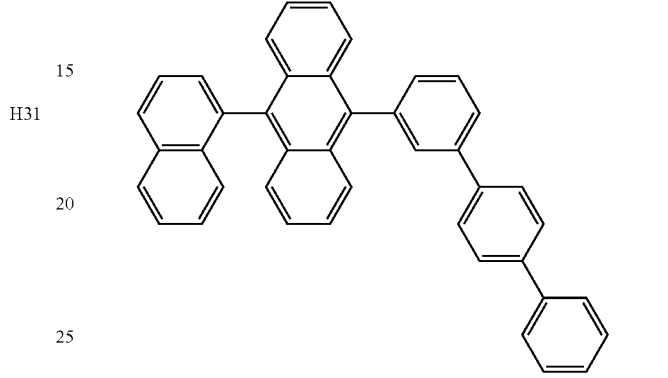
H37
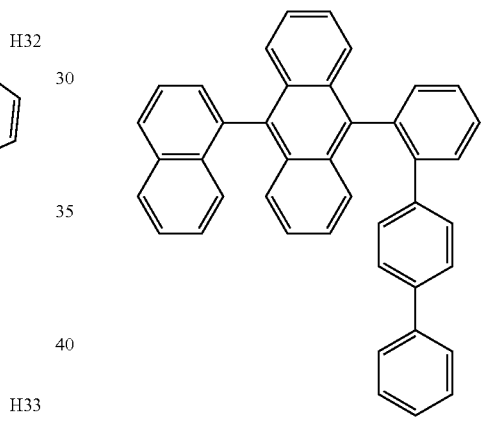
H38
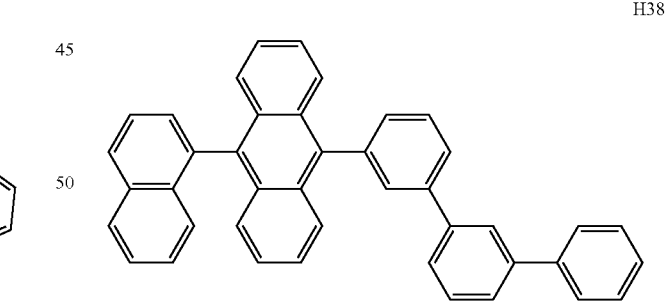
H39
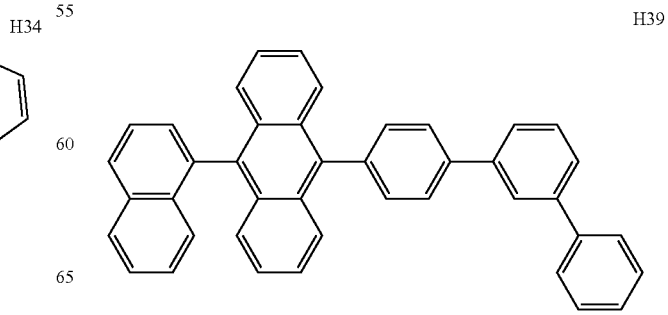

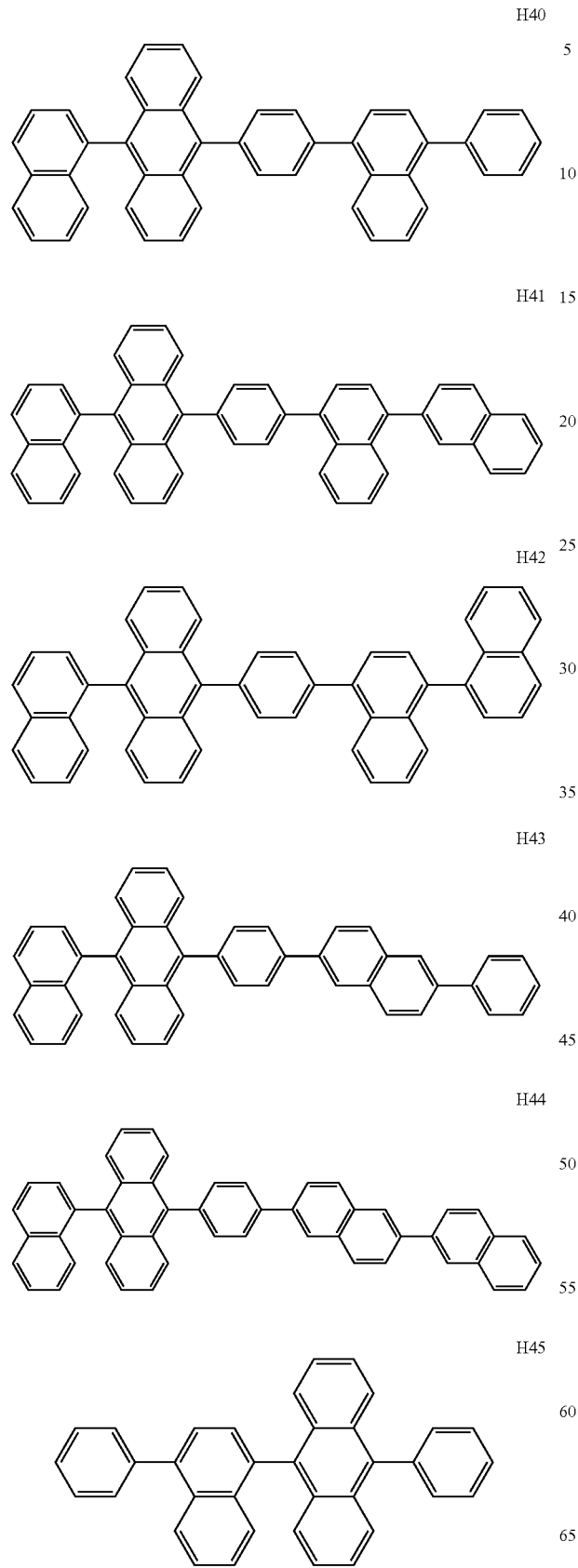
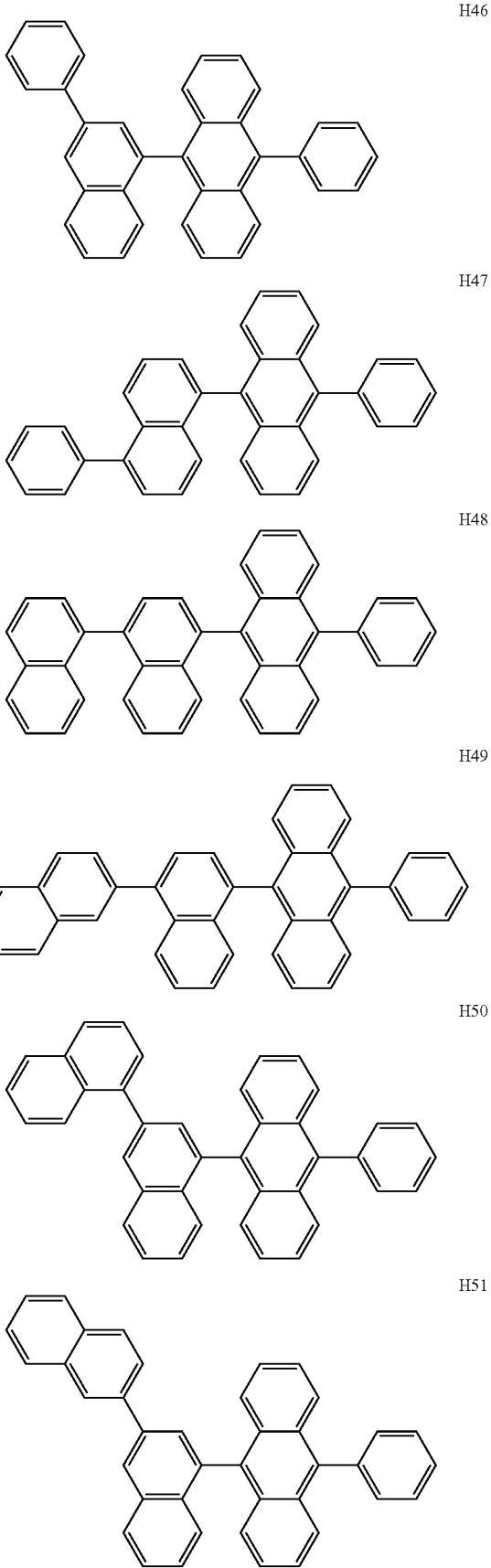

-continued
H52
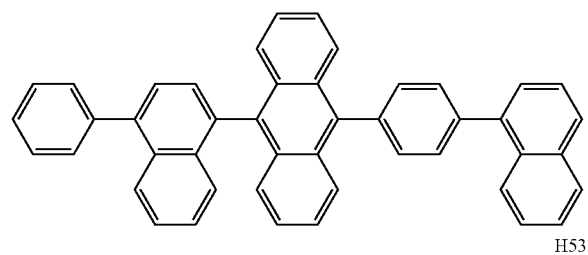
H53
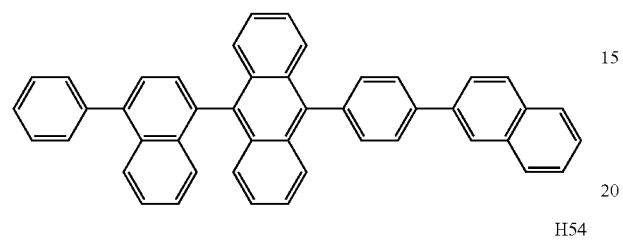
H54
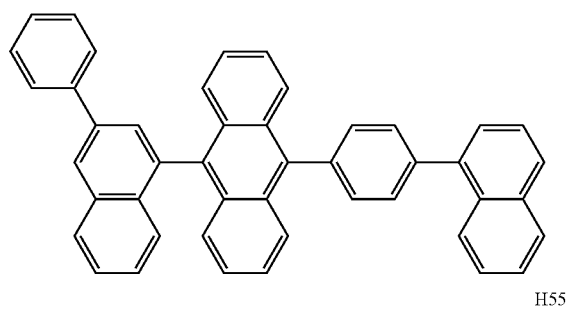
H55
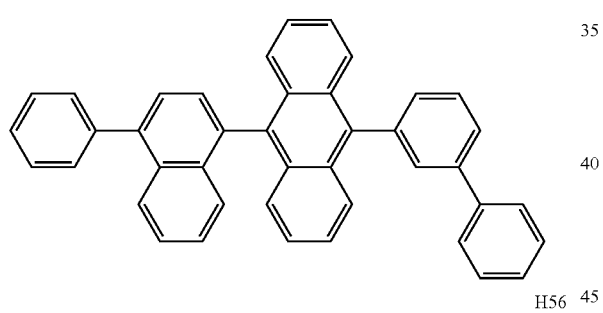
H56
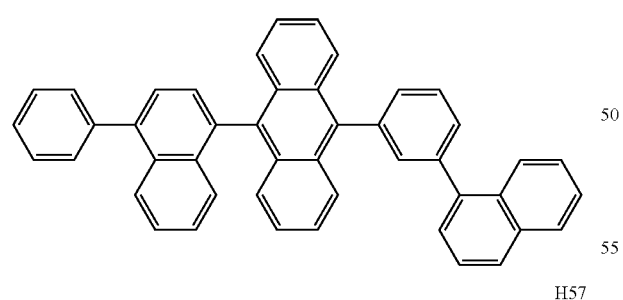
H57
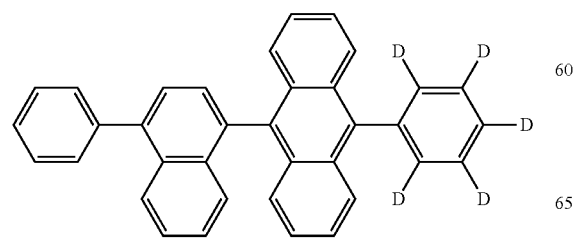
-continued
H58
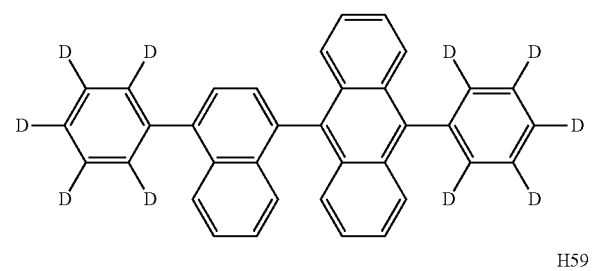
H59
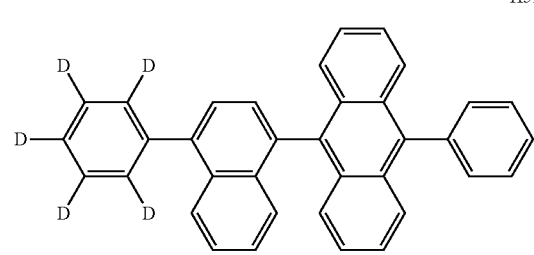
H60
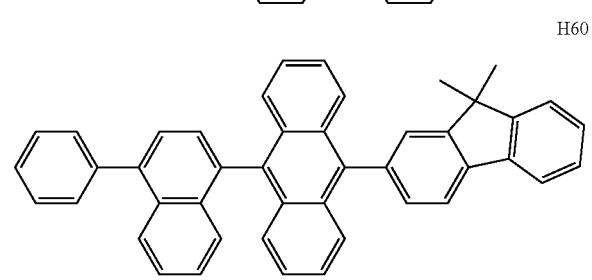
H61
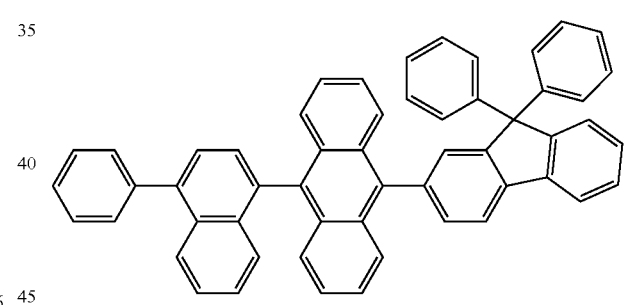
H62
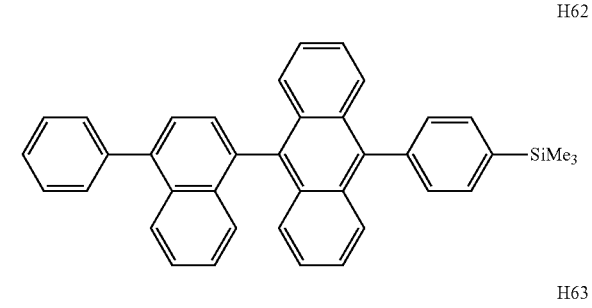
H63
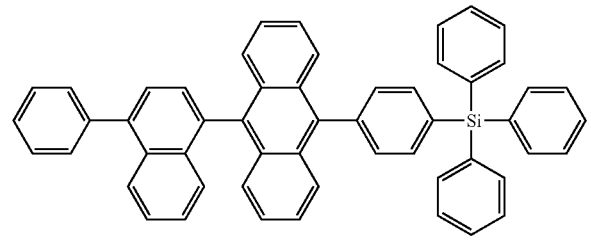

-continued
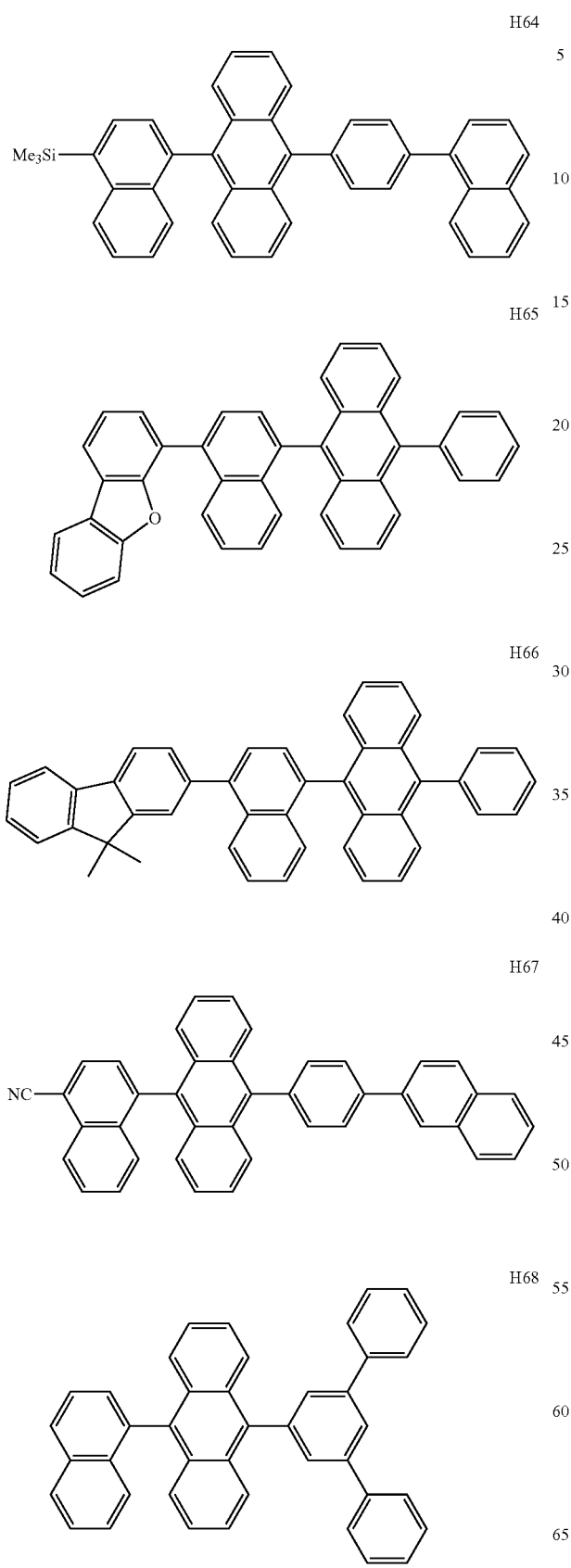
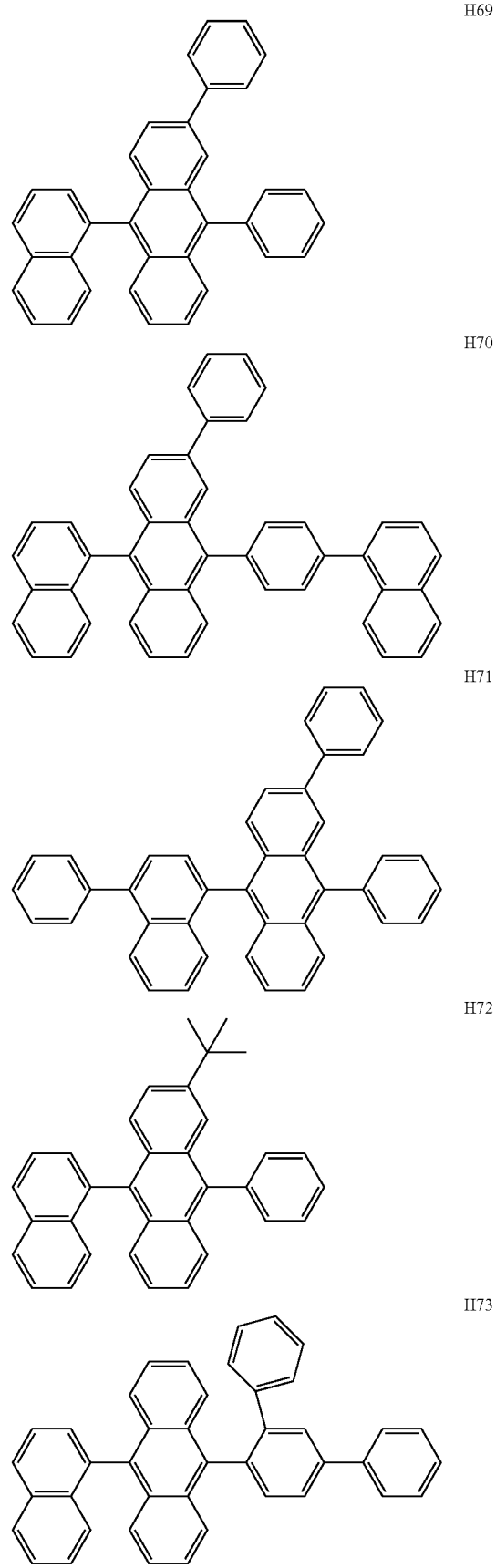

-continued
H74
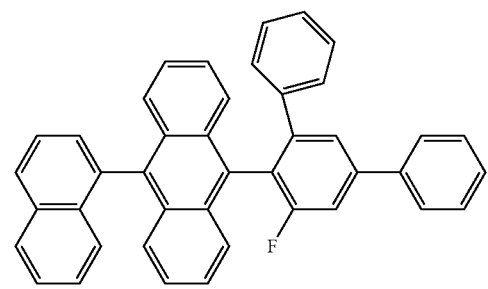
H75
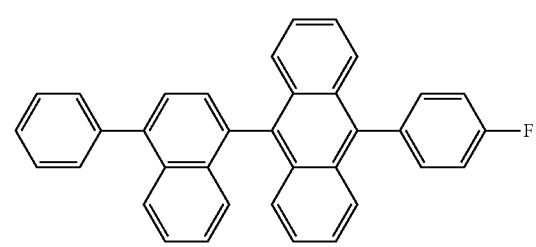
H76
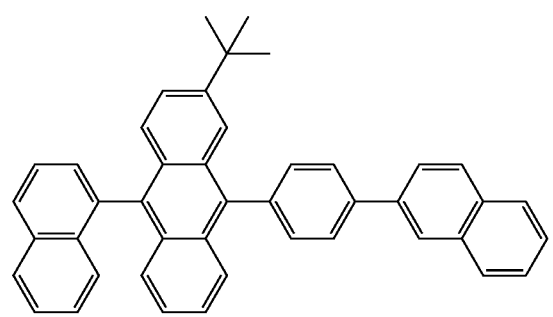
-continued
H77
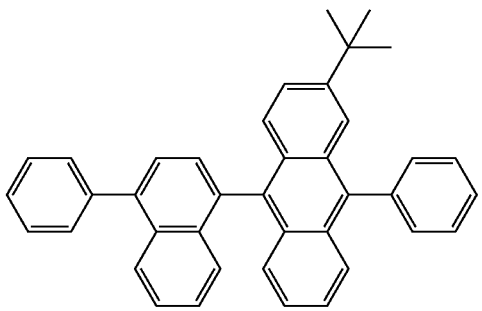
H78
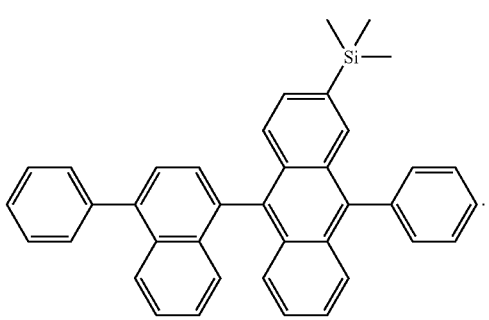
20. A flat panel display apparatus comprising the organic light-emitting device of claim 14,
   wherein the first electrode of the organic light-emitting device is electrically connected to a source electrode or a drain electrode of a thin film transistor.
* * * * *